(12) United States Patent
Ratajczak et al.

(10) Patent No.: US 12,116,592 B2
(45) Date of Patent: Oct. 15, 2024

(54) METHODS AND COMPOSITIONS FOR EX VIVO EXPANSION OF VERY SMALL EMBRYONIC-LIKE STEM CELLS (VSELs)

(71) Applicant: University of Louisville Research Foundation, Inc., Louisville, KY (US)

(72) Inventors: Mariusz Z. Ratajczak, Louisville, KY (US); Janina Ratajczak, Louisville, KY (US); Magdalena Kucia, Louisville, KY (US); Donald Miller, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 327 days.

(21) Appl. No.: 17/385,560

(22) Filed: Jul. 26, 2021

(65) Prior Publication Data
US 2022/0056404 A1 Feb. 24, 2022

Related U.S. Application Data

(62) Division of application No. 16/081,665, filed as application No. PCT/US2017/020696 on Mar. 3, 2017, now Pat. No. 11,072,777.

(60) Provisional application No. 62/303,888, filed on Mar. 4, 2016.

(51) Int. Cl.
| | | |
|---|---|---|
| A61K 35/28 | (2015.01) | |
| A61K 31/19 | (2006.01) | |
| A61K 38/09 | (2006.01) | |
| A61P 43/00 | (2006.01) | |
| C12N 5/0735 | (2010.01) | |
| C12N 5/0775 | (2010.01) | |
| C12N 15/113 | (2010.01) | |

(52) U.S. Cl.
CPC ............ *C12N 5/0606* (2013.01); *A61K 31/19* (2013.01); *A61K 35/28* (2013.01); *A61K 38/09* (2013.01); *A61P 43/00* (2018.01); *C12N 5/0665* (2013.01); *C12N 15/113* (2013.01); *C12N 2500/38* (2013.01); *C12N 2501/15* (2013.01); *C12N 2501/31* (2013.01)

(58) Field of Classification Search
CPC .. C12N 5/0606; C12N 5/0665; C12N 15/113; C12N 2500/38; C12N 2501/15; A61K 31/19; A61K 35/28; A61K 38/09; A61P 43/00
See application file for complete search history.

(56) References Cited

U.S. PATENT DOCUMENTS

| | | |
|---|---|---|
| 5,736,396 A | 4/1998 | Bruder et al. |
| 5,750,397 A | 5/1998 | Tsukamoto et al. |
| 5,843,780 A | 12/1998 | Thomson |
| 6,090,622 A | 7/2000 | Gearhart et al. |
| 6,458,589 B1 | 10/2002 | Rambhatla et al. |
| 7,169,750 B2 | 1/2007 | Bridger et al. |
| 7,422,736 B2 | 9/2008 | Hwang |
| 7,575,921 B2 | 8/2009 | Vacanti et al. |
| 7,816,140 B2 | 10/2010 | Lau et al. |
| 8,252,587 B2 | 8/2012 | Fong et al. |
| 8,859,282 B2 | 10/2014 | Kale et al. |
| 9,079,965 B2 | 7/2015 | Zhou |
| 9,155,762 B2 | 10/2015 | Ratajczak et al. |
| 11,312,940 B2 | 4/2022 | Ratajczak et al. |
| 2004/0018617 A1 | 1/2004 | Hwang |
| 2004/0265281 A1 | 12/2004 | Rodgerson et al. |
| 2005/0181502 A1 | 8/2005 | Furcht et al. |
| 2005/0255588 A1 | 11/2005 | Young et al. |
| 2006/0134783 A1 | 6/2006 | Fong et al. |
| 2006/0233768 A1 | 10/2006 | Hirose et al. |
| 2007/0243172 A1 | 10/2007 | Ra et al. |
| 2008/0038231 A1 | 2/2008 | Rodgerson et al. |
| 2008/0206343 A1 | 8/2008 | Edinger et al. |
| 2008/0241171 A1 | 10/2008 | Gentry et al. |
| 2009/0155225 A1 | 6/2009 | Ratajczak et al. |
| 2009/0162329 A1 | 6/2009 | Anversa et al. |

(Continued)

FOREIGN PATENT DOCUMENTS

| | | |
|---|---|---|
| WO | WO 01/11011 A2 | 2/2001 |
| WO | WO 04043990 A2 | 5/2004 |

(Continued)

OTHER PUBLICATIONS

Basiji et al. (2007) Cellular Image Analysis and Imaging by Flow Cytometry. Clin Lab Med 27:653-670.
Bhartiya et al. (2014) Making gametes from pluripotent stem cells—a promising role for very small embryonic-like stem cells. Reprod Biol Endocrinol 12:114.
Brunt et al. (2012) Stem Cells and Regenerative Medicine—Future Perspectives. Can. J. Physiol. Pharmacol. 90:327-335.

(Continued)

*Primary Examiner* — J. E. Angell
(74) *Attorney, Agent, or Firm* — Jenkins, Taylor & Hunt, P.A.

(57) ABSTRACT

Methods for ex vivo expansion of very small embryonic like stem cells in the absence of feeder cells are provided. In some embodiments the methods include providing a plurality of VSELs; and growing the VSELs in a culture medium that includes a histone deacetylase inhibitor, luteinizing hormone, follicle-stimulating hormone, and optionally transforming growth factor beta in an amount that is sufficient to overcome quiescence of the VSELs. Also provided are feeder cell-free cell cultures, ex vivo expanded VSELs, pharmaceutical compositions that include the disclosed ex vivo expanded VSELs, methods for overcoming quiescence in VSELs, methods for re-establishing imprinting in VSELs, method for treating injuries to tissues in subjects, methods for repopulating cell types in subjects, methods for bone marrow transplantation, methods for treating radiation exposure in subjects, and methods that relate to regenerative medicine.

3 Claims, 9 Drawing Sheets
Specification includes a Sequence Listing.

(56) References Cited

U.S. PATENT DOCUMENTS

| | | | |
|---|---|---|---|
| 2009/0220466 | A1 | 9/2009 | Ratajczak et al. |
| 2010/0267107 | A1 | 10/2010 | Zuba-Surma et al. |
| 2012/0114614 | A1 | 5/2012 | Ratajczak |
| 2014/0154219 | A1 | 6/2014 | Ratajczak et al. |
| 2015/0174173 | A1 | 6/2015 | Ratajczak et al. |
| 2016/0151421 | A1 | 6/2016 | Ratajczak et al. |
| 2017/0108499 | A1 | 4/2017 | Ratajczak et al. |

FOREIGN PATENT DOCUMENTS

| | | | |
|---|---|---|---|
| WO | WO 04089439 | A2 | 10/2004 |
| WO | WO 05042723 | A2 | 5/2005 |
| WO | WO 2007/067280 | | 6/2007 |
| WO | WO 2007/146432 | A2 | 12/2007 |
| WO | WO 2008/087256 | A1 | 7/2008 |
| WO | WO 2010/039241 | | 4/2010 |
| WO | WO 2010/057110 | A1 | 5/2010 |
| WO | WO 2011/069117 | A1 | 6/2011 |
| WO | WO 2015/054315 | A1 | 4/2015 |

OTHER PUBLICATIONS

Burger et al. (2002) Fibroblast Growth Factor Receptor-1 Is Expressed by Endothelial Progenitor Cells. Blood 100:3527-3535.
Carrion et al. (2003) A randomised study of 10 ug/kg/day (single dose) vs 2x5 f.JQ/kg/day (split dose) G-CSF as stem cell mobilisation regimen in high-risk breast cancer patients., Bone Marrow Transplantation 32(6):563-567.
Chen et al., (2001) Therapeutic Benefit of Intravenous Administration of Bone Marrow Stromal Cells After Cerebral Ischemia in Rats, Stoke 32:1005-1011.
Cornetta et al. (1998) Rapid engraftment after allogeneic transplantation using CD34-enriched marrow cells. Bone Marrow Transplantation 21:65-71.
Costa et al. (European Journal of Pharmaceutics and Biopharmaceutics 74 (2010) 127-138). (Year: 2010).
Cottler-Fox et al. (2003) Stem Cell Mobilization. Hematology 419-437.
Crosby et al. (2001) Human Hepatic Stem-like Cells Isolated Using c-kit or CD34 Can Differentiate Into Biliary Epithelium. Gastroenterology 120:534-544.
D'Ippolito et al. (2004) Marrow-isolated adult multilineage inducible (MIAMI) cells, a unique population of postnatal young and old human cells with extensive and differentiation potential. Journal of Cell Science 117(14): 2971-2981.
Danova-Alt et al. (2012) Very Small Embryonic-Like Stem Cells Purified from Umbilical Cord Blood Lack Stem Cell Characteristics. PLoS One 7(4):e34899.
Dawn et al. (2008) Transplantation of bone marrow-derived very small embryonic-like stem cells attenuates left ventricular dysfunction and remodeling after myocardial infarction. Stem Cells, ALP Hamed Press, 26(6): 1646-1655.
European Search Report corresponding to European Application No. 11831724.7 dated Mar. 17, 2014.
European Search Report corresponding to European Application No. 12763497.0-1402/2694651 dated Oct. 29, 2014.
European Search Report corresponding to European Patent Application No. 09826922.8, dated on Jun. 18, 2012.
European Search Report corresponding to European Application No. 12166007.0-2401 dated Nov. 16, 2012.
European Search Report corresponding to European Application No. 17760911.2-1120 dated Oct. 10, 2019.
Fiegel et al. (2003) Characterization of Cell Types During Rat Liver Development. Hepatology 37:148-154.
Gallacher et al. (2000) Isolation and characterization of human CD34-Lin- and CD34+Lin-hematopoietic stem cells using cell surface markers AC133 and CD7. Blood 95:2813-2820.
Grymula et al. (2014) Evidence that the population of quiescent bone marrow-residing very small embryonic/epiblast-like stem cells (VSELs) expands in response to neurotoxic treatment. J Cell Mol Med 18:1797-1806.
Guerin et al. (2015) Bone-marrow-derived very small embryonic-like stem cells in patients with critical leg ischaemia: evidence of vasculogenic potential. Thromb Haemost 113:1084-1094.
Halasa et al. (2008) An efficient two-step method to purify very small embryonic-like (VSEL) stem cells from umbilical cord blood (UCB). Folia Histochemica et Cytobiologica, 46(2):239-243.
Havens et al. (2013) Human very small embryonic-like cells generate skeletal structures, in vivo. Stem Cells Dev 22:622-630.
Havens et al. (2014) Human and murine very small embryonic-like cells represent multipotent tissue progenitors, in vitro and in vivo. Stem Cells Dev 23:689-701.
Haynesworth et al. (1992) Characterization of cells with osteogenic potential from human marrow. Bone 13:81-88.
Hess et al. (2004) Functional characterization of highly purified human hematopoietic repopulating cells isolated according to aldehyde dehydrogenase activity. Blood 104:1648-1655.
Hess et al. (2006) Selection based on CD133 and high aldehyde dehydrogenase activity isolates long-term reconstituting human hematopoietic stem cells. Blood 107:2162-2169.
Hess et al. (2008) Widespread Nonhematopoietic Tissue Distribution by Transplanted Human Progenitor Cells With High Aldehyde Dehydrogenase Activity., Stem Cells, Dayton, Ohio, 26(3):611-620.
Hirschi and Goodell (2002) Hematopoietic, vascular and cardiac fates of bone marrow-derived stem cells. Gene Therapy 9:648-652.
Houssaint (1980) Differentiation of the Mouse Hepatic Primordium. I. An Analysis of Tissue Interactions in Hepatocyte Differentiation. Cell Differ 9:269-279.
International Preliminary Report on Patentability corresponding to Patent Application No. PCT/US07/014108 dated Dec. 16, 2008.
International Preliminary Report on Patentability Corresponding to Patent Application No. PCT/US2008/081832 dated Mar. 25, 2009.
International Preliminary Report on Patentability and Written Opinion of the International Searching Authority corresponding to International Patent Application No. PCT/US06/042780 dated Apr. 24, 2009.
International Preliminary Report on Patentability Corresponding to Patent Application No. PCT/US2009/005414 dated Mar. 2, 2010.
International Preliminary Report on Patentability corresponding to International Patent Application No. PCT/US2009/064614 dated May 26, 2011.
International Preliminary Report on Patentability corresponding to International Patent Application No. PCT/US2011/055473 dated Apr. 9, 2013.
International Preliminary Report on Patentability corresponding to International Patent Application No. PCT/US17/20696 dated Sep. 13, 2018.
International Search Report corresponding to European Application No. PCT/EP2009/064614 dated Feb. 22, 2010.
International Search Report and Written Opinion of International Patent Application No. PCT/US08/81832 dated Mar. 25, 2009.
International Search Report corresponding to U.S. Patent Application No. PCT/US06/042780 dated Jun. 30, 2009.
International Search Report corresponding to International Application No. PCT/US2009/064614, dated on Apr. 2, 2010.
International Search Report corresponding to International Patent Application No. PCT/US09/05414 dated Mar. 2, 2010.
International Search Report corresponding to International Application No. PCT/EP2009/064612 dated Jul. 29, 2010.
International Search Report and Written Opinion of the International Searching Authority Corresponding to Application No. PCT/US 12/31869 dated Jul. 27, 2012.
Interview Summary corresponding to U.S. Appl. No. 13/877,963 dated Jan. 23, 2015.
Interview Summary corresponding to U.S. Appl. No. 13/129,359 dated on Jul. 15, 2015.
Ito et al. (2010) The ACC133+CD38-, but not the rhodamine-low, phenotype tracks LTC-IC and SRC function in human cord blood ex vivo expansion cultures. Blood 115:257-260.
Jiang et al. (2002a) Multipotent progenitor cells can be isolated from postnatal murine bone marrow, muscle and brain. Exp Hematol 30:896-904.
Jiang et al. (2002b) Pluripotency of mesenchymal stem cells derived from adult marrow. Nature 418(6893):41-49.

(56) References Cited

OTHER PUBLICATIONS

Jung et al. (1999) Initiation of Mammalian Liver Development from Endoderm by Fibroblast Growth Factors. Science 284:1998-2003.
Kassmer et al. (2013) Very small embryonic-like stem cells from the murine bone marrow differentiate into epithelial cells of the lung. Stem Cells 31:2759-2766.
Kiel et al. (2005) SLAM Family Receptors Distinguish Resource Hematopoietic Stem and Progenitor Cells and Reveal Endothelial Niches for Stem Cells. Cell 121:1109-1121.
Kim et al. (2010) Bone morphogenetic protein 4 stimulates attachment of neurospheres and astrogenesis of neural stem cells in neurospheres via phosphatidylinositol 3 kinase-mediated upregulation of N-cadherin. Neuroscience 170:8-15 (XP055031897).
Kogler et al. (2004) A new human somatic stem cell from placental cord blood with intrinsic pluripotent differentiation potential. Journal of Experimental Medicine 200(2):123-135.
Krause (2008) Bone Marrow-derived Cells and Stem Cells in Lung Repair. Proc Am Thorac Soc 5:323-327.
Krupnick et al. (2004) Fetal Liver as a Source of Autologous Progenitor Cells for Perinatal Tissue Engineering. Tissue Eng 10:723-735.
Kucia et al. (2004) Cells expressing early cardiac markers reside in the bone marrow and are mobilized into the peripheral blood after myocardial infarction. Circulation Research 95:1191-1199.
Kucia et al. (2005a) Are bone marrow stem cells plastic or heterogenous—That is the question. Experimental Hematology 33(6):613-623.
Kucia et al. (2005b) Bone marrow as a home of heterogeneous populations of nonhematopoietic stem cells., Leukemia (Basingstoke) 19(7):1118-1127.
Kucia et al. (2005c) Bone marrow as a source of circulating CXCR4(+) tissue-committed stem cells. Biology of the Cell 97(2):133-146.
Kucia et al. (2006a) A population of very small embryonic-like (VSEL) CXCR4+SSEA-1+Oct-4+ stem cells identified in adult bone marrow. Leukemia 20:857-869.
Kucia et al. (2006b) A population of very small embryonic-like (VSEL) CXCR4+SSEA-1+0ct4+ stem cells identified in adult bone marrow. Leukemia 20 pp. 857-869.
Kucia et al. (2006c) Cells enriched in markers of neural tissue-committed stem cells reside in the bone marrow and are mobilized into the peripheral blood following stroke. Leukemia 20(18-28).
Kucia et al. (2006d) Physiological and pathological consequences of identification of very small embryonic like (VSEL) stem cells in adult bone marrow., Journal of Physiology and Pharmacology 57 (Supp 5):5-18.
Kucia et al. (2006e) The migration of bone marrow-derived non-hematopoietic tissue-committed stem cells is regulated in an SDF-1, HGF-, and LIF-dependent manner., Archivum Immunologiae et Therapiae Experimentalis, Birkhaeuser Verlag AG. 54:121-135.
Kucia et al. (2007) Morphological and molecular characterization of novel population of CXCR4+ SSEA-4+ Oct-4+ very small embryonic-like cells purified from human cord blood—preliminary report. Leukemia 21:297-303.
Kucia et al. (2008a) Evidence that very small embryonic-like cells are mobilized into peripheral blood. Stem Cells 26:2083-2092.
Kucia et al. (2008b) Identification of very small embryonic like (VSEL) stem cells in bone marrow. Cell and Tissue Research 331:125-134.
Larochelle et al. (1996) Identification of primitive human hematopoietic cells capable of repopulating NOD/SCID mouse bone marrow: Implications for gene therapy. Nat Med 2(12):1329-1337.
Lee et al. (2010) Placenta as a newly identified source of hematopoietic stem cells. Curr Opin Hematol 17:313-318.
Lee et al. (2011) Progesterone promotes differentiation of human cord blood fetal T cells into T regulatory cells but suppresses their differentiation into Th17 cells. J Immunol 187:1778-1787.
Lemmer et al. (1998) Isolation from human fetal liver of cells co-expressing CD34 haematopoietic stem cell and CAM 5.2 pancytokeratin markers. J Hepatol 29:450-454.
Leor et al. (2005) Human umbilical cord blood-derived CD133+ cells enhance function and repair of the infarcted myocardium. Stem Cells 24(3) 772-780.
Luo et al. (2013) Upregulated H19 contributes to bladder cancer cell proliferation by regulating ID2 expression. FEBS J 280:1709-1716.
Luo et al. (Luo et al. Moleuclar Pharmaceutics, 2014, vol. 11, pp. 1750-1761) (Year: 2014).
Mason et al. (2001) CD Antigens 2001. European Journal of Immunology 31(10): 2841-2847.
McGuckin et al. (2005) Production of stem cells with embryonic characteristics from human umbilical cord blood. Cell Prolif 38:245-255.
McGuckin et al. (2008) Culture of embryonic-like stem cells from human umbilical cord blood and onward differentiation to neural cells in vitro. Nature Protocols 3(6):1046-1055.
McKinney-Freeman et al. (2002) Muscle-derived hematopoietic stem cells are hematopoietic in origin. Proc Natl Acad Sci USA 99:1341-1346.
Medicetty et al. (2009) Evidence That Human Very Small Embryonic-Like Stem Cells (VSELs) are Mobilized by G-CSF Into Peripherial Blood: A Novel Strategy to Obtain Human Pluripotent Stem Cells for Regenerative Medicine. Blood 114:1474.
Mierzejewska et al. (2015) Hematopoietic stem/progenitor cells express several functional sex hormone receptors-novel evidence for a potential developmental link between hematopoiesis and primordial germ cells. Stem Cells Dev 24:927-937.
Miki et al. (2005) Stem Cell Characteristics of Amniotic Epithelial Cells. Stem Cells 23:1549-1559.
Mimura et al. (2005) Treatment of Rabbit Bullous Keratopathy with Precursors Derived from Cultured Human Corneal Endothilium, Investigative Ophthalmology and Visual Science 46:3637-3644.
Minguet et al. (2003) A population of c-Kitlow(CD45/TER119)—hepatic cell progenitors of 11-day postcoitus mouse embryo liver reconstitutes cell-depleted liver organoids. J Clin Invest 112:1152-1163.
Nakada et al. (2014) Oestrogen increases haematopoietic stem-cell self-renewal in females and during pregnancy. Nature. 505:555-558.
Naldini. (2011) Ex vivo gene transfer and correction for cell-based therapies. Nature Reviews: Genetics 12:301-315.
Nava et al. (2005) Characterization of cells in the developing human liver. Differentiation 73:249-260.
Nguyen et al. (2010) Methods to Assess Stem Cell Lineage, Fate and Function. Advanced Drug Delivery Reviews. 62:1175-1186.
Nierhoff et al. (2005) Purification and characterization of mouse fetal liver epithelial cells with high in vivo repopulation capacity. Hepatology 42:130-139.
Notice of Allowance and Fee(s) Due and Examiner Initiated Interview Summary for U.S. Appl. No. 12/740,718 dated May 29, 2015.
Notice of Allowance corresponding to U.S. Appl. No. 15/253,239 dated Jan. 7, 2022.
Notification Concerning Transmittal of International Preliminary Report on Patentability (Chapter I of the Patent Cooperation Treaty), corresponding to International application PCT/US2013/047435 dated Jan. 8, 2015.
Notice of Intent to Grant corresponding to European Patent Application No. 12166007.0 dated Jan. 9, 2019.
Notification of Transmittal of the International Search Report and the Written Opinion of the International Searching Authority, or the Declaration, corresponding to International application PCT/US17/20696 dated May 31, 2017.
Notification of Transmittal of the International Search Report and the Written Opinion of the International Searching Authority, or the Declaration, corresponding to International application PCT/US2013/047435 dated Nov. 29, 2013.
Notification of Transmittal of the International Search Report and the Written Opinion of the International Searching Authority corresponding to International Patent Application No. PCT/US2011/55473 dated Feb. 23, 2012.
Notification of Transmittal of the International Search Report and the Written Opinion of the International Searching Authority, or the Declaration for International Application No. PCT/US09/64612 dated Apr. 9, 2010.

(56) References Cited

OTHER PUBLICATIONS

Nowak et al. (2005) Identification of expandable human hepatic progenitors which differentiate into mature hepatic cells in vivo. Gut 54:972-979.
Office Action corresponding to European Patent Application No. EP 078 09 600.5 dated May 11, 2009.
Office Action corresponding to Australian Patent Application No. 2011312128 dated Oct. 10, 2014.
Office Action corresponding to European Patent Application No. 09826922.8 dated Aug. 26, 2014.
Office Action corresponding to European Patent Application No. 11 831 724.7-1408 dated Dec. 8, 2014.
Office Action corresponding to U.S. Appl. No. 13/129,359 dated Oct. 30, 2014.
Office Action corresponding to U.S. Appl. No. 13/129,359 dated Jun. 20, 2013. .
Office Action corresponding to U.S. Appl. No. 13/129,359 dated Oct. 12, 2012.
Office Action corresponding to U.S. Appl. No. 13/129,359 dated Jun. 3, 2015.
Office Action corresponding to U.S. Appl. No. 13/129,352 dated May 2, 2014.
Office Action corresponding to U.S. Appl. No. 13/877,963 dated Mar. 6, 2015.
Office Action corresponding to U.S. Appl. No. 14/136,436 dated Mar. 26, 2015.
Office Action corresponding to U.S. Appl. No. 12/096,754 dated Nov. 22, 2011.
Office Action corresponding to U.S. Appl. No. 13/121,913 dated Dec. 13, 2011.
Office Action corresponding to U.S. Appl. No. 12/096,754 dated Jul. 30, 2012.
Office Action corresponding to U.S. Appl. No. 14/008,796 dated May 4, 2015.
Office Action corresponding to U.S. Appl. No. 14/008,796 dated Nov. 2, 2015.
Office Action corresponding to U.S. Appl. No. 14/958,409 dated Feb. 3, 2017.
Office Action corresponding to U.S. Appl. No. 14/844,980 dated Aug. 22, 2016.
Office Action corresponding to U.S. Appl. No. 14/844,980 dated Apr. 21, 2017.
Office Action corresponding to U.S. Appl. No. 14/844,980 dated Dec. 1, 2017.
Office Action corresponding to U.S. Appl. No. 14/844,980 dated Aug. 8, 2018.
Office Action corresponding to U.S. Appl. No. 12/740,718 dated Oct. 4, 2012.
Office Action corresponding to Chinese Patent Application No. 200980154497.X dated Dec. 6, 2012.
Office Action corresponding to U.S. Appl. No. 12/740,718 dated May 31, 2013.
Office Action corresponding to Chinese Patent Application No. 200980154497.X dated Sep. 30, 2013.
Office Action corresponding to U.S. Appl. No. 12/740,718 dated Sep. 30, 2014.
Office Action corresponding to U.S. Appl. No. 14/409,507 dated Aug. 10, 2016.
Office Action corresponding to U.S. Appl. No. 15/253,239 dated Apr. 19, 2019.
Office Action corresponding to U.S. Appl. No. 15/253,239 dated Feb. 6, 2020.
Office Action corresponding to U.S. Appl. No. 15/253,239 dated Jul. 1, 2021.
Okuno et al. (PNAS, Apr. 30, 2002, vol. 99, No. 9, pp. 6246-6251) (Year: 2002).
Paczkowska et al. (2005) Human hematopoietic stem/progenitor-enriched CD34(+) cells are mobilized into peripheral blood during stress related to ischemic stroke or acute myoyardial infarction. European Journal of Heamatology 75(6):461-467.
Paczkowska et al. (2009) Clinical evidence that very small embryonic-like stem cells are mobilized into peripheral blood in patients after stroke. Stroke 40:1237-1244.
Patel et al. (2013) Follicle Stimulating Hormone Modulated Ovarian Stem Cells through alternately spliced receptor variant FSH-R3. J. of Ova. Res 6:1-15.
Pelacho et al. (2007) Multipotent adult progenitor cell transplantation increases vascularity and improves left ventricular function after myocardial infarction., Journal of Tissue Engineering and Regeneratice Medicine 1:51-59.
Peterson et al. (1998) Hepatic Oval Cells Express the Hematopoietic Stem Cell Marker Thy-1 in the Rat. Hepatology 27:433-445.
Petit et al. (2002) G-CSF induces stem cell mobilization by decreasing bond marrow SDF-1 and up-regulating CXCR4., Nature Immunology 3(7):687-694.
Pittenger et al. (2000) Human mesenchymal stem cells: progenitor cells for cartilage, bone, fat and stroma. Curr Top Microbiol Immunol 251:1-10.
Prockop (1997) Marrow Stromal Cells as Stem Cells for Nonhematopoietic Tissues., Science, 276(5309):71-74.
Ratajczak et al. (1994) A reappraisal of the role of insulin-like growth factor I in the regulation of human hematopoiesis. J Clin Invest 94:320-327.
Ratajczak et al. (2003) Expression of functional CXCR4 by muscle satellite cells and secretion of SDF-1 by muscle-derived fibroblasts is associated with the presence of both muscle progenitors in bone marrow and hematopoietic stem/progenitor cells in muscles. Stem Cells 21:363-371.
Ratajczak et al. (2004) Stem cell plasticity revisited: CXCR4-positive cells expressing mRNA for early muscle, liver and neural cells 'hide out' in the bone marrow, Leukemia 18:29-40.
Ratajczak et al. (2006) The pleiotropic effects of the SDF-1-CXCR4 axis in organigenesis, regeneration and tumorigenesis. Leukemia 20:1915-1924.
Ratajczak et al. (2007) A hypothesis for an embryonic origin of pluripotent Oct-4+ stem cells in adult bone marrow and other tissues. Leukemia 21:860-867.
Ratajczak (2008a) Phenotypic and functional characterization of hematopoietic stem cells. Curr Opin Hematol 15:293-300.
Ratajczak et al. (2008b) Very Small Embryonic-Like (VSEL) Stem Cells: Purification from Adult Organs, Characterization, and Biological Significance. Stem Cell Research 4:89-99.
Ratajczak et al. (2008c) Very Small Embryonic Like (VSEL) Stem Cells—Characterization, Developmental Origin and Biological Significance. Exp Hematol 36:742-751.
Ratajczak et al. (2008d) Very small embryonic-like (VSEL) stem cells in adult organs and their potential role in rejuvenation of tissues and longevity. Experimental Gerontology 43:1009-1017.
Ratajczak et al. (2008e) Very Small Embryonic-Like (VSEL) Stem Cells: Purification from Adult Organs, Characterization, and Biological Significance. J Autoimmun 30:151-162.
Ratajczak et al. (2008f) Very Small Embryonic-Like (VSEL) Stem Cells: Purification from Adult Organs, Characterization, and Biological Significance. Stem Cell Rev 4:89-99.
Ratajczak et al. (2011a) Adult murine bone marrow-derived very small embryonic-like stem cells differentiate into the hematopoietic lineage after coculture over OP9 stromal cells. Experimental Hematology 39(2):225-237.
Ratajczak et al. (2011b) Hematopoietic differentiation of umbilical cord blood-derived very small embryonic/epiblast-like stem cells. Leukemia 25:1278-1285.
Ratajczak et al. (2011c) Stem cells for neural regeneration—a potential application of very small embryonic-like stem cells. J Physiol Pharmacol 62(1):3-12.
Ratajczak et al. (2012a) A novel perspective on stem cell homing and mobilization: review on bioactive lipids as potent chemoattractants and cationic peptides as underappreciated modulators of responsiveness to SDF-1 gradients. Leukemia 26:63-72.
Ratajczak et al. (2017) A Novel View of the Adult Stem Cell Compartment From the Perspective of a Quiescent Population of Very Small Embryonic-Like Stem Cells. Circ. Res. 120:166-178.

(56) References Cited

OTHER PUBLICATIONS

Reynolds & Weiss (2005) Clonal and population analyses demonstrate that an EGF-responsive mammalian embryonic CNS precursor is a stem cell. Developmental Biology 175:1-13.

Rich (1995) Primordial germ cells are capable of producing cells of the hematopoietic system in vitro. Blood 86:463-472.

Rossi et al. (2001) Distinct mesodermal signals, including BMPs from the septum transversum mesenchyme, are required in combination for hepatogenesis from the endoderm. Genes Dev 15:1998-2009.

Saitoh et al. (1999) Comparison of erythropoietic response to androgen in young and old senescence accelerated mice. Mech Ageing Dev 109:125-139.

Sanchez-Aguilera et al. (2014) Estrogen signaling selectively induces apoptosis of hematopoietic progenitors and myeloid neoplasms without harming steady-state hematopoiesis. Cell Stem Cell 15:791-804.

Shin et al. (2009) Novel epigenetic mechanisms that control pluripotency and quiescence of adult bone marrow-derived Oct4(+) very small embryonic like stem cells. Leukemia 23(11):2042-2051.

Sovalat et al. (2011) Identification and isolation from either adult human bone marrow or G-CSF-mobilized peripheral blood of CD34(+)/CD133(+)/CXCR4(+)/ Lin(-)CD45(-) cells, featuring morphological, molecular, and phenotypic characteristics of very small embryonic-like (VSEL) stem cells. Exp Hematology 39:495-505.

Stilley et al. (2014) Signaling through FSH receptors on human umbilical vein endothelial cells promotes angiogenesis. J Clin Endocrinol Metab 99:E813-E820.

Stimpfel et al. (2013) Isolation, characterization and differentiation of cells expressing pluripotent/multipotent markers from adult human ovaries. Cell Tissue Res 354:593-607.

Supplementary Search Report corresponding to European Patent Application No. 06827358.0 dated Dec. 30, 2009.

Suszynska et al. (2014a) The proper criteria for identification and sorting of very small embryonic-like stem cells, and some nomenclature issues. Stem Cells and Development 23(7):702-713.

Suszynska et al. (2014b) Expression of the erythropoietin receptor by germline-derived cells—further support for a potential developmental link between the germline and hematopoiesis. J Ovarian Res 7:66.

Suzuki et al. (2000) Flow-Cytometric Separation and Enrichment of Hepatic Progenitor Cells in the Developing Mouse Liver. Hepatology 32:1230-1239.

Suzuki & Nakauchi (2002a) Identification and propagation of liver stem cells. Semin Cell Dev Biol 13:455-461.

Suzuki et al. (2002b) Clonal identification and characterization of self-renewing pluripotent stem cells in the developing liver. J Cell Biol 156:173-184.

Sylvester et al. (2004) Stem cells: review and update. Arch Surg 139:93-99.

Tada et al. (2006) Morphological Study of the Transition of Haematopoietic Sites in the Developing Mouse During the Perinatal Period. Anat Histol Embryol 35:235-240.

Taichman et al. (2010) Prospective Identification and Skeletal Localization of Cells Capable of Multilineage Differentiation In Vivo. Stem Cells Dev 19:1557-1570.

Takamaru et al. (2012) Aberrant methylation of RASGRF1 is associated with an epigenetic field defect and increased risk of gastric cancer. Cancer Prev Res 5(10):1203-1212.

Tamamura et al. (1998) A Low-Molecular Weight Inhibitor Against the Chemokine Receptor CXCR4: A Strong Anti-HIV Peptide T140. Biochem Blophys Res Commun 253:877-882.

Tanaka et al. (2002) Effect of Continuous Subcutaneous Administration of a Low Dose of G-CSF on Stem Cell Mobilization in Healthy Donors: A Feasibility Study. International Journal of Hematology, 75(5): 489-492.

Tavian & Peault (2005) Embryonic development of the human hematopoietic system. Int J Dev Biol 49:243-250.

Wang et al. (2003) SCID-repopulating cell activity of human cord blood-derived CD34 cells assured by intra-bone marrow injection. Blood 101:2924-2931.

Wiktor-Jedrzejczak et al. (1979) Different marrow cell number requirements for the haemopoietic colony formation and the curve of the W/Wv anemia. Experientia 35:546-547.

Yu et al. (1987) Importance of FSH-releasing protein and inhibin in erythrodifferentiation. Nature 330:765-767.

Zaret (2000) Liver specification and early morphogenesis. Mech Dev 92:83-88.

Zaret (2001) Hepatocyte differentiation: from the endoderm and beyond. Curr Opin Genet Dev 11:568-574.

Zaret (2002) Regulatory Phases of Early Liver Development: Paradigms of Organogenesis. Nat Rev Genet 3:499-512.

Zbucka-Kretowsha et al. (2016) Effective Mobilization of very samall Embryonic-Like Stem Cells and Hematopoietic Stem/Progenitor Cells but Not Endothelial Progenitor Cells by Follicle-Stimulating Hormone Therapy. Stem Cells International 2016:1-8.

Zuo et al. (Protein Engineering, vol. 13, No. 5, pp. 361-367, 2000) (Year: 2000).

Zuba-Surma et al. (2007a) Abstract 1276: Pluripotent Bone Marrow (BM)-Derived Very Small Embryonic-Like (VSEL) Stem Cells are Mobilized after Acute Myocardial Infarction in Mice. Circulation 116(II):260.

Zuba-Surma et al. (2007b) The ImageStream System: a key step to a new era in imaging. Folia Histochem Cytobiol 45(4):279-290.

Zuba-Surma et al. (2008a) CD45-/ALDH (low)/SSEA-4(+)/Oct-4(+)/CD133(+)/CXCR4(+)/Lin(-) Very Small Embryonic-Like (VSEL) Stem Cells Isolated from Umbilical Cord Blood as Potential Long Term Repopulating Hematopoietic Stem Cells. Blood 112(11):1-2 (Abstract).

Zuba-Surma et al. (2008b) Very Small Embryonic-Like Stem Cells are Present in Adult Murine Organs: ImageStream-Based Morphological Analysis and Distribution Studies. Cytometry Part A 73A:1116-1127.

Zuba-Surma et al. (2008c) Morphological characterization of very small embryonic-like stem cells (VSELs) by ImageStream system analysis. J Cell Mol Med 12(1):292-303.

Zuba-Surma et al. (2009a) CD45-/Lin-/CD133+/ALDH-low VSEL stem cells isolated from cord blood-as potential long term repopulating hematopoietic stem cells (LT-HSC). Human Gene Therapy 20(11):1469-1470.

Zuba-Surma et al. (2009c) In Vitro and In Vivo Evidence That Umbilical Cord Blood (UCB)-DerivedCD45-/SSEA-4+/OCT-4+/CD133+/ CXCR4+/Lin—Very Small Embryonic/Epiblast Like Stem Cells (VSELs) Do Not Contain Clonogenic Hematopoietic Progenitors but are Highly Enriched in More Primitive Stem Cells. 51st Ash Annual Meeting and Exposition, Abstract No. 35:1-2.

Zuba-Surma & Ratajczak (2010a) Overview of very small embryonic-like stem cells (VSELs) and methodology of their identification and isolation by flow cytometric methods. Curr Protoc Cytom Chapter 9.25:1-15.

Zuba-Surma et al. (2010b) Optimization of isolation and further characterization of umbilical cord blood-derived very small embryonic/epiblast-like stem cells (VSELs). Eur J Haematol 84:34-46.

Murine VSELs (Sca1+lin−CD45−)
VPA+LH+FSH

METHODS AND COMPOSITIONS FOR EX VIVO EXPANSION OF VERY SMALL EMBRYONIC-LIKE STEM CELLS (VSELs)

CROSS REFERENCE TO RELATED APPLICATION

This application is a divisional of U.S. patent application Ser. No. 16/081,665, filed Aug. 31, 2018, which is itself a U.S. National Stage entry of PCT International Patent Application Serial No. PCT/US2017/020696, filed Mar. 3, 2017, which is based on and claims priority to U.S. Provisional Patent Application Ser. No. 62/303,888, filed Mar. 4, 2016. The disclosure of each of these applications is incorporated by reference herein in its entirety.

TECHNICAL FIELD

The presently disclosed subject matter relates in some embodiments to methods for ex vivo expansion of VSELs. Also provided are cultures comprising ex vivo expanded VSELs and methods for using the same. Further provided are methods and compositions for modulating sirtuin biological activities such as, but not limited to sirtuin biological activities in VSELs in order to enhance expansion of VSELs in culture.

BACKGROUND

The use of pluripotent cells and derivatives thereof has gained increased interest in medical research, particularly in the area of regenerative medicine. Ideally, pluripotent cells that are capable of differentiating into the affected cell types could be transplanted into a subject in need thereof, where they would interact with the organ microenvironment and supply the necessary cell types to repair the consequences of tissue damage resulting from genetic defects, injuries, and/or disease processes.

It would also be beneficial to be able to isolate, purify, and optionally expand stem cells and/or other pluripotent cells from a subject that could thereafter be further purified and/or manipulated in vitro before being reintroduced into the subject for treatment purposes. The use of a subject's own cells would also have advantages, particularly with respect to obviating the need to employ adjunct immunosuppressive therapy, thereby maintaining the competency of the subject's immune system. Alternatively or in addition, it would be beneficial to be able to confirm that appropriate cells have been isolated, and/or assess the purity of stem cells and/or other pluripotent cells in a cell population isolated from a subject.

Considerable effort has thus been expended to isolate pluripotent cells from a number of different tissues for use in regenerative medicine. For example, U.S. Pat. No. 5,750,397 to Tsukamoto et al. discloses the isolation and growth of human hematopoietic stem cells (HSCs) that are reported to be capable of differentiating into lymphoid, erythroid, and myelomonocytic lineages. Bone marrow (BM) HSCs have also been reported to be able to "transdifferentiate" into cells that express early heart (Orlic et al., 2003; Makino et al., 1999), skeletal muscle (Labarge & Blau, 2002; Corti et al., 2002), neural (Sanchez-Ramos, 2002), liver (Petersen et al., 1999), or pancreatic cell (Ianus et al., 2003; Lee & Stoffel, 2003) markers. In vivo experiments in humans also demonstrated that transplantation of $CD34^+$ peripheral blood (PB) stem cells led to the appearance of donor-derived hepatocytes (Korbling et al., 2002), epithelial cells (Korbling et al., 2002), and neurons (Hao et al., 2003). Additionally, human BM-derived cells have been shown to contribute to the regeneration of infarcted myocardium (Stamm et al., 2003).

U.S. Pat. No. 5,736,396 to Bruder et al. discloses methods for lineage-directed differentiation of isolated human mesenchymal stem cells (MSCs) under the influence of appropriate growth and/or differentiation factors. The derived cells can then be introduced into a host for mesenchymal tissue regeneration or repair. MSCs have been shown to have the potential to differentiate into several lineages including bone (Haynesworth et al., 1992), cartilage (Mackay et al., 1998; Yoo et al., 1998), adipose tissue (Pittenger et al., 2000), tendon (Young et al., 1998), muscle, and stroma (Caplan et al., 2001).

Another population of cells, multipotent adult progenitor cells (MAPCs), has also been purified from bone marrow (BM; Reyes et al., 2001; Reyes & Verfaillie, 2001). These cells have been shown to be capable of expansion in vitro for more than 100 population doublings without telomere shortening or the development of karyotypic abnormalities. MAPCs have also been shown to be able to differentiate under defined culture conditions into various mesenchymal cell types (e.g., osteoblasts, chondroblasts, adipocytes, and skeletal myoblasts), endothelium, neuroectoderm cells, and hepatocytes (Schwartz et al., 2000).

Very small embryonic like stem cells (VSELs) are stem cells that could potentially be employed in regenerative medicine. These cells have been identified in human umbilical cord blood, mobilized peripheral blood, bone marrow (see e.g., PCT International Patent Application Publication No. WO 2007/067280; U.S. Patent Application Publication Nos. 2009/0155225, 2009/0220466, 2010/0267107, 2012/0114614, and 2014/0154219; Kucia et al., 2006; Kucia et al., 2007; Kucia et al., 2009; Ratajczak et al., 2008), and adipose tissue as population of small cells that express several markers of pluripotency. VSELs exhibit a primitive morphology and are characterized by expression of several markers typical for pluripotent stem cells (e.g., expression of Oct4, Nanog, and the presence of bivalent domains). An important feature of VSELs is that in contrast to embryonic stem (ES) cells or induced pluripotent stem (iPS) cells, VSELs do not grow teratomas in mice.

However, there are at least two major hurdles before VSELs can be widely employed in the clinic. First, VSELs are very rare. Only about 1,000-5,000 VSELs can be isolated from 100 ml of umbilical cord blood (see U.S. Patent Application Publication No. 2014/0154219). Although the numbers of VSELs in adult human tissues data are lacking, adult murine tissues appear to contain less than about 11,000 VSELs per gram of tissue in bone marrow, heart, skeletal muscle, testes, and liver, less than about 50,000 VSELs per gram of tissue in thymus, spleen, pancreas, brain, kidney, and lungs, and about 120,000 VSELs per gram of tissue in brain (see Zuba-Surma et al., 2000). It is noted, however, that adipose tissue is also a potential source of VSELs.

Second, VSELs reside in adult tissues in a quiescent state. This greatly complicates efforts to employ VSELs for regenerative medicine since the relatively few VSELs that can be isolated from biological sources cannot be effectively expanded ex vivo to provide a sufficient number of VSELs for these uses.

Thus, it is an object of the presently disclosed subject matter to provide methods for ex vivo expansion of VSELs.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides methods for ex vivo expansion of very small embryonic like stem cells (VSELs). In some embodiments, the ex vivo expansion occurs in the absence of feeder cells. In some embodiments, the methods comprise (a) providing a plurality of VSELs; and (b) growing the VSELs in a culture medium that comprises a histone deacetylase (HDAC) inhibitor, luteinizing hormone (LH), follicle-stimulating hormone (FSH), and optionally transforming growth factor beta (TGFβ), wherein the culture medium comprises an effective amount of the HDAC inhibitor, LH, FSH, and optionally TGFβ to overcome quiescence of the VSELs, resulting in expansion of the VSELs.

In some embodiments, the HDAC inhibitor is valproic acid (VPA). In some embodiments, the HDAC inhibitor is an inhibitor of a sirtuin biological activity, optionally an inhibitory nucleic acid that hybridizes to a member of the sirtuin (Sirt) family of mono-ADP-ribosyltransferases or deacylases. In some embodiments, the inhibitory nucleic acid that hybridizes to the member of the Sirt family comprises an siRNA that is directed against a human SIRT, optionally a human SIRT that is encoded by a nucleic acid as set forth in any of GENBANK® Accession Nos. NM_012238 (SEQ ID NO: 1), NM_001142498 (SEQ ID NO: 3), and NM_001314049 (SEQ ID NO: 5). In some embodiments, the inhibitory nucleic acid is a microRNA selected from the group consisting of an miR-34 microRNA, optionally an miR-34a microRNA (e.g., SEQ ID NOs: 7-20); an miR-449 microRNA, optionally an miR-449a, miR-449b, or miR-449c microRNA (e.g., SEQ ID NOs: 11-19); and an miR-200 microRNA, optionally an miR-200a, miR-200b, or miR-200c microRNA (e.g., SEQ ID NOs: 20-28).

In some embodiments, the culture medium comprises 10 U/ml LH, 10 U/ml FSH, 1 mM VPA, and optionally 10 ng/ml TGFβ. In some embodiments, the culture medium comprises 10 U/ml LH, 10 U/ml FSH, 2.5 mM NAM, and optionally 10 ng/ml TGFβ.

The presently disclosed subject matter also provides in some embodiments feeder cell-free cell cultures comprising a plurality of VSELs, one or more ex vivo expanded VSELs, and a culture medium, wherein the culture medium comprises a bovine serum or a serum replacement, a histone deacetylase (HDAC) inhibitor, luteinizing hormone (LH), follicle-stimulating hormone (FSH), and optionally transforming growth factor beta (TGFβ) which together are present in an effective amount to overcome quiescence of the VSELs, resulting in expansion of the VSELs. In some embodiments, the culture medium comprises 10 U/ml LH, 10 U/ml FSH, 1 mM VPA, and optionally 10 ng/ml TGFβ. In some embodiments, the culture medium comprises 10 U/ml LH, 10 U/ml FSH, 2.5 mM NAM, and optionally 10 ng/ml TGFβ. In some embodiments, the VSELs and/or the expanded VSELs are maintained in the cell culture for at least about one or two months.

The presently disclosed subject matter also provides in some embodiments ex vivo expanded VSELs produced by the presently disclosed methods.

The presently disclosed subject matter also provides in some embodiments pharmaceutical compositions comprising the presently disclosed ex vivo expanded VSELs and a pharmaceutically acceptable carrier, optionally wherein the pharmaceutical composition comprises about $1 \times 10^5$ ex vivo expanded VSELs/ml to about $1 \times 10^9$ ex vivo expanded VSELs/ml. In some embodiments, the pharmaceutically acceptable carrier is acceptable for use in a human.

The presently disclosed subject matter also provides in some embodiments methods for overcoming quiescence in VSELs. In some embodiments, the methods comprise growing the VSELs in a culture medium that comprises a histone deacetylase (HDAC) inhibitor, luteinizing hormone (LH), follicle-stimulating hormone (FSH), and optionally transforming growth factor beta (TGFβ), wherein the culture medium comprises an effective amount of the HDAC inhibitor, LH, FSH, and optionally TGFβ to overcome quiescence of the VSELs.

In some embodiments, the HDAC inhibitor is selected from the group consisting of valproic acid (VPA), nicotinic acid, and nicotinamide (NAM). In some embodiments, the HDAC inhibitor is an inhibitor of a sirtuin biological activity, optionally an inhibitory nucleic acid that hybridizes to a member of the sirtuin (Sirt) family of mono-ADP-ribosyltransferases or deacylases. In some embodiments, the inhibitory nucleic acid that hybridizes to the member of the Sirt family comprises an siRNA that is directed against a human SIRT, optionally a human SIRT that is encoded by a nucleic acid as set forth in any of GENBANK® Accession Nos. NM_012238 (SEQ ID NO: 1), NM_001142498 (SEQ ID NO: 3), and NM_001314049 (SEQ ID NO: 5). In some embodiments, the inhibitory nucleic acid is a microRNA selected from the group consisting of an miR-34 microRNA, optionally an miR-34a microRNA (e.g., SEQ ID NOs: 7-10); an miR-449 microRNA, optionally an miR-449a, miR-449b, or miR-449c microRNA (e.g., SEQ ID NOs: 11-19); and an miR-200 microRNA, optionally an miR-200a, miR-200b, or miR-200c microRNA (e.g., SEQ ID NOs: 20-28). In some embodiments, the culture medium comprises 10 U/ml LH, 10 U/ml FSH, 1 mM VPA, and optionally 10 ng/ml TGFβ.

The presently disclosed subject matter also provides in some embodiments methods for re-establishing imprinting in VSELs. In some embodiments, the methods comprise culturing the VSEL in a culture medium that comprises a histone deacetylase (HDAC) inhibitor, luteinizing hormone (LH), follicle-stimulating hormone (FSH), and optionally transforming growth factor beta (TGFβ), wherein the culture medium comprises an effective amount of the HDAC inhibitor, LH, FSH, and optionally TGFβ to overcome quiescence of the VSELs. In some embodiments, the HDAC inhibitor is valproic acid (VPA). In some embodiments, the HDAC inhibitor is an inhibitor of a sirtuin biological activity, optionally an inhibitory nucleic acid that hybridizes to a member of the sirtuin (Sirt) family of mono-ADP-ribosyltransferases or deacylases. In some embodiments, the inhibitory nucleic acid that hybridizes to the member of the Sirt family comprises an siRNA that is directed against a human SIRT, optionally a human SIRT that is encoded by a nucleic acid as set forth in any of GENBANK® Accession Nos. NM_012238 (SEQ ID NO: 1), NM_001142498 (SEQ ID NO: 3), and NM_001314049 (SEQ ID NO: 5). In some embodiments, the inhibitory nucleic acid is a microRNA selected from the group consisting of an miR-34 microRNA, optionally an miR-34a microRNA (e.g., SEQ ID NOs: 7-10); an miR-449 microRNA, optionally an miR-449a, miR-449b, or miR-449c microRNA (e.g., SEQ ID NOs:

11-19); and an miR-200 microRNA, optionally an miR-200a, miR-200b, or miR-200c microRNA (e.g., SEQ ID NOs: 20-28). In some embodiments, the culture medium comprises 10 U/ml LH, 10 U/ml FSH, 1 mM VPA, and optionally 10 ng/ml TGFβ.

The presently disclosed subject matter also provides in some embodiments methods for treating a disease, disorder, and/or an injury to a cell, tissue, or organ in a subject. In some embodiments, the methods comprise administering to the subject a plurality of the presently disclosed ex vivo expanded VSELs in a pharmaceutically acceptable carrier in an amount and via a route sufficient to allow at least a fraction of the ex vivo expanded VSELs to engraft the tissue and differentiate therein, whereby the disease, disorder, and/or injury is treated. In some embodiments, the subject is a mammal, optionally a human. In some embodiments, the plurality of the ex vivo expanded VSELs are derived from VSELs that are autologous to the subject. In some embodiments, the pharmaceutically acceptable carrier is pharmaceutically acceptable for use in a human.

The presently disclosed subject matter also provides in some embodiments methods for repopulating cell types in subjects. In some embodiments, the methods comprise administering to the subject a composition comprising a plurality of the presently disclosed ex vivo expanded VSELs in a pharmaceutically acceptable carrier in an amount and via a route sufficient to allow at least a fraction of the ex vivo expanded VSELs to engraft a target site and differentiate therein, whereby a cell type is repopulated in the subject. In some embodiments. the cell type is a hematopoietic cell. In some embodiments, the target site comprises the bone marrow. In some embodiments, the subject is a mammal, optionally a human. In some embodiments, the plurality of the ex vivo expanded VSELs are derived from VSELs that are autologous to the subject. In some embodiments, the plurality of ex vivo expanded VSELs are derived from VSELs isolated from cord blood. In some embodiments, the pharmaceutically acceptable carrier is pharmaceutically acceptable for use in a human.

The presently disclosed subject matter also provides in some embodiments methods for bone marrow transplantation. In some embodiments, the methods comprise administering to a subject with at least partially absent bone marrow a pharmaceutical preparation comprising an effective amount of ex vivo expanded VSELs produced by the presently disclosed methods, wherein the effective amount comprises an amount of ex vivo expanded VSELs sufficient to engraft in the bone marrow of the subject. In some embodiments, the subject with at least partially absent bone marrow has undergone a pre-treatment to at least partially reduce the bone marrow in the subject. In some embodiments, the pre-treatment comprises a myeloreductive or a myeloablative treatment. In some embodiments, the pre-treatment comprises administering to the subject an immunotherapy, a chemotherapy, a radiation therapy, or a combination thereof. In some embodiments, the radiation therapy comprises total body irradiation. In some embodiments, the administering comprises intravenous administration of the pharmaceutical preparation. In some embodiments, the subject is a mammal, optionally a human. In some embodiments, the plurality of the ex vivo expanded VSELs are derived from VSELs that are autologous to the subject.

The presently disclosed subject matter also provides in some embodiments methods for treating radiation exposure in subjects. In some embodiments, the methods comprise administering a therapeutically effective amount of ex vivo expanded VSELs produced by the presently disclosed methods to the subject. In some embodiments, the radiation exposure comprises acute radiation syndrome, hematopoietic syndrome, gastrointestinal syndrome, neurovascular syndrome, or any combination thereof. In some embodiments, the ex vivo expanded VSELs are autologous to the subject. In some embodiments, the ex vivo expanded VSELs are allogeneic to the subject. In some embodiments, the subject is a human.

Thus, it is an object of the presently disclosed subject matter to provide methods for ex vivo expansion of VSELs.

An object of the presently disclosed subject matter having been stated hereinabove, and which is achieved in whole or in part by the presently disclosed subject matter, other objects will become evident as the description proceeds when taken in connection with the accompanying Figures as best described herein below.

BRIEF DESCRIPTION OF THE FIGURES

FIG. 3A shows freshly sorted VSELs, with the right panel being a magnified version of the field indicated in the left panel. In FIG. 3B, the two upper panels show VSELs in culture as they proliferated, wherein after 2 months of ex vivo expansion, many small cells as well as some larger cells were observed. The lower three panels show cells aspirated from the cultures. The left and middle panel are light microscope images and the right panel shows intravital staining of cells aspirated from the ex vivo expansion with the dye Hoechst 33342. The white line in the lower left corner of certain panels corresponds to 10 µm.

DETAILED DESCRIPTION

I. General Considerations

Figure 1A:
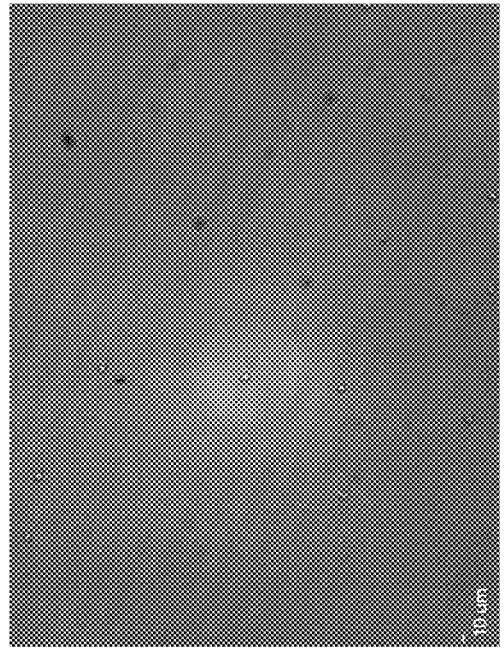
FIGS. 1A-1D are photomicrographs of cultures of murine Sca1$^+$/lin$^-$/CD45$^-$VSELs at day 0 (FIG. 1A), at day 16 (FIG. 1B), at day 28 (FIG. 1C), and two months (FIG. 1D) of culture in DMEM culture medium containing 5% fetal bovine serum (FBS) supplemented with 10 U/ml luteinizing hormone (LH), 10 U/ml follicle-stimulating hormone (FSH), and 1.25 mM valproic acid (VPA) in a humidified incubator maintained at 37° C. with 5% $CO_2$. The white line in the lower left corner of each panel corresponds to 10 µm.
Figure 1B:
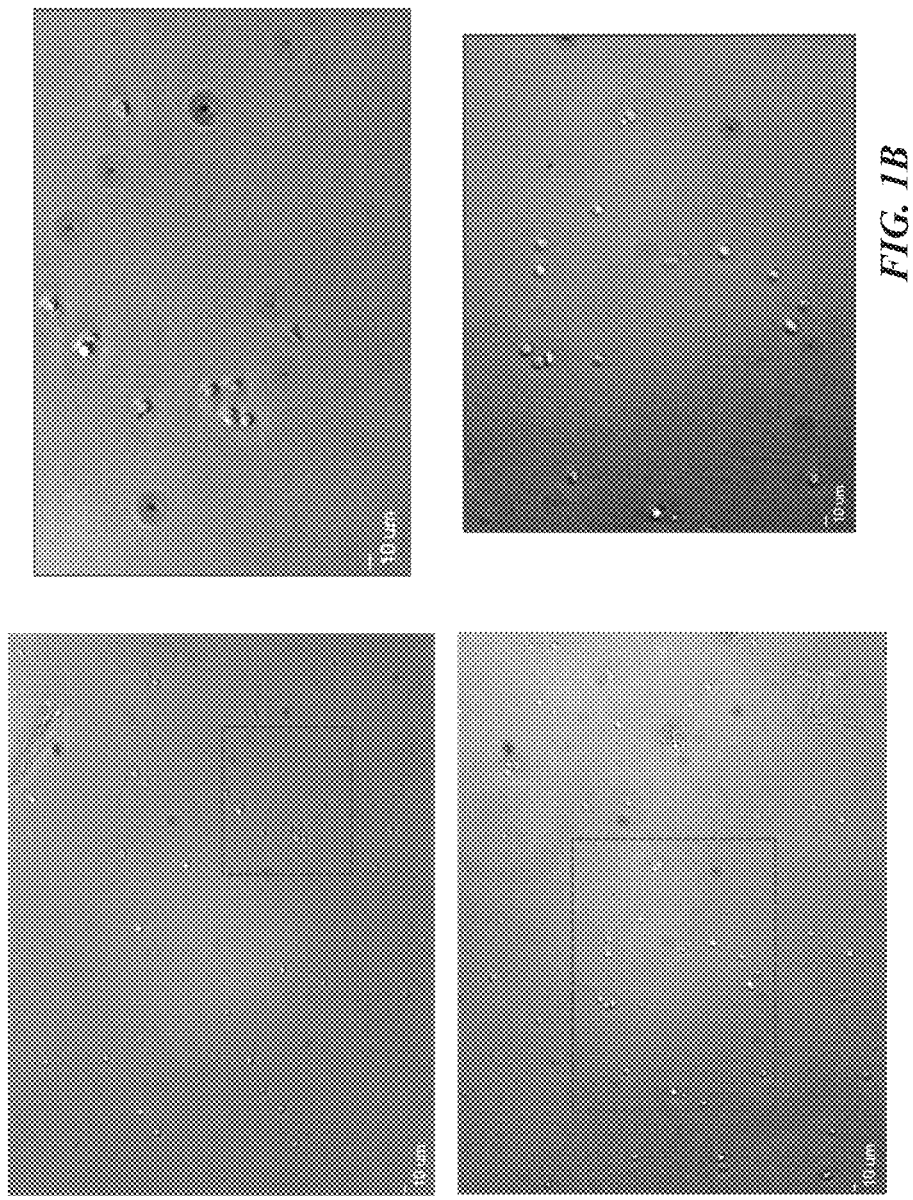
Figure 1C:
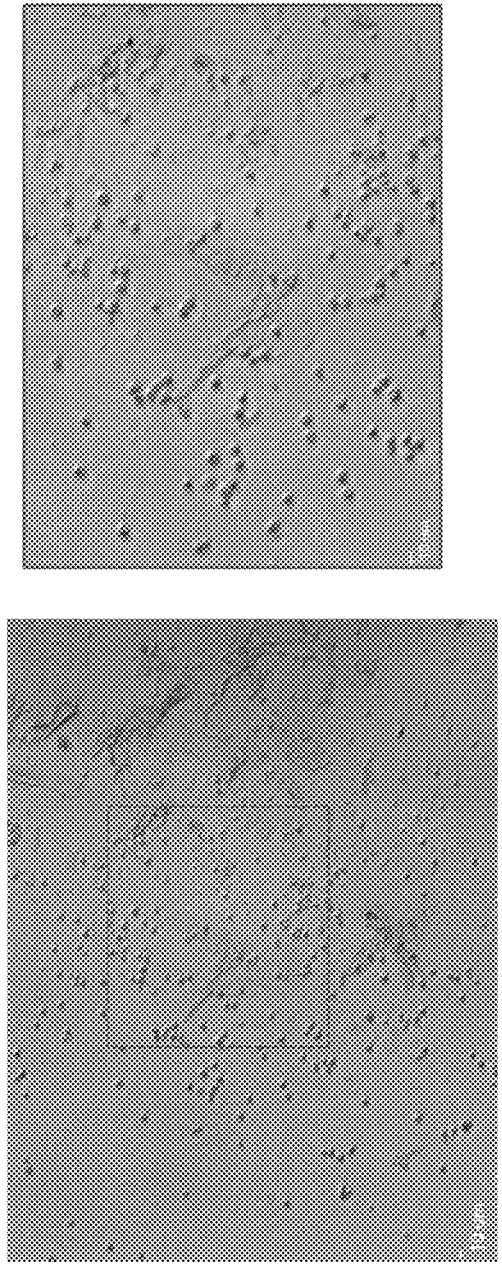
Figure 1D:
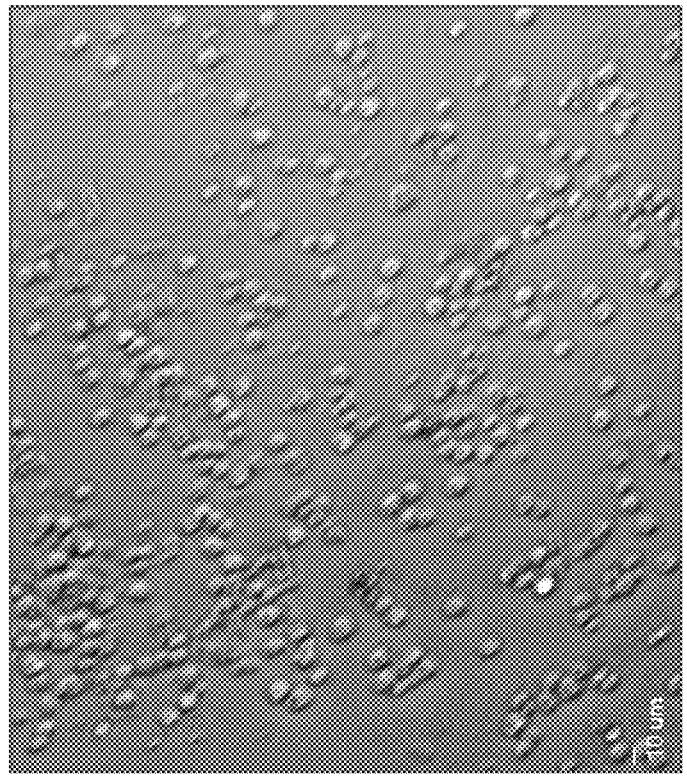
Figure 1D:
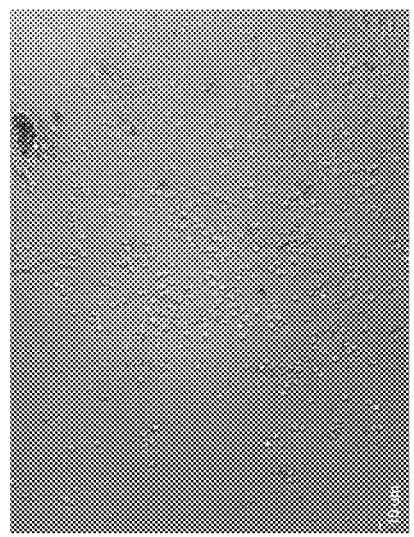
Figure 2A:
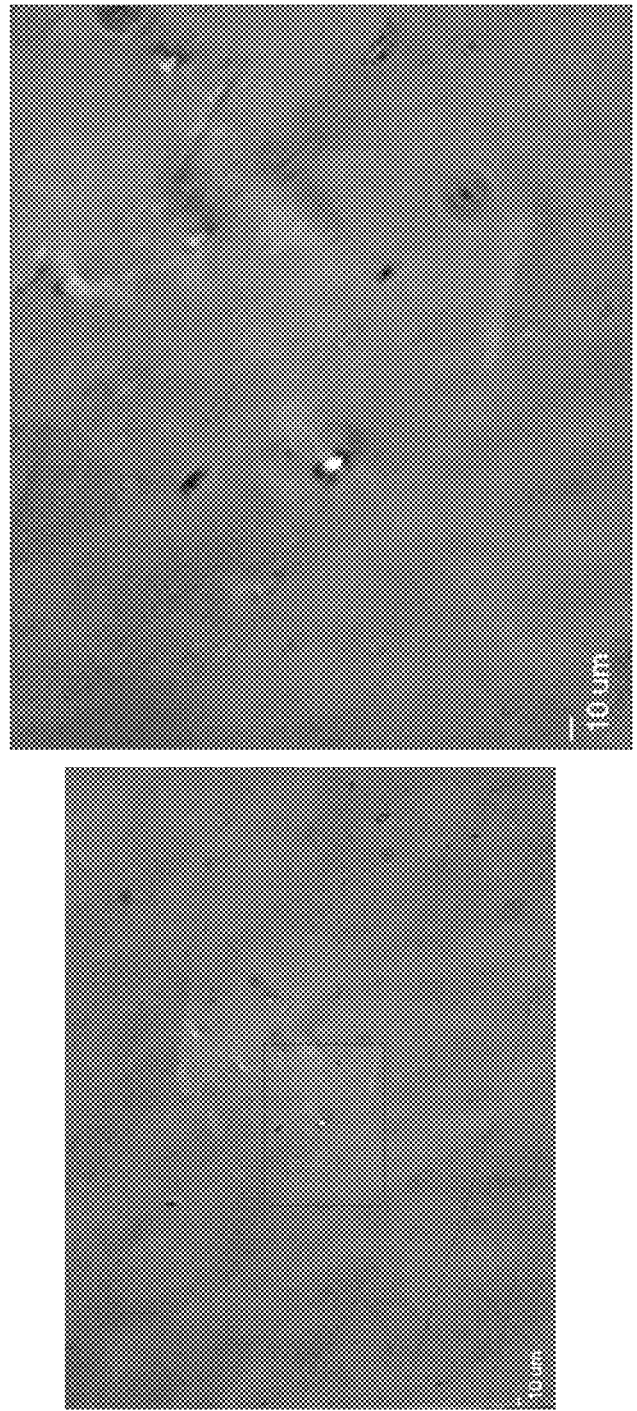
FIGS. 2A-2D are photomicrographs of cultures of human cord blood-derived CD133+/lin$^-$/CD45$^-$ VSELs at day 0 (FIG. 2A), at day 12 (FIG. 2B), at one month (FIG. 3C), and two months (FIG. 2D) of culture in D-MEM medium supplemented with 10% FBS in the presence of VPA (1 mM), LH (10 U/ml), FSH (10 U/ml) and transforming growth factor beta (TGFβ; 10 ng/ml). The white line in the lower left corner of each panel corresponds to 10 µm.
Figure 2B:
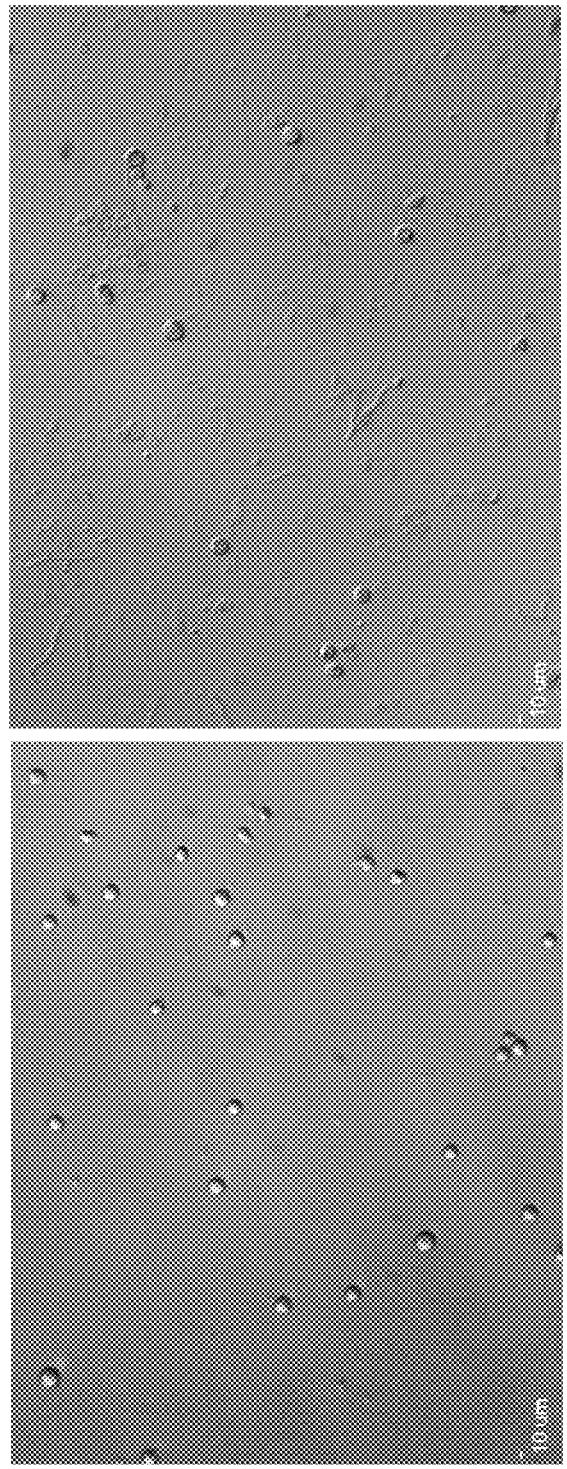
Figure 2C:
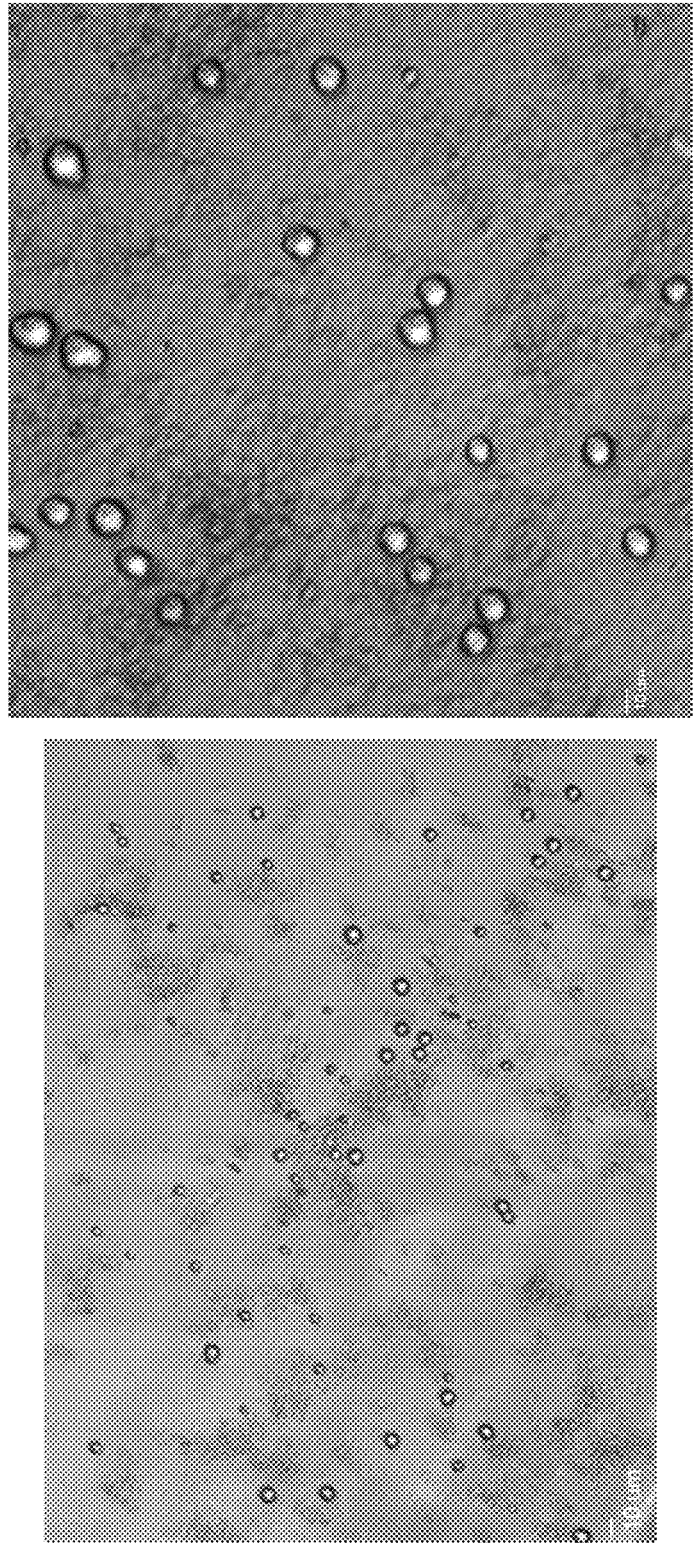
Figure 2D:
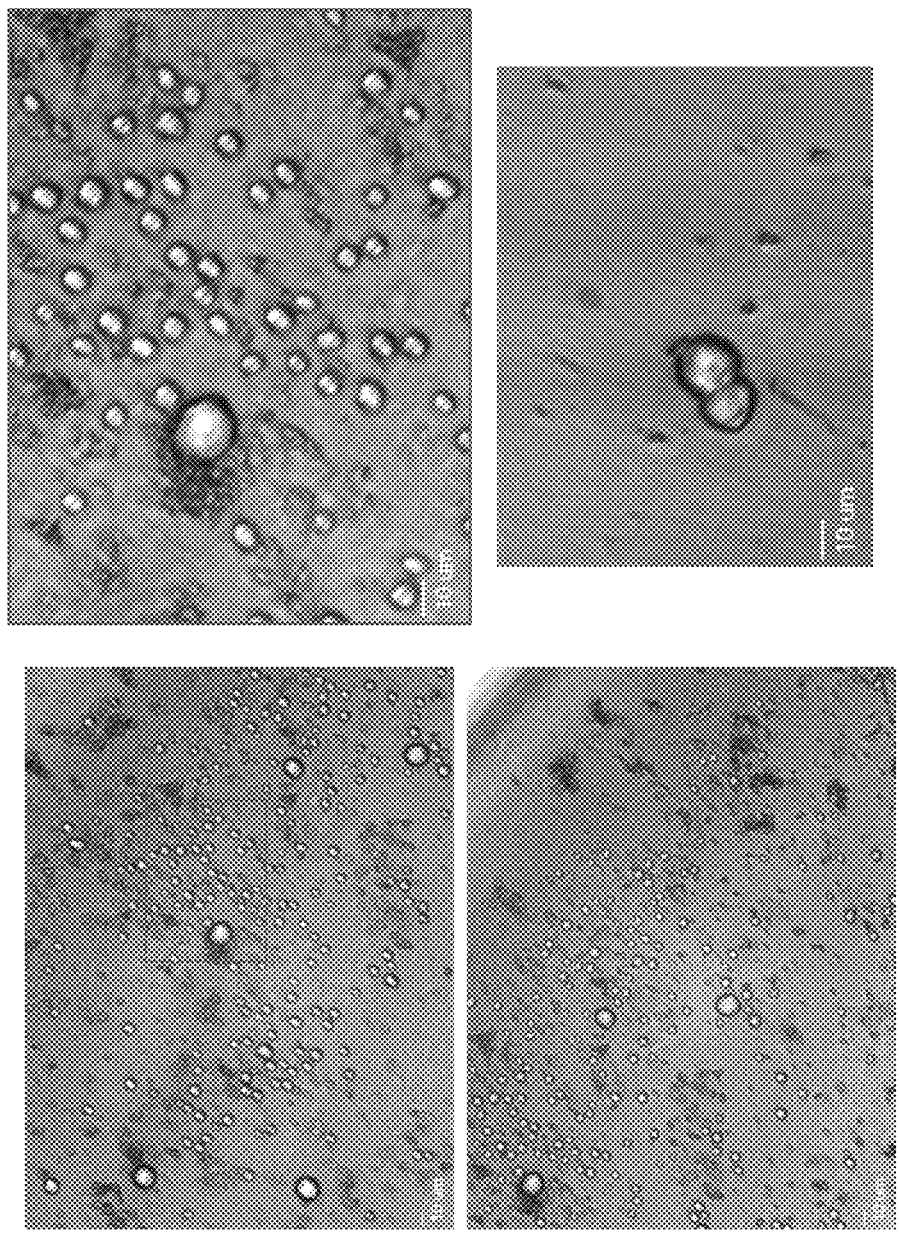

Genomic imprinting is an epigenetic process responsible for mono-allelic expression of the so-called imprinted genes (Reik & Walter, 2001). There are at least 80 imprinted genes (i.e., expressed from maternal or paternal chromosomes only) that have been identified for which mono-allelic expression appears to be relevant to proper development (Yamazaki et al., 2003; Pannetier & Feil, 2007; Horii et al., 2008). In addition, most imprinted genes such as insulin-like growth factor 2 (Igf2), H19, Igf2 receptor (Igf2R), and p57Kip2 (also known as Cdkn1c) have a direct role in embryo development (Reik & Walter, 2001).

The majority of imprinted genes exist as gene clusters enriched for CpG islands and their expression is coordinately regulated by DNA methylation status on CpG-rich cis elements known as differentially methylated regions (DMRs). The DMRs are differentially methylated on CpG sites by DNA methyltransferases (DNMTs), depending on the parental allele origin (Delaval & Feil, 2004). In addition, depending on the developmental period of methylation, "primary DMRs" are differentially methylated during gametogenesis, and "secondary DMRs" acquire allele-specific methylation after fertilization (Lopes et al., 2003). So far, 15 primary DMRs have been identified in the mouse genome. Interestingly, most DMRs are methylated in the maternal allele and only three DMRs (Igf2-H19, Rasgrf1, Meg3 loci) are paternally methylated (Kobayashi et al., 2006). Although DMR methylation is of primary importance, histone modifications also contribute to monoallelic expression of these genes (Fournier et al., 2002; Mager et al., 2003.

VSELs are cells that were identified in adult bone marrow (BM; see PCT International Patent Application Publication Nos. WO 2007/067280 and 2009/059032, the entire disclosures of which are incorporated herein by reference). They are: (i) are very small in size (about 3-6 μm); (ii) are positive for Oct-4, CXCR4, SSEA-1, and Sca-1; (iii) are CD45 negative and lineage negative; iv) possess large nuclei containing unorganized chromatin (euchromatin); and v) form embryoid body-like spheres (VSEL-DSs) that contain primitive stem cells that are capable of differentiating into cell types derived from all three germ layers when co-cultured with C2C12 cells. VSELs do not reveal hematopoietic activity immediately after isolation, but acquire hematopoietic potential similar to stem cells from established embryonic stem (ES) cell lines and induced pluripotent stem (iPS) cells following co-culture/activation over OP9 stroma (see U.S. Patent Application Publication No. 2012/0114614; Ratajczak et al., 2011).

Unlike ES cells, highly purified BM-derived Oct4" VSELs do not proliferate in vitro if cultured alone, and do not grow teratomas in vivo. In co-cultures with myoblastic C2C12 cells, VSELs form embryoid body- (EB) like structures, referred to herein as VSEL-derived spheres (VSEL-DSs), which contain primitive stem cells able to differentiate into cells from all three germ layers (Kucia et al., 2006. On the one hand, this suggests that VSELs are a quiescent cell population and that mechanisms must exist to prevent their unleashed proliferation and teratoma formation. On the other hand, the ability of VSELs to change their quiescent fate in co-cultures with C2C12 cells shows that their quiescent status can be modulated. Similarly, during formation of spheres in culture, VSELs modulate expression of imprinted genes to resemble the pattern that is characteristic for somatic cells (see Shin et al., 2009), supporting the idea that VSELs can contribute to rejuvenation of organs and tissue repair.

II. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims, unless the context clearly indicates differently. For example, the phrase "a cell" refers to one or more cells, including a plurality of cells in, for example, a tissue or organ, including the entire tissue or organ. Similarly, the phrase "an antibody" refers to one or more antibodies, including a plurality of the same antibody. The phrase "at least one", when employed herein to refer to an entity, can refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100. In some embodiments, whole number values in excess of 100; 1000; 10,000; 100,000; 1,000,000; or greater are also encompassed.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent present in the pharmaceutical composition. It is noted, however, that carriers, excipients, and other inactive agents can and likely would be present in pharmaceutical compositions that consist essentially of a pharmaceutically active agent or a plurality of pharmaceutically active agents.

With respect to the terms "comprising", "consisting of", and "consisting essentially of", where one of these three terms is used herein, the presently disclosed and claimed subject matter can include the use of either of the other two terms. By way of example and not limitation, a pharmaceutical composition that in some embodiments comprises one or more active agents can also in some embodiments consists essentially of one or more active agents, and can also in some embodiments consist of one or more active agents.

The term "about", as used herein when referring to a measurable value such as an amount of weight, time, dose, etc., is meant to encompass variations of in some embodiments ±20%, in some embodiments±10%, in some embodiments±5%, in some embodiments±1%, and in some embodiments±0.1% from the specified amount, as such variations are appropriate to perform the disclosed methods.

As used herein, the phrase "acceptable for use in a human" refers to a composition (including but not limited to a pharmaceutical composition) or a component thereof (such as but not limited to a carrier, excipient, or other ingredient) that is recognized as being safe for human use and that is present in the composition in an amount that is recognized as being safe for human use. The phrase also takes into account the human subject's medical status, the disease, disorder, and/or condition to be treated, the amount of the composition or component thereof that is to be administered to the human subject, the route of administration, etc. As such, and by way of example and not limitation, the precise composition of a pharmaceutically acceptable carrier that is acceptable for use in a human can vary provided that it would be consistent with medical treatment guidelines in view of the desired use.

As used herein, the phrase "acute radiation syndrome" (also referred to as radiation poisoning, radiation sickness, or radiation toxicity) is a collection of symptoms that are present within about 24 hours after exposure of a subject to high amounts of ionizing radiation (such as, but not limited to a whole body dose of 100 rads of X-radiation). Exposure to such radiation results in damage to DNA and other structures within cells in various tissues, leading to cellular degradation. The DNA damage also results in impairment of cellular division, which in some embodiments leads to one or more of the symptoms associated with acute radiation syndrome. By way of example and not limitation, some of the consequences of acute radiation syndrome include damage to the hematopoietic, gastrointestinal, and/or immune systems. Larger doses of radiation can also result in neurological effects or even death.

As used herein, the term "allogeneic" when used in the context of a cell or plurality of cells refers to cells that are derived from (e.g., isolated from) different individuals who are not genetically identical. The term "allogeneic" can also be used in the context of donors and recipients, and in this context refers to donor/recipient pairs wherein the donor and the recipient are not the same individual. In some embodiments, allogeneic cells and/or donor/recipient pairs nonetheless share one or more histocompatibility antigens (e.g., human HLA) such that the cells and/or donor/recipient pairs would be considered a sufficient histocompatibility "match" for transplantation purposes. In some embodiments, allogeneic cells and/or donor/recipient pairs share all histocompatibility antigens (e.g., human HLA) such that the cells and/or donor/recipient pairs would be considered a "perfect match" for transplantation purposes. In such embodiments, the allogeneic cells and/or donor/recipient pairs are in some embodiments referred to as "haploidentical".

As used herein, the phrase "a subject with at least partially absent bone marrow" refers to a subject who, as a result of some treatment or other phenomenon has reduced bone marrow. In some embodiments, the subject has at least partially absent bone marrow as a result of exposure to radiation. In some embodiments, the subject has at least partially absent bone marrow as a result of an intentional administration of some myeloreductive or a myeloablative treatment designed to create space in the bone marrow for engraftment of one or more cells such as, but not limited to stem cells. Exemplary such treatments include, but are not limited to immunotherapy, chemotherapy, radiation therapy, or any combination thereof. In some embodiments, the myeloreductive or myeloablative treatment comprises total body irradiation.

As used herein, the term "autologous" when used in the context of a cell or plurality of cells refers to cells that are derived from (e.g., isolated from) the same individual or from a genetically indistinct individual. The term "autologous" can also be used in the context of donors and recipients, and in this context refers to donors and recipients who are the same individual or individuals who are not genetically distinct. In some embodiments, autologous cells are cells that are isolated from different individuals who are substantially genetically identical, including but not limited to identical twins or different members of the same genetic line (e.g., an inbred line or strain of any given species). Synonyms for autologous include "isogeneic", "isogenic", and "syngeneic".

As used herein, the term "derivative" refers to a compound, composition, or molecule that is modified from an original starting material compound, composition, or molecule. By way of example and not limitation, a derivative of an antibody is a molecule that retains some or all of the primary, secondary, tertiary, or quaternary structure of a starting material antibody, but that includes one or more additional modifications beyond being just a fragment of the starting material antibody. Exemplary non-limiting antibody derivatives include antibodies or fragments thereof that have been labeled (i.e., detectably labeled), complexed with other moieties, or otherwise modified such as by artificial affinity maturation.

The phrase "derived from" is in some embodiments synonymous with the phrase "isolated from". Thus, in some embodiments cells and/or other molecules that are "derived from" a given source refers to the fact that the cells can be isolated from that source. For example, a cell or other molecule that is derived from a particular donor refers to the fact that the cell or the other molecule was isolated from that particular donor.

The phrase "derived from" can also refer to the fact that the cell or other molecule is a progeny of and/or a modified version of an original cell or other molecule. By way of example and not limitation, the phrase "ex vivo expanded VSELs are derived from VSELs that are autologous to the subject" refers to the fact that the "ex vivo expanded VSELs" are progeny of VSELs that are autologous to the subject. By way of further example and not limitation, the ex vivo expanded VSELs of the presently disclosed subject matter are expanded in culture from one or more initial VSELs by asymmetric and/or symmetric divisional of the one or more initial VSELs such that each such ex vivo expanded VSEL is a daughter cell of one or more of the initial cultured VSELs and/or is a daughter cell of a subsequent generation (e.g., granddaughter cell, great-granddaughter cell, etc.) of one or more of the initial cultured VSELs. As such, it is understood that a cell that is "derived from" a given cell is any cell that can trace its ancestry back to the given cell by cellular division. It is further understood that at any point along the cellular division pathway between the initial cell and the cell derived therefrom, one or more of the intervening cells can be manipulated such as but not limited to by transformation, transduction, electroporation, or other recombinant techniques that introduce into intervening cell(s) a biological material (such as but not limited to a nucleic acid, a protein, etc.). Thus, a recombinant or transgenic version of a given cell is still considered to be derived from said cell provided that it can trace at least a part of its ancestry to said cell.

In a related context, pluralities of cells that include cell types that are "derived from all three germ layers" refer to pluralities of cells (e.g., an embryoid body or embryoid body-like structure) that comprise cell types that during normal development are characterized as being of ectodermal, endodermal, and mesodermal origin.

As used herein, the term "donor" refers to an organism (including but not limited to a human) from whom a cell, tissue, organ, or other biological material has been isolated. It is not required that the cell, tissue, organ, or other biological material that has been isolated actually be administered in whole or in part to a second organism (which in the case of autologous donors can be the same organism) in order for the first organism to be considered a donor, although typically a donor is part of a donor/recipient pair. In some embodiments, donors and recipients can be autologous, and in some embodiments donors and recipients can be allogenic or allogeneic.

As used herein, the phrase "effective amount" refers to an amount of a compound, composition, etc. that under a given set of circumstances is sufficient to provide a desired effect. In some embodiments, an "effective amount" is a "therapeutically effective amount", which refers to an amount of a compound, composition, etc. that under a given set of circumstances is sufficient to provide a desired therapeutic effect. Thus, in some embodiments a "therapeutically effective amount" is an amount of a compound, composition, etc., that is sufficient to produce a measurable biological response. Actual dosage levels of active ingredients in a composition of the presently disclosed subject matter can be varied so as to administer an amount of the active agent(s) present therein that is effective to achieve the desired therapeutic response for a particular subject. The selected dosage level will depend upon a variety of factors including the activity of the composition, the formulation, the route of administration, combination(s) with other drugs or treatments, and the physical condition and prior medical history of the subject being treated. Determination and adjustment of a therapeutically effective doses, as well as evaluation of when and how to make such adjustments, are known to those of ordinary skill in the art of medicine.

As used herein, the term "engineer" and grammatical variants thereof refers to artificial modifications of the compositions of the presently disclosed subject matter and their components. In some embodiments, a VSEL may be engineered to comprise one or more biomolecules (e.g., a nucleic acid) that was not present in the VSELs prior to them being engineered. Thus, in such embodiments, "engineering" encompasses modifications of cells such as by transduction, transfection, or transformation of said cells with one or more nucleic acids, polypeptides, small molecules, etc.

As used herein, the term "engraft" refers to when a cell or a plurality of cells that are introduced and/or administered to a subject become resident in and/or otherwise occupy a tissue or other structure in the subject and, in some embodiments, initiate one or more biological activities therein. By way of example and not limitation, the ex vivo expanded VSELs of the presently disclosed subject matter in some embodiments engraft a tissue including, but not limited to bone marrow, and differentiate therein, whereby a disease, disorder, and/or injury is treated.

As used herein, the phrase "feeder cell-free" refers to cell cultures that do not comprise feeder cells such as, but not limited to fibroblasts or other cells that are intentionally added to a cell culture in order to assist with the growth and/or maintenance of a cell type of interest.

As used herein, the phrase "gastrointestinal syndrome" refers to a set of symptoms and effects characterized by gastrointestinal dysfunction subsequent to radiation exposure to the stomach and/or intestines. Symptoms of gastrointestinal syndrome include nausea, vomiting, loss of appetite, and abdominal pain. In some embodiments, gastrointestinal syndrome is associated with death.

As used herein, the phrase "HDAC inhibitor" refers to a molecule that reduces a biological activity of a histone deacetylase (HDAC) gene product. Exemplary HDAC inhibitors include but are not limited to valproic acid (VPA), nicotinic acid, and nicotinamide (NAM). In some embodiments, an HDAC inhibitor is an inhibitor of a sirtuin biological activity, optionally an inhibitory nucleic acid that hybridizes to a member of the sirtuin (Sirt) family of mono-ADP-ribosyltransferases or deacylases. Exemplary an HDAC inhibitor is an siRNAs that are directed against a human SIRT, such as but not limited to a human SIRT that is encoded by a nucleic acid as set forth in any of GEN-BANK® Accession Nos. NM 012238 (SEQ ID NO: 1), NM_001142498 (SEQ ID NO: 3), and NM_001314049 (SEQ ID NO: 5). In some embodiments, an HDAC inhibitor is a microRNA selected from the group consisting of an miR-34 microRNA, optionally an miR-34a microRNA (e.g., SEQ ID NOs: 7-10); an miR-449 microRNA, optionally an miR-449a, miR-449b, or miR-449c microRNA (e.g., SEQ ID NOs: 11-19); and an miR-200 microRNA, optionally an miR-200a, miR-200b, or miR-200c microRNA (e.g., SEQ ID NOs: 20-28).

As used herein, the phrase "hematopoietic cell" refers to any cell of the hematopoietic lineage. Exemplary hematopoietic cells include red blood cells, white blood cells, platelets, and their precursors including but not limited to those stem cells that give rise to cells of the lymphoid and/or myeloid lineages (including but not limited to T cells, B cells, natural killer (NK) cells, monocytes, macrophages, neutrophils, basophils, eosinophils, erythrocytes, dendritic cells, megakaryocytes, platelets).

As used herein, the phrase "hematopoietic syndrome" refers to a set of symptoms and effects characterized by hematopoietic dysfunction subsequent to radiation exposure. Hematopoietic syndrome is characterized by a drop in blood cells that results in anemia, decreased ability to fight infection, and reduced clotting/increased risk of bleeding.

The terms "heterologous", "recombinant", and "exogenous", when used herein to refer to a nucleic acid sequence (e.g., a DNA sequence and/or an RNA sequence) or a gene, refer to a sequence that originates from a source foreign to the particular host cell or, if from the same source, is modified from its original form and/or is isolated from its original genomic location. Thus, a heterologous gene in a host cell includes a gene that is endogenous to the particular host cell but has been modified with respect to its primary sequence and/or is located in a non-naturally-occurring genomic location. The terms also include non-naturally occurring multiple copies of a naturally occurring DNA sequence. Thus, the terms refer to a nucleic acid segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA and/or RNA segments can be expressed to yield exogenous polypeptides.

The phrase "hybridize" and grammatical variants thereof refer to an ability of a first nucleic acid molecule and a target nucleic acid molecule to form a sufficient number of intermolecular hydrogen bonds between their nucleotides to remain together as an at least partially double stranded molecule under the conditions in which the hybridization occurs (e.g., intracellularly in a VSEL or a derivative thereof) in order to modulate a biological activity of the target nucleic acid molecule. In some embodiments, an inhibitory nucleic acid hybridizes to a member of the sirtuin (Sirt) family of mono-ADP-ribosyltransferases or deacylases in order to inhibit a biological activity of the Sirt family member.

The phrase "inhibitory nucleic acid" refers to any nucleic acid molecule capable of mediating RNA interference (RNAi) or gene silencing. See e.g., Bass, 2001; Elbashir et al., 2001b; and PCT International Publication Nos. WO 99/07409, WO 99/32619, WO 2000/01846, WO 2000/44895, WO 2000/44914, WO 2001/29058, and WO 2001/36646. Exemplary inhibitory nucleic acids include antisense polynucleotides, small interfering RNAs/short interfering RNAs (siRNAs), small hairpin RNAs (shRNAs), and microRNAs (miRNAs). In some embodiments, the inhibitory nucleic acid is a microRNA selected from the group consisting of an miR-34 microRNA, optionally an miR-34a microRNA (e.g., SEQ ID NOs: 7-20); an miR-449 microRNA, optionally an miR-449a, miR-449b, or miR-449c microRNA (e.g., SEQ ID NOs: 11-19); and an miR-200 microRNA, optionally an miR-200a, miR-200b, or miR-200c microRNA (e.g., SEQ ID NOs: 20-28). The use of miRNAs and microRNAs in RNAi and gene silencing is disclosed in, for example, U.S. Pat. No. 8,273,866 to McSwiggen et al. and the references cited therein, all of which are incorporated herein by reference in their entireties.

Thus, in some embodiments, the presently disclosed subject matter takes advantage of the ability of short, double stranded RNA molecules to cause the down regulation of cellular genes via RNA interference. As used herein, "RNA interference" (RNAi) refers to a process of sequence-specific post-transcriptional gene silencing mediated by a small interfering RNA (siRNA). See generally Fire et al., 1998. The process of post-transcriptional gene silencing is thought to be an evolutionarily conserved cellular defense mechanism that has evolved to prevent the expression of foreign genes (Fire, 1999).

In some embodiments, the inhibitory nucleic acid is an siRNA that comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., 2001a).

RNAi has been described in several cell types and organisms. Fire et al. described RNAi in *C. elegans* (Fire et al., 1998). Wianny & Zernicka-Goetz disclose RNAi mediated by dsRNA in mouse embryos (Wianny & Zernicka-Goetz, 1999). Hammond et al. were able to induce RNAi in *Drosophila* cells by transfecting dsRNA into these cells (Hammond et al., 2000). They demonstrated the presence of RNAi in cultured mammalian cells including human embryonic kidney and HeLa cells by the introduction of duplexes of synthetic 21 nucleotide RNAs (Elbashir et al., 2001b).

Other studies have indicated that a 5'-phosphate on the target-complementary strand of a siRNA duplex facilitate siRNA activity and that ATP is utilized to maintain the 5'-phosphate moiety on the siRNA (Nykanen et al., 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 2000/44914 and WO 2001/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT International Publication Nos. WO 2001/75164 (in vitro RNAi system using cells from *Drosophila* and the use of specific siRNA molecules for certain functional genomic and certain therapeutic applications); WO 2001/36646 (methods for inhibiting the expression of particular genes in mammalian cells using dsRNA molecules); WO 99/32619 (methods for introducing dsRNA molecules into cells for use in inhibiting gene expression); WO 2001/92513 (methods for mediating gene suppression by using factors that enhance RNAi); WO 2002/044321 (synthetic siRNA constructs); WO 2000/63364 and WO 2001/04313 (methods and compositions for inhibiting the function of polynucleotide sequences); and WO 2002/055692 and WO 2002/055693 (methods for inhibiting gene expression using RNAi), each of which are incorporated herein by reference in their entireties.

In some embodiments, the presently disclosed subject matter utilizes RNAi to at least partially inhibit expression of a sirtuin, optionally a human sirtuin. Inhibition is preferably at least about 10% of normal expression amounts. In some embodiments, the method comprises contacting a target cell with an antisense polynucleotide in an amount sufficient to inhibit expression of a sirtuin. In some embodiments, the target cell is present in a subject, and the RNA is introduced into the subject.

The RNA can have a double-stranded region comprising a first strand comprising a ribonucleotide sequence that corresponds to the coding strand of the gene encoding the target protein (e.g., SIRT) and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases.

One skilled in the art will recognize that any number of suitable common techniques can be used to introduce the RNAs into a target cell. In some embodiments, a vector encoding the RNA is introduced to the target cell. For example, the vector encoding the RNA can be transfected into the target cell and the RNA is then transcribed by cellular polymerases.

The term "isolated", as used in the context of a nucleic acid, polypeptide (including, for example, a peptide), or a cell (including, for example, a VSEL stem cell), indicates that the nucleic acid, polypeptide, or cell exists apart from its native environment. An isolated nucleic acid, polypeptide, or cell can exist in a purified form or can exist in a non-native environment.

As used herein, the phrase "maintained in the cell culture" refers to an ability of a cell to continue to exist viably in the cell culture without losing a desired biological characteristic and/or function. By way of example and not limitation, the phrase "VSELs and/or the expanded VSELs are maintained in the cell culture for at least about two months" means that the VSELs and/or the expanded VSELs are capable of being cultured in vitro in a cell culture for at least about two months without dying or otherwise losing one or more desirable characteristics and/or biological activities of the VSELs and/or expanded VSELs. In some embodiments, the presently disclosed subject matter relates to maintaining VSELs and/or expanded VSELs in culture for about two months without the VSELs and/or expanded VSELs losing the ability to engraft a target tissue when administered to a subject.

As used herein, the term "modulate" refers to a change in the expression level of a gene, or a level of RNA molecule or equivalent RNA molecules encoding one or more proteins or protein subunits, or activity of one or more proteins or protein subunits is upregulated or downregulated, such that expression, level, and/or activity is greater than or less than that observed in the absence of the modulator. For example, the term "modulate" can mean "inhibit" or "suppress", but the use of the word "modulate" is not limited to this definition.

In some embodiments, the terms "inhibit", "suppress", "downregulate", and grammatical variants thereof refer to a biological activity of a polypeptide (e.g., a sirtuin polypeptide) or other biomolecule that is lower in the presence of a modulator than that which occurs in the absence of the modulator. For example, a modulator can inhibit a biological activity of a sirtuin polypeptide to interact with its target(s). This can be accomplished by any mechanism, including but not limited to enhancing its existence in an inactive form and/or by enhancing the rate of its degradation.

As used herein, the phrase "myeloreductive or a myeloablative treatment" refers to a treatment that is designed to at least partially and in some embodiments completely reduce at least one cellular component of the bone marrow. Exemplary myeloreductive or myeloablative treatments comprise treatment with an immunotherapy, a chemotherapy, a radiation therapy, or a combination thereof.

As used herein, the phrase "neurovascular syndrome" refers to a collection of symptoms and/or conditions that result from exposure of the brain to high levels of radiation. Symptoms typically include headache, cognition deficits, and neurological problems, which can lead to a loss of consciousness and death.

The terms "nucleic acid molecule" and "nucleic acid" refer to deoxyribonucleotides, ribonucleotides, and polymers thereof, in single-stranded or double-stranded form. Unless specifically limited, the term encompasses nucleic acids containing known analogues of natural nucleotides that have similar properties as the reference natural nucleic acid. The terms "nucleic acid molecule" and "nucleic acid" can also be used in place of "gene", "cDNA", and "mRNA". Nucleic acids can be synthesized, or can be derived from any biological source, including any organism.

As used herein, the term "quiescence" refers to a state in which a cell that at one point was capable of dividing no longer divides. In terms of cell culture, a quiescent cell is one that no longer divides under cell culture conditions that otherwise might have support cellular division and/or does not divide when placed in culture. It is recognized that as cells differentiate they become more and more quiescent. VSELs, for example, are also quiescent unless and until they receive a signal to divide. When placed in ordinary cell culture, VSELs typically remain quiescent. However, as disclosed herein, certain cell culture conditions have been identified that allow the VSELs to overcome their quiescence and as a result, be expanded in vitro.

As used herein, a cell exists in a "purified form" when it has been isolated away from all other cells that exist in its native environment, but also when the proportion of that cell in a mixture of cells is greater than would be found in its native environment. Stated another way, a cell is considered to be in "purified form" when the population of cells in question represents an enriched population of the cell of interest, even if other cells and cell types are also present in the enriched population. A cell can be considered in purified form when it comprises in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

As used herein, the term "recipient" refers to a subject to whom a composition of the presently disclosed subject matter is administered. In some embodiments a recipient can be autologous with respect to his or her donor(s), and in some embodiments a recipient can be allogenic or allogeneic with respect to his or her donor(s).

As used herein, the phrase "re-establishing imprinting" refers to changes that occur in the imprinting status of one or more loci in a cell when the cell is grown in culture. In some embodiments, "re-establishing imprinting" refers to changes in the imprinting status of one or more loci in a VSEL or a derivative/progeny cell thereof that occurs when the VSEL or a derivative/progeny cell thereof is grown under the culture conditions set forth herein.

As used herein, the phrase "repopulating a cell type" refers to a method for introducing one or more cells into a subject or a tissue and/or compartment thereof by a route and under conditions sufficient for the at least a subset of the one or more cells introduced to engraft the tissue and/or the compartment and divide and/or differentiate therein. By way of example and not limitation, one or more bone marrow cell types can be repopulated by administering VSELs and/or their progeny into the bone marrow such that the VSELs and/or their progeny differentiate into various hematological lineages. In this example, VSELs and/or their progeny can thus be employed in bone marrow transplantation in order to repopulate one or more hematopoietic linages.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), *Amphibia* (amphibians), Reptilia (reptiles), *Aves* (birds), and Mammalia (mammals)), and all Orders and Families encompassed therein.

Similarly, all genes, gene names, and gene products disclosed herein are intended to correspond to orthologs and/or homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes listed in Tables 1 and 2, which disclose Accession Nos. for the murine and human nucleic acid sequences in the GEN-BANK® biosequence database, respectively, are intended to encompass homologous genes and gene products from other animals including, but not limited to other mammals, fish, amphibians, reptiles, and birds.

Also similarly, the gene symbols disclosed herein are intended to correspond to orthologs and/or homologs from any species for which the compositions and methods disclosed herein are applicable. As such, although human gene symbols are typically presented in all uppercase letters (e.g., SIRT, PTPRC, ALDH, etc.) and gene symbols for other species are presented with the first letter in uppercase and subsequent letters in lowercase (e.g., Sirt, Ptprc, Aldh, etc.) it is understood that when a gene symbol is presented in all uppercase or mixed uppercase and lowercase letters, this disclosure is intended to be exemplary only and is not to be interpreted as a limitation with respect to a species unless the context in which it appears clearly indicates a particular species.

The methods of the presently disclosed subject matter are particularly useful for warm-blooded vertebrates. Thus, the presently disclosed subject matter concerns mammals and birds. More particularly contemplated is the isolation, manipulation, and use of VSEL stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also contemplated is the isolation, manipulation, and use of VSEL stem cells from livestock, including but not limited to domesticated swine (pigs and hogs), ruminants, horses, poultry, and the like.

As used herein, the phrases "target site", "target tissue", and the like refer to a site and/or a tissue in a subject in which VSELs and/or their progeny are intended to collect. Target sites can thus be sites where the VSELs and/or their progeny are directly administered or can be sites where the VSELs and/or their progeny are intended to home in order to collect. An exemplary target site is the bone marrow when hematopoietic reconstitution is desired, the heart when cardiac cell replacement is desired, the retina when retinal cell replacement is desired, etc.

As used herein, the phrase "total body irradiation" (TBI) refers to radiation given in such a way as to cover the entire body of a subject. Generally, TBI is performed prior to bone marrow transplantation to suppress a subject's immune system in order to decrease host versus graft immune reactions and/or to destroy abnormal cells (e.g., tumor and/or cancer cells) that are refractory to other treatments. Doses of TBI that are appropriate for various purposes and various subjects are known to those of skill.

As used herein, the phrase "therapeutic agent" refers to an agent that is used to, for example, treat, inhibit, prevent, mitigate the effects of, reduce the severity of, reduce the likelihood of developing, slow the progression of, and/or cure, a disease, or disorder.

As used herein, the term "transduction" refers to the introduction of a foreign nucleic acid into a cell using a vector, in some embodiments a viral vector.

As used herein, the term "transfection" as used herein refers to the introduction of a foreign nucleic acid into a cell using recombinant DNA technology. The term "transformation" means the introduction of a "foreign" (i.e., extrinsic or exogenous) gene, DNA, or RNA sequence to a host cell, such that the host cell will express the introduced gene or sequence to produce a desired substance, such as a protein or enzyme, coded by the introduced gene or sequence. The introduced gene or sequence can also be called a "cloned", "foreign", or "heterologous" gene or sequence or a "transgene", and can include regulatory and/or control sequences, such as start, stop, promoter, signal, secretion, or other sequences used by a cell's genetic machinery. The gene or sequence can include nonfunctional sequences or sequences with no known function. A host cell that receives and expresses introduced DNA or RNA has been "transformed" and is a "transformant" or a "clone", and is "transgenic". The DNA or RNA introduced to a host cell can come from any source, including cells of the same genus or species as the host cell, or cells of a different genus or species The terms "treating", "treatment", "treat", and grammatical variants thereof as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented.

As such, the terms "treating", "treatment", "treat", and grammatical variants thereof refer to an intervention in which one or more undesirable symptoms and/or consequences of a disease, disorder, or condition are reduced or eliminated. It is noted that in some embodiments a treatment is only partially effective in reducing such a symptom, and it is understood that it is not required that the treatment fully eliminate the symptoms or all related symptoms. In the context of "an injury to a tissue", a treatment can comprise administering to a subject a plurality of ex vivo expanded VSELs or a composition comprising the same (e.g., a plurality of ex vivo expanded VSELs in a pharmaceutically acceptable carrier) in an amount and via a route sufficient to allow at least a fraction of the ex vivo expanded VSELs to engraft the tissue and differentiate therein, whereby the injury to the tissue is treated (i.e., one or more undesirable consequences of the injury to the tissue are reduced or eliminated). Similarly, the phrase "treating radiation exposure" refers to an intervention in which one or more undesirable symptoms or consequences of radiation exposure are reduced or eliminated. It is understood that a treatment as set forth herein can result from a VSEL and/or a derivative or progeny cell thereof engrafting into a tissue or other site and differentiating therein to provide a cell type that is missing or for which a biological activity is insufficiently present, the engraftment of a VSEL and/or a derivative or progeny cell thereof into a particular tissue or site can provide a treatment via paracrine effects of the VSEL and/or a derivative or progeny cell thereof per se. As such, as used herein, the term "treatment" and grammatical variants thereof encompass the reduction or elimination of one or more undesirable symptoms and/or consequences of a disease, disorder, or condition by providing a cell type of interest and/or any other biological activity that the VSEL and/or a derivative or progeny cell thereof provides to a subject.

As used herein, the phrase "very small embryonic like stem cell", the abbreviation "VSEL", and grammatical variations thereof refer to a rare population of pluripotent stem cells. In some embodiments, the VSEL stem cells ("VSELs") are human VSELs and are characterized as $Lin^-$, $CD45^-$, and $CD34^+$. In some embodiments, the VSELs are human VSELs and are characterized as $Lin^-$, $CD45^-$, and $CD133^+$. In some embodiments, the VSELs are human VSELs and are characterized as $Lin^-$, $CD45^-$, and $CXCR4^+$. In some embodiments, the VSELs are human VSELs and are characterized as $Lin^-$, $CD45^-$, $CXCR4^+$, $CD133^+$, and $CD34^+$. In some embodiments, the VSELs are human VSELs and are characterized as $Lin^-$, $CD45^-$, $CD133^+$, and $CD34^+$. In some embodiments, human VSELs express at least one of SSEA-4, Oct-4, Rex-1, and Nanog. With respect to stem cell markers, mouse VSELs express in some embodiments at least one of SSEA-1, Oct-4, Rex-1, and Nanog. VSELs can also be characterized as possessing large nuclei surrounded by a narrow rim of cytoplasm, and contain embryonic-type unorganized euchromatin. VSELS also have high telomerase activity. In some embodiments, the VSELs are human VSELs and can characterized as $Lin^-$, $CD45^-$, $CXCR4^+$, $CD133^+$, $Oct\ 4^+$, $SSEA4^+$, and $CD34^+$. In some embodiments, the human VSELs can be less primitive and can be characterized as $Lin^-$, $CD45^-$, $CXCR4^+$, $CD133^+$, and $CD34^+$. In some embodiments, the human VSELs can be enriched for pluripotent embryonic transcription factors, such as but not limited to OCT-4, SOX2, and NANOG. Human VSELs have a diameter of in some embodiments 4-5 μm, in some embodiments 4-6 μm, in some embodiments 4-7 μm, in some embodiments 5-6 μm, 5-8 in some embodiments μm, in some embodiments 6-9 μm, and in some embodiments 7-10 μm. VSELs administered according to the presently disclosed subject matter can in some embodiments be collected and enriched or purified and used directly, or in some embodiments frozen for later use. In some embodiments, the VSELs can be expanded ex vivo as set forth herein prior to administration or freezing. Autologous or allogeneic VSELs can be administered according to the presently disclosed subject matter. Further, the VSELs may be engineered to comprise one or more biomolecules (e.g., a nucleic acid) that was not present in the VSELs prior to them being engineered.

III. Methods for Isolating VSELs from Sources Expected to Contain VSELs

Methods for isolating VSELs from sources expected to contain VSELs have been described in, for example, U.S. Patent Application Publication Nos. 2009/0155225, 2009/0220466, 2010/0267107, 2012/0114614, and 2014/0154219, the disclosure of each of which is incorporated herein by reference in its entirety. In some embodiments, the methods comprise isolating a plurality of $CD45^{neg}/lin^{neg}$ cells that are $Sca-1^+$ or $CD34^+$ from a source expected to comprise VSELs. In some embodiments, the methods can further comprise fractionating the cells to identify cells that are $Oct-4^+$, $CXCR4^+$, and/or $SSEA-1^+$. In some embodiments, the methods can further comprise fractionating the cells into subpopulations that are $ALDH^{high}$ or $ALDH^{low}$.

As used herein, the term "CD45" refers to a tyrosine phosphatase, also known as the leukocyte common antigen (LCA), and having the gene symbol PTPRC. This gene corresponds to GENBANK® Accession Nos. NP_002829 (human), NP_035340 (mouse), NP_612516 (rat), XP_002829 (dog), XP_599431 (cow), and AAR16420 (pig). The amino acid sequences of additional CD45 homologs are also present in the GENBANK® database, including those from several fish species and several non-human primates.

As used herein, the term "CD34" refers to a cell surface marker found on certain hematopoietic and non-hematopoietic stem cells, and having the gene symbol CD34. The GENBANK® database discloses amino acid and nucleic acid sequences of CD34 from humans (e.g., AAB25223), mice (NP_598415), rats (XP_223083), cats (NP_001009318), pigs (NP_999251), cows (NP_776434), and others.

In mice, some stem cells also express the stem cell antigen Sca-1 (GENBANK® Accession No. NP_034868), also referred to as Lymphocyte antigen Ly-6A.2.

Thus, the subpopulation of $CD45^{neg}$ stem cells represents a subpopulation of all $CD45^{neg}$ cells that are present in the population of cells prior to the separating step. In some embodiments, the cells of the subpopulation of $CD45^{neg}$ stem cells are from a human, and are $CD34^+/lin^{neg}/CD45^{neg}$. In some embodiments, the cells of the subpopulation of $CD45^{neg}$ stem cells are from a mouse, and are $Sca-1^+/lin^{neg}/CD45^{neg}$.

In some embodiments, a different set of markers can be employed for isolating VSELs. As set forth in U.S. Patent Application Publication No. 2014/0154219, a subpopulation of $CD45^{neg}$ stem cells can also be further fractionated with respect to expression of GlyA, CD133, and ALDH. Thus, in some embodiments a VSEL subpopulation is a $CD45^{neg}/GlyA^{neg}/CD133^+/ALDH^{high}$ subpopulation, a $CD45^{neg}/GlyA^{neg}/CD133^+/ALDH^{low}$ subpopulation, a $CD45^{neg}/Lin^{neg}/SSEA-4^+/ALDH^{high}$ subpopulation, a $CD45^{neg}/Lin^{neg}/SSEA-4/ALDH^{low}$ subpopulation, or any combination thereof.

The isolation of the disclosed subpopulations can be performed using any methodology that can separate cells based on expression or lack of expression of the one or more of the CD45, CXCR4, CD34, CD133, Sca-1, CD45R/B220, Gr-1, TCRαβ, TCRγδ, CD11b, Ter-119, GlyA, ALDH, SSEA-1, and SSEA-4 markers including, but not limited to fluorescence-activated cell sorting (FACS).

As used herein, "$lin^{neg}$" and "lineage-negative" refer to a cell that does not express any of the following lineage markers: CD45R/B220, Gr-1, TCRαβ, TCRγδ, CD11b, and Ter-119. These lineage markers are found on cells of the B cell lineage from early Pro-B to mature B cells (CD45R/B220); cells of the myeloid lineage such as monocytes during development in the bone marrow, bone marrow granulocytes, and peripheral neutrophils (Gr-1); thymocytes, peripheral T cells, and intestinal intraepithelial lymphocytes (TCRαβ and TCRγδ); myeloid cells, NK cells, some activated lymphocytes, macrophages, granulocytes, B1 cells, and a subset of dendritic cells (CD11b); and mature erythrocytes and erythroid precursor cells (Ter-119).

The separation step can be performed in a stepwise manner as a series of steps or concurrently. For example, the presence or absence of each marker can be assessed individually, producing two subpopulations at each step based on whether the individual marker is present. Thereafter, the subpopulation of interest can be selected and further divided based on the presence or absence of the next marker.

Alternatively, the subpopulation can be generated by separating out only those cells that have a particular marker profile, wherein the phrase "marker profile" refers to a summary of the presence or absence of two or more markers. For example, a mixed population of cells can contain both $CD34^+$ and $CD34^{neg}$ cells. Similarly, the same mixed population of cells can contain both $CD45^+$ and $CD45^{neg}$ cells. Thus, certain of these cells will be $CD34^+/CD45^+$, others will be $CD34^+/CD45^{neg}$, others will be $CD34^{neg}/CD45^+$, and others will be $CD34^{neg}/CD45^{neg}$. Each of these individual combinations of markers represents a different marker profile. As additional markers are added, the profiles can become more complex and correspond to a smaller and smaller percentage of the original mixed population of cells. In some embodiments, the cells of the presently disclosed subject matter have a marker profile of $CD34^+/lin^{neg}/CD45^{neg}$, and in some embodiments, the cells of the presently disclosed subject matter have a marker profile of $Sca-1^+/lin^{neg}/CD45^{neg}$.

In some embodiments of the presently disclosed subject matter, antibodies specific for markers expressed by a cell type of interest (e.g., polypeptides expressed on the surface of a $CD34^+/lin^{neg}/CD45^{neg}$ or a $Sca-1^+/lin^{neg}/CD45^{neg}$ cell) are employed for isolation and/or purification of subpopulations of BM cells that have marker profiles of interest. It is understood that based on the marker profile of interest, the antibodies can be used to positively or negatively select fractions of a population, which in some embodiments are then further fractionated.

In some embodiments, a plurality of antibodies, antibody derivatives, and/or antibody fragments with different specificities is employed. In some embodiments, each antibody, or fragment or derivative thereof, is specific for a marker selected from the group including but not limited to Ly-6A/E (Sca-1), CD34, CXCR4, CD133, CD45, CD45R, B220, Gr-1, TCRαβ, TCRγδ, CD11b, Ter-119, SSEA-4, GlyA, ALDH, c-met, LIF-R, SSEA-1, Oct-4, Rev-1, and Nanog. In some embodiments, cells that express one or more genes selected from the group including but not limited to SSEA-1, Oct-4, Rev-1, and Nanog are isolated and/or purified.

The presently disclosed subject matter relates to a population of cells that in some embodiments express the following antigens: CXCR4, CD133, CD34, SSEA-1 (mouse) or SSEA-4 (human), fetal alkaline phosphatase (AP), c-met, and the LIF-Receptor (LIF-R). In some embodiments, the cells of the presently disclosed subject matter do not express the following antigens: CD45, Lineage markers (i.e., the cells are $lin^{neg}$), HLA-DR, MHC class I, CD90, CD29, and CD105. Thus, in some embodiments the cells of the presently disclosed subject matter can be characterized as follows: $CXCR4^+/CD133^+/CD34^+/SSEA-1^+$ (mouse) or $SSEA-4^+$ (human)/$AP^+/c-met^+/LIF-R^+/CD45^{neg}/lin^{neg}/HLA-DR^{neg}/MHC$ class $I^{neg}/CD90^{neg}/CD29^{neg}/CD105^{neg}$.

In some embodiments, each antibody, or fragment or derivative thereof, comprises a detectable label. Different antibodies, or fragments or derivatives thereof, which bind to different markers can comprise different detectable labels or can employ the same detectable label.

A variety of detectable labels are known to the skilled artisan, as are methods for conjugating the detectable labels to biomolecules such as antibodies and fragments and/or derivatives thereof. As used herein, the phrase "detectable label" refers to any moiety that can be added to an antibody, or a fragment or derivative thereof, that allows for the detection of the antibody. Representative detectable moieties include, but are not limited to, covalently attached chromophores, fluorescent moieties, enzymes, antigens, groups with specific reactivity, chemiluminescent moieties, and electrochemically detectable moieties, etc. In some embodiments, the antibodies are biotinylated. In some embodiments, the biotinylated antibodies are detected using a secondary antibody that comprises an avidin or streptavidin group and is also conjugated to a fluorescent label including, but not limited to Cy3, Cy5, and Cy7. In some embodiments, the antibody, fragment, or derivative thereof is directly labeled with a fluorescent label such as Cy3, Cy5, or Cy7. In some embodiments, the antibodies comprise biotin-conjugated rat anti-mouse Ly-6A/E (Sca-1; clone E13-161.7), streptavidin-PE-Cy5 conjugate, anti-CD45-APCCy7 (clone 30-F11), anti-CD45R/B220-PE (clone RA3-6B2), anti-Gr-1-PE (clone RB6-8C5), anti-TCRαβ PE (clone H57-597), anti-TCRγδ PE (clone GL3), anti-CD11b PE (clone M1/70) and anti-Ter-119 PE (clone TER-119). In some embodiments, the antibody, fragment, or derivative thereof is directly labeled with a fluorescent label and cells that bind to the antibody are separated by fluorescence-activated cell sorting. Additional detection strategies are known to the skilled artisan.

While FACS scanning is a convenient method for purifying subpopulations of cells, it is understood that other methods can also be employed. An exemplary method that can be used is to employ antibodies that specifically bind to one or more of CD45, CXCR4, CD34, CD133, Sca-1, CD45R/B220, Gr-1, TCRαβ, TCRγδ, CD11b, and Ter-119, with the antibodies comprising a moiety (e.g., biotin) for which a high affinity binding reagent is available (e.g., avidin or streptavidin). For example, a biotin moiety could be attached to antibodies for each marker for which the presence on the cell surface is desirable (e.g., CD34, Sca-1, CXCR4), and the cell population with bound antibodies could be contacted with an affinity reagent comprising an avidin or streptavidin moiety (e.g., a column comprising avidin or streptavidin). Those cells that bound to the column would be recovered and further fractionated as desired. Alternatively, the antibodies that bind to markers present on those cells in the population that are to be removed (e.g., CD45R/B220, Gr-1, TCRαβ, TCRγδ, CD11b, and Ter-119) can be labeled with biotin, and the cells that do not bind to the affinity reagent can be recovered and purified further.

It is also understood that different separation techniques (e.g., affinity purification and FACS) can be employed together at one or more steps of the purification process.

A population of cells containing the CD34$^+$/lin$^{neg}$/CD45$^{neg}$ or Sca-1$^+$/lin$^{neg}$/CD45$^{neg}$ cells of the presently disclosed subject matter can be isolated from any subject or from any source within a subject that contains them. In some embodiments, the population of cells comprises a bone marrow sample, a cord blood sample, or a peripheral blood sample. In some embodiments, the population of cells is isolated from peripheral blood of a subject subsequent to treating the subject with an amount of a mobilizing agent sufficient to mobilize the CD45$^{neg}$ stem cells from bone marrow into the peripheral blood of the subject. As used herein, the phrase "mobilizing agent" refers to a compound (e.g., a peptide, polypeptide, small molecule, or other agent) that when administered to a subject results in the mobilization of a VSEL stem cell or a derivative thereof from the bone marrow of the subject to the peripheral blood. Stated another way, administration of a mobilizing agent to a subject results in the presence in the subject's peripheral blood of an increased number of VSEL stem cells and/or VSEL stem cell derivatives than were present therein immediately prior to the administration of the mobilizing agent. It is understood, however, that the effect of the mobilizing agent need not be instantaneous, and typically involves a lag time during which the mobilizing agent acts on a tissue or cell type in the subject in order to produce its effect. In some embodiments, the mobilizing agent comprises at least one of granulocyte-colony stimulating factor (G-CSF) and a CXCR4 antagonist (e.g., a T140 peptide; Tamamura et al., 1998).

In some embodiments, a VSEL stem cell or derivative thereof including but not limited to a daughter cell derived therefrom also expresses a marker selected from the group including but not limited to c-met, c-kit, LIF-R, and combinations thereof. In some embodiments, a VSEL stem cell or derivative thereof including but not limited to a daughter cell derived therefrom expresses a receptor for one or more androgens and/or estrogens including but not limited to the receptors for FSH, LH, and progesterone (PRG), and combinations thereof. In some embodiments, a VSEL stem cell or derivative thereof including but not limited to a daughter cell derived therefrom expresses an erythropoietin (EPO) receptor. In some embodiments, the VSEL stem cell or derivative thereof also expresses SSEA-1, Oct-4, Rev-1, and Nanog, and in some embodiments, the disclosed isolation methods further comprise isolating those cells that express these genes.

In some embodiments, the disclosed isolation methods further comprise isolating those cells that are c-met$^+$, c-kit$^+$, and/or LIF-R$^+$. In some embodiments, the disclosed isolation methods further comprise isolating those cells that express receptors for one or more androgens and/or estrogens including but not limited to the receptors for FSH, LH, and PRG. In some embodiments, the disclosed isolation methods further comprise isolating those cells that express an erythropoietin receptor. In some embodiments, the disclosed isolation methods further comprise isolating those cells that are SSEA-1$^+$, Oct-4$^+$, Rev-1$^+$, and/or Nanog$^+$.

The presently disclosed subject matter also provides a population of CD45$^{neg}$ stem cells isolated by the presently disclosed methods.

IV. Methods for Ex Vivo Expansion of and/or Overcoming Quiescence in VSELs

The presently disclosed subject matter also provides in some embodiments methods for ex vivo expansion of and/or overcoming quiescence in VSELs.

As used herein, the phrase "ex vivo expansion" refers to a process by which VSELs are grown in culture under conditions sufficient to expand their numbers while substantially maintaining their status as VSELs. By way of example and not limitation, the ex vivo expansion methods disclosed herein result in some embodiments in a two-fold expansion of VSEL numbers, in some embodiments in a three-fold expansion of VSEL numbers, in some embodiments in a four-fold expansion of VSEL numbers, in some embodiments in a five-fold expansion of VSEL numbers, in some embodiments in a ten-fold expansion of VSEL numbers, and in some embodiments in a greater than ten-fold expansion of VSEL numbers at some pre-selected time. The pre-selected time can be any time after which a sufficient expansion has occurred given the purpose(s) for which the expanded VSELs are desired. Thus, the pre-selected time can be in some embodiments one week, in some embodiments two weeks, in some embodiments three weeks, in some embodiments four weeks, in some embodiments six weeks, in some embodiments one week, and in some embodiments greater than two months.

Conditions under which VSELs can be expanded ex vivo are disclosed herein. Basic conditions include culture in a cell culture vessel in a culture medium that comprises a histone deacetylase (HDAC) inhibitor and one or more hormones and/or growth factors in an amount sufficient to overcome VSELs quiescence, thereby allowing the VSELs to divide. In some embodiments, the culture conditions are such that the VSELs are expanded without undergoing differentiation during the culturing. In some embodiments, the VSELs are grown in the absence of any feeder cells, although growth on non-cellular matrices is contemplated by the instant disclosure.

As used herein, the phrases "histone deacetylase (HDAC) inhibitor" and "HDAC inhibitor" refer to a molecule that inhibits a biological activity of the enzyme histone deacetylase (HDAC) either directly or indirectly. As is well-known, HDACs are a class of enzymes that remove acetyl groups from ε-N-acetyl lysine amino acids present in histones, thereby modifying the interactions between histones and DNA. The interactions between DNA and histones have been implicated in the regulation of DNA expression, and HDAC inhibitors have entered the clinic as anti-neoplastic agents. In some aspects of their biological activities, HDAC inhibitors bind to sirtuins (SIRT) that chaperone DNA methyltransferase 3-Like (DNMT3L), liberating DNMT3L. DNMT3L liberated from complexes can direct DNMT3A and DNMT3B to methylate parentally erased genes in VSELs (e.g., Igf2-H19 locus), thereby modifying the parental imprinting status of these genes.

Several small molecule HDAC inhibitors have been investigated as anti-cancer agents. These include N-Hydroxy-N'-phenyloctanediamide (also known as suberanilohydroxamic acid (SAHA) and Vorinostat), (1S,4S,7Z,10S,16E,21R)-7-ethylidene-4,21-diisopropyl-2-oxa-12,13-dithia-5,8,20,23-tetrazabicyclo[8.7.6]tricos-16-ene-3,6,9,19,22-pentone (also known as Romidepsin or Istodax), (2E)-N-hydroxy-3-[4-({[2-(2-methyl-1/-indol-3-yl)ethyl]amino}methyl)phenyl]acrylamide (also known as LBH-589, Farydak, or Panobinostat), and (2E)-N-Hydroxy-3-[3-(phenylsulfamoyl)phenyl]prop-2-enamide (also known as PXD101, Beleodaq, and Belinostat). Another small molecule HDAC inhibitor is valproic acid (VPA), which is currently used to for both psychiatric and neurological indications. Other HDAC inhibitors include nicotinic acid and its derivatives (including but not limited to nicotinamide), as well as derivatives of NAD, dihydrocoumarin, naphthopyranone, and 2-hydroxynaphthaldehydes (see Porcu et al., 2005; see also U.S. Patent Application Publication No. 2007/0043050).

Another class of HDAC inhibitors includes inhibitory RNAs that target HDAC gene products. By way of example and not limitation, an inhibitory nucleic acid that targets HDAC gene products include the miR-34 family of microRNAs, such as but not limited to the miR-34a microRNAs; the miR-449 family of microRNAs, such as but not limited to the miR-449a, miR-449b, and miR449c microRNAs; and the miR-200 family of microRNAs, such as but not limited to the miR-200a, miR-200b, and miR-200c microRNAs. Exemplary microRNAs that can function a HDAC inhibitors are summarized in Table 1 below.

In some embodiments, the culture conditions employ a growth medium supplement comprising serum, a serum fraction, and/or a serum replacement. Exemplary, non-limiting growth medium supplements include bovine serum, fetal bovine serum, fractions thereof, and serum replacements compositions available from Sigma-Aldrich Co., ThermoFischer Scientific, and other suppliers.

TABLE 1

Exemplary microRNA HDAC Inhibitors

| miRNA Name | Species | GENBANK ® Accession No. |
|---|---|---|
| miR-34a | Human | NR_029610.1 (SEQ ID NO: 7) |
|  | Mouse | NR_029751.1 (SEQ ID NO: 8) |
|  | Rat | NR_031850.1 (SEQ ID NO: 9) |
|  | Dog | NR_049328.1 (SEQ ID NO: 10) |

TABLE 1-continued

Exemplary microRNA HDAC Inhibitors

| miRNA Name | Species | GENBANK ® Accession No. |
|---|---|---|
| miR-449a | Human | NR_029960.1 (SEQ ID NO: 11) |
|  | Mouse | NR_029961.1 (SEQ ID NO: 12) |
|  | Rat | NR_031950.1 (SEQ ID NO: 13) |
|  | Dog | NR_049215.1 (SEQ ID NO: 14) |
| miR-449b | Human | NR_030387.1 (SEQ ID NO: 15) |
|  | Mouse | NR_030602.1 (SEQ ID NO: 16) |
|  | Dog | NR_128867.1 (SEQ ID NO: 17) |
| miR-449c | Human | NR_031572.1 (SEQ ID NO: 18) |
|  | Mouse | NR_030452.1 (SEQ ID NO: 19) |
| miR-200a | Human | NR_029834.1 (SEQ ID NO: 20) |
|  | Mouse | NR_029723.1 (SEQ ID NO: 21) |
|  | Rat | NR_031916.1 (SEQ ID NO: 22) |
| miR-200b | Human | NR_029639.1 (SEQ ID NO: 23) |
|  | Mouse | NR_029587.1 (SEQ ID NO: 24) |
|  | Rat | NR_031917.1 (SEQ ID NO: 25) |
| miR-200c | Human | NR_029779.1 (SEQ ID NO: 26) |
|  | Mouse | NR_029792.1 (SEQ ID NO: 27) |
|  | Rat | NR_031915.1 (SEQ ID NO: 28) |

In some embodiments, the culture medium has been supplemented with a hormone and/or a growth factor. As disclosed herein, culturing VSELs in a culture medium supplemented with luteinizing hormone (LH), follicle-stimulating hormone (FSH), and optionally transforming growth factor beta (TGFβ), can result in overcoming VSELs quiescence to thereby enhance ex vivo expansion.

Accordingly, in some embodiments the presently disclosed subject matter provides methods for ex vivo expansion of very small embryonic like stem cells (VSELs). In some embodiments, the VSELs are cultured in the absence of feeder cells. In some embodiments, the methods comprise providing a plurality of VSELs; and growing the VSELs in a culture medium that comprises a histone deacetylase (HDAC) inhibitor, luteinizing hormone (LH), follicle-stimulating hormone (FSH), and optionally transforming growth factor beta (TGFβ), wherein the culture medium comprises an effective amount of the HDAC inhibitor, LH, FSH, and optionally TGFβ to overcome quiescence of the VSELs, resulting in expansion of the VSELs. In some embodiments, the HDAC inhibitor is selected from the group consisting of valproic acid (VPA), nicotinic acid, and nicotinamide (NAM). In some embodiments, the HDAC inhibitor is an inhibitor of a sirtuin biological activity, optionally an inhibitory nucleic acid that hybridizes to a member of the sirtuin (SIR) family of mono-ADP-ribosyltransferases or deacylases. In some embodiments, the inhibitory nucleic acid that hybridizes to the member of the SIR family comprises an siRNA that is directed against a human SIR, optionally a human SIR that is encoded by a nucleic acid as set forth in any of GENBANK® Accession Nos. NM_012238 (SEQ ID NO: 1), NM_001142498 (SEQ ID NO: 3), and NM_001314049 (SEQ ID NO: 5). In some embodiments, the culture medium comprises about 10 U/ml LH, about 10 U/ml FSH, about 1 mM VPA, and optionally about 10 ng/ml TGFβ.

The presently disclosed subject matter also provides cell cultures, optionally feeder cell-free cell cultures. In some embodiments, the presently disclosed subject matter provides feeder cell-free cell cultures comprising a plurality of VSELs, one or more ex vivo expanded VSELs, and a culture medium. In some embodiments, the culture medium comprises a bovine serum or a serum replacement, a histone deacetylase (HDAC) inhibitor, luteinizing hormone (LH), follicle-stimulating hormone (FSH), and optionally transforming growth factor beta (TGFβ), which together are present in an effective amount to overcome quiescence of the VSELs, resulting in expansion of the VSELs. In some embodiments, the cell culture comprises about 10% fetal bovine serum (FBS), about 10 U/ml LH, about 10 U/ml FSH, about 1 mM VPA, and optionally about 10 ng/ml TGFβ. In some embodiments, the VSELs and/or the expanded VSELs are maintained in the cell culture for at least about two months.

Also provided in some embodiments are ex vivo expanded VSELs produced by the methods disclosed herein, and pharmaceutical compositions comprising the same. In some embodiments, a pharmaceutical composition comprises one or more ex vivo expanded VSELs as disclosed herein and a pharmaceutically acceptable carrier, optionally wherein the pharmaceutically acceptable carrier is acceptable for use in a human. In some embodiments, the pharmaceutical composition comprises about $1 \times 10^5$ ex vivo expanded VSELs/ml to about $1 \times 10^9$ ex vivo expanded VSELs/ml.

The pharmaceutical compositions of the presently disclosed subject matter comprise in some embodiments a composition that includes a carrier, particularly a pharmaceutically acceptable carrier, such as but not limited to a carrier pharmaceutically acceptable in humans. Any suitable pharmaceutical formulation can be used to prepare the pharmaceutical compositions for administration to a subject. For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient. It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The pharmaceutical compositions of the presently disclosed subject matter can be used with additional adjuvants or biological response modifiers including, but not limited to, cytokines and other immunomodulating compounds.

Suitable methods for administration the pharmaceutical compositions of the presently disclosed subject matter include, but are not limited to intravenous administration and delivery directly to a target tissue or organ. In some embodiments, the method of administration encompasses features for regionalized delivery or accumulation of the VSELs present in the pharmaceutical composition at the site in need of treatment. In some embodiments, the pharmaceutical compositions are delivered directly into the tissue or organ to be treated. In some embodiments, selective delivery of the presently disclosed pharmaceutical compositions is accomplished by intravenous injection of the pharmaceutical compositions, where the VSELs present therein home to the target tissue or organ and engraft therein. In some embodiments, the VSELs present in the pharmaceutical compositions described herein home to the target tissue or organ as a result of the production of an SDF-1 gradient produced by the target tissue or organ, which acts as a chemotactic attractant to the VSELs disclosed herein.

An effective dose of a pharmaceutical composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of active ingredients in the pharmaceutical compositions of the presently disclosed subject matter can be varied so as to administer a number of ex vivo expanded VSELs that is effective to achieve the desired therapeutic response for a particular subject. The selected dosage level will depend upon the number of VSELs per unit volume or mass of the presently disclosed pharmaceutical compositions, the route of administration, combination with other drugs or treatments, the severity of the condition being treated, and the condition and prior medical history of the subject being treated. However, it is within the skill of the art to start doses of the pharmaceutical compositions of the presently disclosed subject matter at levels lower than required to achieve the desired therapeutic effect and to gradually increase the dosage until the desired effect is achieved. The potency of a pharmaceutical composition can vary, and therefore a "treatment effective amount" can vary. However, one skilled in the art can readily assess the potency and efficacy of a pharmaceutical composition of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease, disorder, or condition to be treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

V. Methods for Modulating Sirtuin Biological Activities

The presently disclosed subject matter also provides in some embodiments methods for modulating sirtuin biological activities in cells including, but not limited to VSELs. In some embodiments, the methods comprise providing a sirtuin gene product (e.g., a sirtuin mRNA or polypeptide) and/or a cell comprising the same (e.g., a VSEL) for which modulation of one or more sirtuin biological activities is desired, and contacting the sirtuin gene product and/or cell in vivo, ex vivo, and/or in vitro with an HDAC inhibitor. In some embodiments, the sirtuin is a human sirtuin that comprises a nucleic acid as set forth in any of GENBANK® Accession Nos. NM_012238 (SEQ ID NO: 1), NM_001142498 (SEQ ID NO: 3), and NM_001314049 (SEQ ID NO: 5) and/or an amino acid sequence as set forth in any of GENBANK® Accession Nos. NP_036370 (SEQ ID NO: 2), NP_001135970 (SEQ ID NO: 4), and NP_001300978 (SEQ ID NO: 6).

With respect to applications of the presently disclosed methods as applied to ex vivo and/or in vitro modulation in cells, the method steps and reagents set forth herein above with respect to the methods for ex vivo expansion of and/or overcoming quiescence in VSELs can be applied to the instant methods for modulating sirtuin biological activities. As such, the methods can in some embodiments comprise growing the cells in a culture medium that comprises an HDAC inhibitor (such as but not limited to VPA, an inhibitory nucleic acid, etc.), luteinizing hormone (LH), follicle-stimulating hormone (FSH), and optionally transforming growth factor beta (TGFβ), wherein the culture medium comprises an effective amount of the HDAC inhibitor, LH, FSH, and optionally TGFβ to overcome quiescence of the VSELs, resulting in expansion of the VSELs.

With respect to in vivo applications of the instant methods, several HDAC inhibitors have already been employed in vivo for the treatment of cancer. These include Vorinostat, Romidepsin/Istodax, Farydak/Panobinostat, and Beleodaq/Belinostat, and similar approaches can be employed with respect to these compounds for modulating sirtuin biological activities in vivo. VPA has been employed for both psychiatric and neurological indications, and similar approaches can also be employed for modulating sirtuin biological activities with VPA in vivo.

Small molecule inhibitors of HDAC such as but not limited to the miRNAs disclosed herein can also be employed in vivo. Methods for employing miRNAs in vivo are disclosed in, for example, U.S. Pat. Nos. 9,181,544 and 9,205,100, both of which are incorporated by reference herein.

VI. Methods for Treating Injuries, Repopulating Cell Types, Bone Marrow Transplantation, and/or Treating Radiation Exposure in Subjects In some embodiments, the presently disclosed subject matter provides that the ex vivo VSELs disclosed herein can be employed for treating injuries, for repopulating cell types, for bone marrow transplantation, and/or for treating radiation exposure in subjects. In these various embodiments the method generally comprise providing a subject in need of such a treatment, and administering to the subject a plurality of the ex vivo expanded VSELs disclosed herein in an amount and via a route sufficient to allow at least a fraction of the ex vivo expanded VSELs to engraft a target site such as but not limited to a tissue or an organ and differentiate therein, whereby an injury is treated and/or a cell type is repopulated. In some embodiments, the subject is a mammal, optionally a human. In some embodiments, the pharmaceutically acceptable carrier is pharmaceutically acceptable for use in a human.

In some embodiments of the presently disclosed methods, the ex vivo expanded VSELs are derived from VSELs that are autologous to the subject. In some embodiments, the ex vivo expanded VSELs are derived from VSELs that are allogeneic to the subject. In some embodiments, the plurality of ex vivo expanded VSELs are derived from VSELs isolated from cord blood.

In the case of bone marrow transplantation, in some embodiments the subject has or has been treated so that he or she has at least partially absent bone marrow. In some embodiments, the subject has undergone a pre-treatment to at least partially reduce the bone marrow in the subject, which in some embodiments can comprise a myeloreductive or a myeloablative treatment. In some embodiments, the pre-treatment comprises administering to the subject an immunotherapy, a chemotherapy, a radiation therapy (optionally comprising total body irradiation), or a combination thereof.

With respect to methods for treating radiation exposure, the presently disclosed method can be applied to subjects with acute radiation syndrome, hematopoietic syndrome, gastrointestinal syndrome, neurovascular syndrome, or any combination thereof.

VI.A. Formulations

The compositions of the presently disclosed subject matter comprise in some embodiments a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, cytokines and other immunomodulating compounds.

VI.B. Administration

Suitable methods for administration of the cells and/or compositions of the presently disclosed subject matter include, but are not limited to intravenous administration and delivery directly to the target tissue or organ. Exemplary routes of administration include parenteral, enteral, intravenous, intraarterial, intracardiac, intrapericardial, intraosseal, intracutaneous, subcutaneous, intradermal, subdermal, transdermal, intrathecal, intramuscular, intraperitoneal, intrasternal, parenchymatous, oral, sublingual, buccal, rectal, vaginal, inhalational, and intranasal. The selection of a particular route of administration can be made based at least in part on the nature of the formulation and the ultimate target site where the cells of the presently disclosed subject matter are desired to engraft. In some embodiments, the method of administration encompasses features for regionalized delivery or accumulation of the cells and/or compositions at the site in need of treatment. In some embodiments, the cells and/or compositions are delivered directly into the tissue or organ to be treated. In some embodiments, selective delivery of the presently disclosed cells and/or compositions is accomplished by intravenous injection of cells and/or compositions, where the cells home to the target tissue or organ and engraft therein.

VI.C. Dose

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Ex Vivo Expansion of Murine VSELs

Murine VSELs were isolated by multi-parameter sorting using a MOFLOW™ XDP sorter (Beckman Coulter, Inc., Indianapolis, Indiana, United States of America). Highly purified Sca-1$^+$/lin$^-$/CD45$^-$ murine bone marrow VSELs were cultured in D-MEM culture medium containing 5% fetal bovine serum (FBS) supplemented with 10 U/ml luteinizing hormone (LH) and 10 U/ml follicle-stimulating hormone (FSH) in a humidified incubator maintained at 37° C. with 5% $CO_2$. VSELs were exposed to the HDAC inhibitor valproic acid (VPA; Sigma Aldrich, St. Louis, Missouri, United States of America) at a concentration of 1 mM. The cultures were supplemented with fresh LH and FSH every third day. The cultures were maintained for approximately two (2) months. See FIGS. 1A-1D.

The average expansion of sorted purified murine VSELs at 2 months was 21±3 fold as compared to day 0. Of note, this does not preclude that further expansion of murine VSELs could be obtained over a longer time period under the same and/or a different set of culture conditions.

Example 2

Ex Vivo Expansion of Human UCB-Derived VSELs

Human UCB-derived VSELs were isolated by multi-parameter sorting using a MOFLOW™ XDP sorter (Beckman Coulter, Inc.). Small CD133$^+$/lin$^-$/CD45$^-$ cells were plated in 96 well plates in D-MEM medium supplemented with 10% FBS in the presence of VPA (1 mM), LH (10 U/ml), FSH (10 U/ml) and transforming growth factor beta (TGFβ; 10 ng/ml). Cells were cultured for two (2) months in a humidified incubator at 37° C., 5% $CO_2$. Fresh medium was added every 7 days. See FIGS. 2A-2D.

The average expansion of sorted purified human VSELs at 2 months was 32±5 fold as compared to day 0. Here as well, these observations do not preclude that further expansion of human VSELs could be obtained over a longer time period under the same and/or different culture conditions.

Figure 3A:
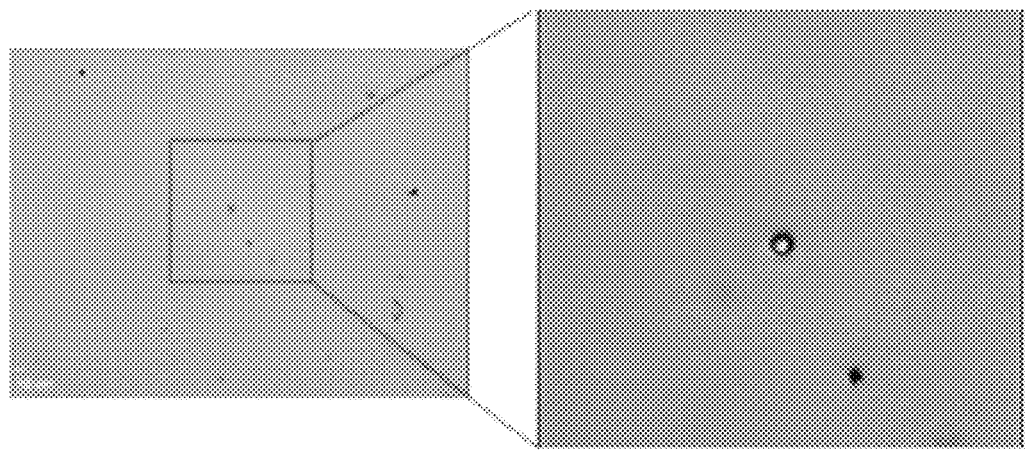
FIGS. 3A and 3B are photomicrographs of cultures of human cord blood-derived VSELs before and after ex vivo expansion.
Figure 3B:
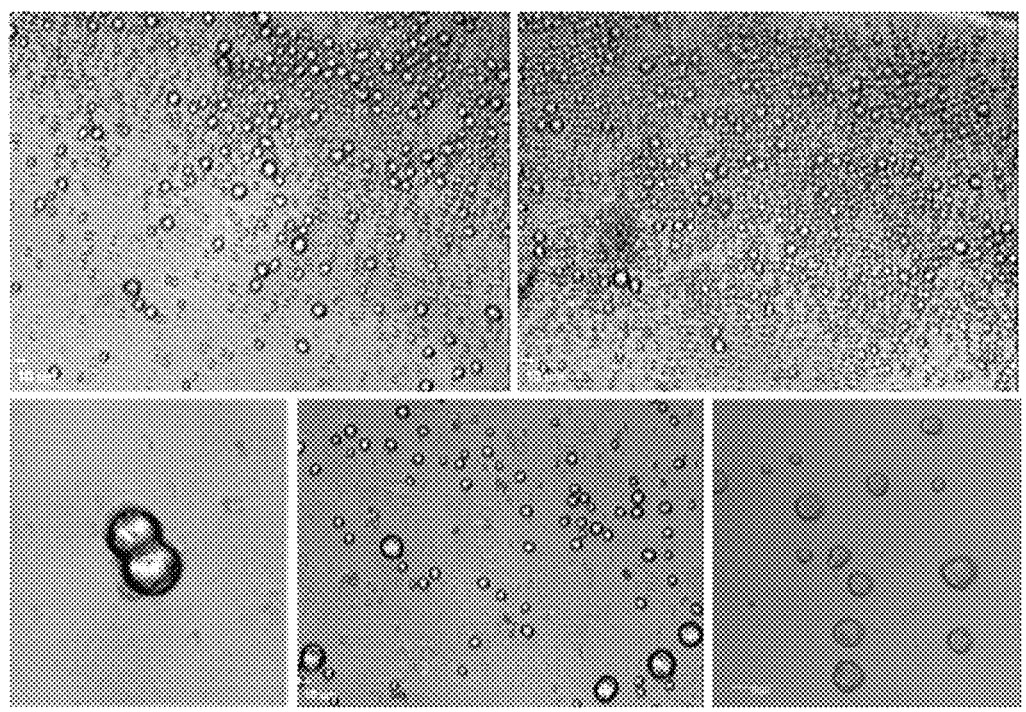

FIGS. 3A and 3B show another representative example of human UCB-derived VSELs before and after ex vivo expansion. Freshly sorted human UCB-derived VSELs ($5\times10^2$) were plated in 0.2 ml of DMEM+10% FBS, supplemented with 1 mM VPA and a cocktail of two pituitary sex hormones—FSH and LH (10 U/ml each)—together with BMP-4 (5 ng/ml), IGF-2 (10 ng/ml), and Kit Ligand (KL; 205 ng/ml). Right inset shows enlarged image of freshly sorted VSEL. Cells were cultured for 2 months and half of culture medium has been changed every 7 days. Panel B—Upper panel—VSELs in these culture conditions began to proliferate, and after 2 months of expansion we can distinguish many small cells as well as some larger cells. Maximal expansion is achieved after 2-3 months of culture. Lower panel—cells aspirated from the cultures. Left and middle panel light microscope image. Right panel—Hoe3342 intravital staining of cells aspirated from the expansion.

Example 3

Epigenetic Modifications of Ex Vivo Expansion of VSEL-Derived Cells

During ex vivo expansion, VSEL-derived cells acquired a somatic imprint on regulatory regions of genes that have been observed to be erased in VSELs per se (e.g., the differentially-methylated region (DMR) of the Igf2-H19 locus). Cells expanded using the compositions and methods of the presently disclosed subject matter (e.g., media that contained FSH and LH) also increased expression of genes characteristic of primordial germ cells (PGCs).

REFERENCES

All references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Aapola et al. (2002) *Nucleic Acids Res* 30:3602-3608.
Anderson et al. (1999) *Neoplasia* 1: 340-348.
Bass (2001) 411 *Nature* 428-429.
Bernstein et al. (2001) 409 *Nature* 363-366.
Bug et al. (2005) *Cancer Res* 65:2537-2541.
Canadian Patent Application No. 2,359,180.
Caplan et al. (2001) 7 *Trends Mol Med* 259-264.
Casola et al. (1997) *Oncogene* 14:1503-1510.
Cea et al. (2011) *PLOS ONE* 6:e22739.
Chaurasia et al. (2014) *J Clin Invest* 2378-2395.
Corti et al. (2002) 277 *Exp Cell Res* 74-85.
Court et al. (2014) *Genome Res* 24:554-569.
Cui et al. (2003) *Science* 299:1753-1755.
De Souza et al. (1997) *FASEB J* 11:60-67.
Delaval & Feil (2004) *Curr Opin Genet Dev* 14:188-195.
Deplus et al. (2002) *Nucleic Acids Res* 30:3831-3838.
Dokmanovic et al. (2007) *Mol Cancer Res* 5:981-989.
Elbashir et al. (2001a) 15 *Genes Dev* 188-200.
Elbashir et al. (2001b) 411 *Nature* 494-498.
Fire (1999) 15 *Trends Genet* 15:358-363.
Fire et al. (1998) 391 *Nature* 806-811.
Fournier et al. (2002) *EMBO J* 21:6560-6570.
GENBANK® Accession Nos. AAB25223; AAR16420; NM_012238; NM_001142498; NM_001314049; NP_002829; NP_034868; NP_035340; NP_036370; NP_598415; NP_612516; NP_776434; NP_999251; NP_001009318; NP_001135970; NP_001300978;

NR_029587.1; NR_029610.1; NR_029639.1;
NR_029723.1; NR_029751.1; NR_029779.1;
NR_029792.1; NR_029834.1; NR_029960.1;
NR_029961.1; NR_030387.1; NR_030452.1;
NR_030602.1; NR_031572.1; NR_031850.1;
NR_031915.1; NR_031916.1; NR_031917.1;
NR_031950.1; NR_049215.1; NR_049328.1;
NR_128867.1; XP_002829; XP_223083; XP_599431.
Hammond et al. (2000) 404 *Nature* 293-296.
Hao et al. (2003) 12 *J Hematother Stem Cell Res* 23-32.
Hatada et al. (1996) *Nat Genet* 14:171-173.
Haynesworth et al. (1992) 13 *Bone* 81-88.
Holm et al. (2005) *Cancer Cell* 8:275-285.
Horii et al. (2008) *Stem Cells* 26:79-88.
Ianus et al. (2003) 111 *J Clin Invest* 843-850.
Kim et al. (2014) *Int J Stem Cells* 7:55-62.
Kobatake et al. (2004) *Oncol Rep* 12:1087-1092.
Kobayashi et al. (2006) *Cytogenet Genome Res* 113:130-137.
Korbling et al. (2002) 346 *N Engl J Med* 738-746.
Kucia et al. (2006) *Leukemia* 20:857-869.
Kucia et al. (2007) *Leukemia* 21:297-303.
Kucia et al. (2009) *Cell Tissue Res* 331:125-134.
Labarge & Blau (2002) 111 *Cell* 589-601.
Lee & Stoffel (2003) 111 *J Clin Invest* 799-801.
Lopes et al. (2003) *Hum Mol Genet* 12:295-305.
Mackay et al. (1998) 4 *Tissue Eng* 415-428.
Mager et al. (2003) *Nat Genet* 33:502-507.
Makino et al. (1999) 103 *J Clin Invest* 697-705.
Mierzejewska et al. (2015) 24 *Stem Cells Dev* 927-937.
Miller et al. (2003) *J Med Chem* 46:5098-5116.
Nykanen et al. (2001) 107 *Cell* 309-321.
Orlic et al. (2003) 7 *Pediatr Transplant* 86-88.
Pan et al. (2007) *Cell Mol Immunol* 4:337-343.
Pannetier & Feil (2007) *Trends Biotechnol* 25:556-562.
PCT International Patent Application Publication Nos. WO 99/07409; WO 99/32619; WO 2000/01846; WO 2000/44895; WO 2000/44914; WO 2000/63364; WO 2001/04313; WO 2001/29058; WO 2001/36646; WO 2001/68836; WO 2001/75164; WO 2001/92513; WO 2002/044321; WO 2002/055692; WO 2002/055693; WO 2007/067280; WO 2009/059032.
Petersen et al. (1999) 284 *Science* 1168-1170.
Pittenger et al. (2000) 251 *Curr Top Microbiol Immunol* 3-11.
Porcu et al. (2005) 26 *Trends Pharmacol Sci* 94-103.
Ratajczak et al. (2008) *Stem Cell Rev* 4:89-99.
Ratajczak et al. (2011) *Exp Hematol* 39:225-237.
Reed & Leff (1994) *Nat Genet* 6:163-167.
Reik & Walter (2001) *Nat Rev Genet* 2:21-32.
Reyes & Verfaillie (2001) 938 *Ann NY Acad Sci* 231-235.
Reyes et al. (2001) 98 *Blood* 2615-2625.
Sanchez-Ramos (2002) 69 *Neurosci Res* 880-893.
Schwartz et al. (2000) 109 *J Clin Invest* 1291-1302.
Shin et al. (2009) *Leukemia* 23:2042-2051.
Sillesen et al. (2015) *J Trauma Acute Care Surg* 80:26-33.
Stamm et al. (2003) 361 *Lancet* 45-46.
Tamamura et al. (1998) 253 *Biochem Biophys Res Comm* 877-882.
Trouillard et al. (2004) *Cancer Genet Cytogenet* 151:182-183.
U.S. Patent Application Publication Nos. 2006/0182724; 2007/0043050; 2009/0155225; 2009/0220466; 2010/0267107; 2012/0114614; 2014/0154219; 2015/0164952; 2015/0250824.
U.S. Pat. Nos. 5,736,396; 5,750,397; 8,273,866; 8,852,938; 8,895,299; 9,155,762; 9,181,544; 9,205,100.
Vo & Daley (2015) *Blood* 125:2641-2648.
Wianny & Zernicka-Goetz (1999) 2 *Nature Cell Biol* 70-75.
Yamazaki et al. (2003) *Proc Natl Acad Sci USA* 100:12207-12212.
Yoo et al. (1998) 80 *J Bone Joint Surg Am* 1745-1757.
Young et al. (1998) 16 *J Orthop Res* 406-413.
Zhao et al. (2014) *J Trauma Acute Care Surg* 77:913-919.
Zuba-Surma et al. (2000) *Cytometry A* 73A:1116-1127.

It will be understood that various details of the presently disclosed subject matter can be changed without departing from the scope of the presently disclosed subject matter. Furthermore, the foregoing description is for the purpose of illustration only, and not for the purpose of limitation.

---

What is claimed is:

1. A feeder cell-free cell culture comprising a plurality of VSELs, one or more ex vivo expanded VSELs, and a culture medium, wherein the culture medium comprises a bovine serum or a serum replacement, a histone deacetylase (HDAC) inhibitor selected from the group consisting of valproic acid (VPA), nicotinic acid (NA), and nicotinamide (NAM), luteinizing hormone (LH), follicle-stimulating hormone (FSH), and optionally transforming growth factor beta (TGFβ), which together are present in an effective amount to overcome quiescence of the VSELs, resulting in expansion of the VSELs.

2. The feeder cell-free cull culture of claim 1, wherein the culture medium comprises 10 U/ml LH, 10 U/ml FSH, 1 mM VPA, and optionally 10 ng/ml TGFβ, or comprises 10 U/ml LH, 10 U/ml FSH, 2.5 mM NAM, and optionally 10 ng/ml TGFβ.

3. The feeder cell-free cell culture of claim 1, wherein the VSELs and/or the expanded VSELs are maintained in the cell culture for at least about two months.

* * * * *

SEQUENCE LISTING

```
<160> NUMBER OF SEQ ID NOS: 28

<210> SEQ ID NO 1
<211> LENGTH: 4110
<212> TYPE: DNA
<213> ORGANISM: Homo sapiens
<220> FEATURE:
<221> NAME/KEY: CDS
<222> LOCATION: (54)..(2297)

<400> SEQUENCE: 1
gtcgagcggg agcagaggag gcgagggagg agggccagag aggcagttgg aag atg         56
                                                             Met
                                                             1 gcg gac gag gcg gcc ctc gcc ctt cag ccc ggc ggc tcc ccc tcg gcg       104
Ala Asp Glu Ala Ala Leu Ala Leu Gln Pro Gly Gly Ser Pro Ser Ala
          5                  10                  15 gcg ggg gcc gac agg gag gcc gcg tcg tcc ccc gcc ggg gag ccg ctc       152
Ala Gly Ala Asp Arg Glu Ala Ala Ser Ser Pro Ala Gly Glu Pro Leu
        20                  25                  30 cgc aag agg ccg cgg aga gat ggt ccc ggc ctc gag cgg agc ccg ggc       200
Arg Lys Arg Pro Arg Arg Asp Gly Pro Gly Leu Glu Arg Ser Pro Gly
    35                  40                  45
```

| | | |
|---|---|---|
| gag ccc ggt ggg gcg gcc cca gag cgt gag gtg ccg gcg gcg gcc agg<br>Glu Pro Gly Gly Ala Ala Pro Glu Arg Glu Val Pro Ala Ala Ala Arg<br>50                           55                    60                  65 | 248 |
| ggc tgc ccg ggt gcg gcg gcg gcg ctg tgg cgg gag gcg gag gca<br>Gly Cys Pro Gly Ala Ala Ala Ala Ala Leu Trp Arg Glu Ala Glu Ala<br>                  70                    75                  80 | 296 |
| gag gcg gcg gcg gca ggc ggg gag caa gag gcc cag gcg act gcg gcg<br>Glu Ala Ala Ala Ala Gly Gly Glu Gln Glu Ala Gln Ala Thr Ala Ala<br>       85                    90                  95 | 344 |
| gct ggg gaa gga gac aat ggg ccg ggc ctg cag ggc cca tct cgg gag<br>Ala Gly Glu Gly Asp Asn Gly Pro Gly Leu Gln Gly Pro Ser Arg Glu<br>100                       105                 110 | 392 |
| cca ccg ctg gcc gac aac ttg tac gac gaa gac gac gac gag ggc<br>Pro Pro Leu Ala Asp Asn Leu Tyr Asp Glu Asp Asp Asp Asp Glu Gly<br>115                     120                 125 | 440 |
| gag gag gag gaa gag gcg gcg gcg gcg gcg att ggg tac cga gat aac<br>Glu Glu Glu Glu Glu Ala Ala Ala Ala Ala Ile Gly Tyr Arg Asp Asn<br>130                     135                 140              145 | 488 |
| ctt ctg ttc ggt gat gaa att atc act aat ggt ttt cat tcc tgt gaa<br>Leu Leu Phe Gly Asp Glu Ile Ile Thr Asn Gly Phe His Ser Cys Glu<br>                  150                 155                 160 | 536 |
| agt gat gag gag gat aga gcc tca cat gca agc tct agt gac tgg act<br>Ser Asp Glu Glu Asp Arg Ala Ser His Ala Ser Ser Ser Asp Trp Thr<br>                  165                 170                 175 | 584 |
| cca agg cca cgg ata ggt cca tat act ttt gtt cag caa cat ctt atg<br>Pro Arg Pro Arg Ile Gly Pro Tyr Thr Phe Val Gln Gln His Leu Met<br>                  180                 185                 190 | 632 |
| att ggc aca gat cct cga aca att ctt aaa gat tta ttg ccg gaa aca<br>Ile Gly Thr Asp Pro Arg Thr Ile Leu Lys Asp Leu Leu Pro Glu Thr<br>195                     200                 205 | 680 |
| ata cct cca cct gag ttg gat gat atg aca ctg tgg cag att gtt att<br>Ile Pro Pro Pro Glu Leu Asp Asp Met Thr Leu Trp Gln Ile Val Ile<br>210                     215                 220              225 | 728 |
| aat atc ctt tca gaa cca cca aaa agg aaa aaa aga aaa gat att aat<br>Asn Ile Leu Ser Glu Pro Pro Lys Arg Lys Lys Arg Lys Asp Ile Asn<br>                  230                 235                 240 | 776 |
| aca att gaa gat gct gtg aaa tta ctg caa gag tgc aaa aaa att ata<br>Thr Ile Glu Asp Ala Val Lys Leu Leu Gln Glu Cys Lys Lys Ile Ile<br>245                     250                 255 | 824 |
| gtt cta act gga gct ggg gtg tct gtt tca tgt gga ata cct gac ttc<br>Val Leu Thr Gly Ala Gly Val Ser Val Ser Cys Gly Ile Pro Asp Phe<br>260                     265                 270 | 872 |
| agg tca agg gat ggt att tat gct cgc ctt gct gta gac ttc cca gat<br>Arg Ser Arg Asp Gly Ile Tyr Ala Arg Leu Ala Val Asp Phe Pro Asp<br>275                     280                 285 | 920 |
| ctt cca gat cct caa gcg atg ttt gat att gaa tat ttc aga aaa gat<br>Leu Pro Asp Pro Gln Ala Met Phe Asp Ile Glu Tyr Phe Arg Lys Asp<br>290                     295                 300              305 | 968 |
| cca aga cca ttc ttc aag ttt gca aag gaa ata tat cct gga caa ttc<br>Pro Arg Pro Phe Phe Lys Phe Ala Lys Glu Ile Tyr Pro Gly Gln Phe<br>                  310                 315                 320 | 1016 |
| cag cca tct ctc tgt cac aaa ttc ata gcc ttg tca gat aag gaa gga<br>Gln Pro Ser Leu Cys His Lys Phe Ile Ala Leu Ser Asp Lys Glu Gly<br>325                     330                 335 | 1064 |
| aaa cta ctt cgc aac tat acc cag aac ata gac acg ctg gaa cag gtt<br>Lys Leu Leu Arg Asn Tyr Thr Gln Asn Ile Asp Thr Leu Glu Gln Val<br>340                     345                 350 | 1112 |
| gcg gga atc caa agg ata att cag tgt cat ggt tcc ttt gca aca gca<br>Ala Gly Ile Gln Arg Ile Ile Gln Cys His Gly Ser Phe Ala Thr Ala | 1160 |

-continued

```
                  355                 360                 365
tct tgc ctg att tgt aaa tac aaa gtt gac tgt gaa gct gta cga gga      1208
Ser Cys Leu Ile Cys Lys Tyr Lys Val Asp Cys Glu Ala Val Arg Gly
370                 375                 380                 385 gat att ttt aat cag gta gtt cct cga tgt cct agg tgc cca gct gat      1256
Asp Ile Phe Asn Gln Val Val Pro Arg Cys Pro Arg Cys Pro Ala Asp
            390                 395                 400 gaa ccg ctt gct atc atg aaa cca gag att gtg ttt ttt ggt gaa aat      1304
Glu Pro Leu Ala Ile Met Lys Pro Glu Ile Val Phe Phe Gly Glu Asn
        405                 410                 415 tta cca gaa cag ttt cat aga gcc atg aag tat gac aaa gat gaa gtt      1352
Leu Pro Glu Gln Phe His Arg Ala Met Lys Tyr Asp Lys Asp Glu Val
    420                 425                 430 gac ctc ctc att gtt att ggg tct tcc ctc aaa gta aga cca gta gca      1400
Asp Leu Leu Ile Val Ile Gly Ser Ser Leu Lys Val Arg Pro Val Ala
435                 440                 445 cta att cca agt tcc ata ccc cat gaa gtg cct cag ata tta att aat      1448
Leu Ile Pro Ser Ser Ile Pro His Glu Val Pro Gln Ile Leu Ile Asn
450                 455                 460                 465 aga gaa cct ttg cct cat ctg cat ttt gat gta gag ctt ctt gga gac      1496
Arg Glu Pro Leu Pro His Leu His Phe Asp Val Glu Leu Leu Gly Asp
            470                 475                 480 tgt gat gtc ata att aat gaa ttg tgt cat agg tta ggt ggt gaa tat      1544
Cys Asp Val Ile Ile Asn Glu Leu Cys His Arg Leu Gly Gly Glu Tyr
        485                 490                 495 gcc aaa ctt tgc tgt aac cct gta aag ctt tca gaa att act gaa aaa      1592
Ala Lys Leu Cys Cys Asn Pro Val Lys Leu Ser Glu Ile Thr Glu Lys
    500                 505                 510 cct cca cga aca caa aaa gaa ttg gct tat ttg tca gag ttg cca ccc      1640
Pro Pro Arg Thr Gln Lys Glu Leu Ala Tyr Leu Ser Glu Leu Pro Pro
515                 520                 525 aca cct ctt cat gtt tca gaa gac tca agt tca cca gaa aga act tca      1688
Thr Pro Leu His Val Ser Glu Asp Ser Ser Ser Pro Glu Arg Thr Ser
530                 535                 540                 545 cca cca gat tct tca gtg att gtc aca ctt tta gac caa gca gct aag      1736
Pro Pro Asp Ser Ser Val Ile Val Thr Leu Leu Asp Gln Ala Ala Lys
            550                 555                 560 agt aat gat gat tta gat gtg tct gaa tca aaa ggt tgt atg gaa gaa      1784
Ser Asn Asp Asp Leu Asp Val Ser Glu Ser Lys Gly Cys Met Glu Glu
        565                 570                 575 aaa cca cag gaa gta caa act tct agg aat gtt gaa agt att gct gaa      1832
Lys Pro Gln Glu Val Gln Thr Ser Arg Asn Val Glu Ser Ile Ala Glu
    580                 585                 590 cag atg gaa aat ccg gat ttg aag aat gtt ggt tct agt act ggg gag      1880
Gln Met Glu Asn Pro Asp Leu Lys Asn Val Gly Ser Ser Thr Gly Glu
595                 600                 605 aaa aat gaa aga act tca gtg gct gga aca gtg aga aaa tgc tgg cct      1928
Lys Asn Glu Arg Thr Ser Val Ala Gly Thr Val Arg Lys Cys Trp Pro
610                 615                 620                 625 aat aga gtg gca aag gag cag att agt agg cgg ctt gat ggt aat cag      1976
Asn Arg Val Ala Lys Glu Gln Ile Ser Arg Arg Leu Asp Gly Asn Gln
            630                 635                 640 tat ctg ttt ttg cca cca aat cgt tac att ttc cat ggc gct gag gta      2024
Tyr Leu Phe Leu Pro Pro Asn Arg Tyr Ile Phe His Gly Ala Glu Val
        645                 650                 655 tat tca gac tct gaa gat gac gtc tta tcc tct agt tct tgt ggc agt      2072
Tyr Ser Asp Ser Glu Asp Asp Val Leu Ser Ser Ser Ser Cys Gly Ser
    660                 665                 670 aac agt gat agt ggg aca tgc cag agt cca agt tta gaa gaa ccc atg      2120
Asn Ser Asp Ser Gly Thr Cys Gln Ser Pro Ser Leu Glu Glu Pro Met
```

```
Asn Ser Asp Ser Gly Thr Cys Gln Ser Pro Ser Leu Glu Glu Pro Met
    675                 680                 685 gag gat gaa agt gaa att gaa gaa ttc tac aat ggc tta gaa gat gag      2168
Glu Asp Glu Ser Glu Ile Glu Glu Phe Tyr Asn Gly Leu Glu Asp Glu
690                 695                 700                 705 cct gat gtt cca gag aga gct gga gga gct gga ttt ggg act gat gga      2216
Pro Asp Val Pro Glu Arg Ala Gly Gly Ala Gly Phe Gly Thr Asp Gly
            710                 715                 720 gat gat caa gag gca att aat gaa gct ata tct gtg aaa cag gaa gta      2264
Asp Asp Gln Glu Ala Ile Asn Glu Ala Ile Ser Val Lys Gln Glu Val
                725                 730                 735 aca gac atg aac tat cca tca aac aaa tca tag tgtaataatt gtgcaggtac    2317
Thr Asp Met Asn Tyr Pro Ser Asn Lys Ser
            740                 745 aggaattgtt ccaccagcat taggaacttt agcatgtcaa aatgaatgtt tacttgtgaa    2377
ctcgatagag caaggaaacc agaaaggtgt aatatttata ggttggtaaa atagattgtt    2437
tttcatggat aatttttaac ttcattattt ctgtacttgt acaaactcaa cactaacttt    2497
ttttttttta aaaaaaaaaa ggtactaagt atcttcaatc agctgttggt caagactaac    2557
tttcttttaa aggttcattt gtatgataaa ttcatatgtg tatatataat ttttttttgtt   2617
ttgtctagtg agtttcaaca ttttttaaagt tttcaaaaag ccatcggaat gttaaattaa   2677
tgtaaaggga acagctaatc tagaccaaag aatggtattt tcactttcct ttgtaacatt    2737
gaatggtttg aagtactcaa aatctgttac gctaaacttt tgattcttta acacaattat    2797
ttttaaacac tggcattttc caaaactgtg gcagctaact ttttaaaatc tcaaatgaca    2857
tgcagtgtga gtagaaggaa gtcaacaata tgtggggaga gcactcggtt gtctttactt    2917
ttaaaagtaa tacttggtgc taagaatttc aggattattg tatttacgtt caaatgaaga    2977
tggcttttgt acttcctgtg gacatgtagt aatgtctata ttggctcata aaactaacct    3037
gaaaaacaaa taaatgcttt ggaaatgttt cagttgcttt agaaacatta gtgcctgcct    3097
ggatccccctt agttttgaaa tatttgccat tgttgtttaa atacctatca ctgtggtaga   3157
gcttgcattg atcttttcca caagtattaa actgccaaaa tgtgaatatg caaagccttt    3217
ctgaatctat aataatggta cttctactgg ggagagtgta atattttgga ctgctgtttt    3277
ccattaatga ggagagcaac aggcccctga ttatacagtt ccaaagtaat aagatgttaa    3337
ttgtaattca gccagaaagt acatgtctcc cattgggagg atttggtgtt aaataccaaa    3397
ctgctagccc tagtattatg gagatgaaca tgatgatgta acttgtaata gcagaatagt    3457
taatgaatga aactagttct tataatttat ctttatttaa aagcttagcc tgccttaaaa    3517
ctagagatca actttctcag ctgcaaaagc ttctagtctt tcaagaagtt catactttat    3577
gaaattgcac agtaagcatt tattttttcag accattttttg aacatcactc ctaaattaat  3637
aaagtattcc tctgttgctt tagtatttat tacaataaaa agggtttgaa atatagctgt    3697
tctttatgca taaacaccc agctaggacc attactgcca gagaaaaaaa tcgtattgaa     3757
tggccatttc cctacttata agatgtctca atctgaattt atttggctac actaaagaat    3817
gcagtatatt tagtttttcca tttgcatgat gtttgtgtgc tatagatgat attttaaatt   3877
gaaaagtttg tttaaaatta ttttttacagt gaagactgtt ttcagctctt tttatattgt   3937
acatagtctt ttatgtaatt tactggcata tgttttgtag actgtttaat gactggatat    3997
cttccttcaa cttttgaaat acaaaaccag tgtttttttac ttgtcacactg ttttaaagtc  4057
tattaaaatt gtcatttgac ttttttctgt taacttaaaa aaaaaaaaaa aaa           4110
```

<210> SEQ ID NO 2
<211> LENGTH: 747
<212> TYPE: PRT
<213> ORGANISM: Homo sapiens

<400> SEQUENCE: 2

```
Met Ala Asp Glu Ala Ala Leu Ala Leu Gln Pro Gly Gly Ser Pro Ser
1               5                   10                  15

Ala Ala Gly Ala Asp Arg Glu Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65                  70                  75                  80

Ala Glu Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380
```

```
Gly Asp Ile Phe Asn Gln Val Pro Arg Cys Pro Arg Cys Pro Ala
385                 390                 395                 400

Asp Glu Pro Leu Ala Ile Met Lys Pro Glu Ile Val Phe Phe Gly Glu
            405                 410                 415

Asn Leu Pro Glu Gln Phe His Arg Ala Met Lys Tyr Asp Lys Asp Glu
        420                 425                 430

Val Asp Leu Leu Ile Val Ile Gly Ser Ser Leu Lys Val Arg Pro Val
            435                 440                 445

Ala Leu Ile Pro Ser Ser Ile Pro His Glu Val Pro Gln Ile Leu Ile
450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Asp Val Leu Ser Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745

<210> SEQ ID NO 3
<211> LENGTH: 3604
<212> TYPE: DNA
<213> ORGANISM: Homo sapiens
<220> FEATURE:
<221> NAME/KEY: CDS
<222> LOCATION: (433)..(1791)
```

<400> SEQUENCE: 3

```
gcatctcctc ctccctctcc ccgggctcct actggcctga ggttgagggc ggctgggggc    60
tcggggcagg ctccgcggcg ttcccctccc caccccggcc ctccgttcag ccgcgctcct   120
ccggggctgc ggttcctact gcgcgagctg ccagtggatt cgctcttttc ctccgtccgt   180
ggcccgcctg gcggccttg ttctttccgc agcagccaga taaccttctg ttcggtgatg    240
aaattatcac taatggtttt cattcctgtg aaagtgatga ggaggataga gcctcacatg   300
caagctctag tgactggact ccaaggccac ggataggtgt ctgtttcatg tggaatacct   360
gacttcaggt caagggatgg tatttatgct cgccttgctg tagacttccc agatcttcca   420
gatcctcaag cg atg ttt gat att gaa tat ttc aga aaa gat cca aga cca   471
              Met Phe Asp Ile Glu Tyr Phe Arg Lys Asp Pro Arg Pro
                1               5                  10 ttc ttc aag ttt gca aag gaa ata tat cct gga caa ttc cag cca tct    519
Phe Phe Lys Phe Ala Lys Glu Ile Tyr Pro Gly Gln Phe Gln Pro Ser
         15                  20                  25 ctc tgt cac aaa ttc ata gcc ttg tca gat aag gaa gga aaa cta ctt    567
Leu Cys His Lys Phe Ile Ala Leu Ser Asp Lys Glu Gly Lys Leu Leu
 30                  35                  40                  45 cgc aac tat acc cag aac ata gac acg ctg gaa cag gtt gcg gga atc    615
Arg Asn Tyr Thr Gln Asn Ile Asp Thr Leu Glu Gln Val Ala Gly Ile
                 50                  55                  60 caa agg ata att cag tgt cat ggt tcc ttt gca aca gca tct tgc ctg    663
Gln Arg Ile Ile Gln Cys His Gly Ser Phe Ala Thr Ala Ser Cys Leu
             65                  70                  75 att tgt aaa tac aaa gtt gac tgt gaa gct gta cga gga gat att ttt    711
Ile Cys Lys Tyr Lys Val Asp Cys Glu Ala Val Arg Gly Asp Ile Phe
         80                  85                  90 aat cag gta gtt cct cga tgt cct agg tgc cca gct gat gaa ccg ctt    759
Asn Gln Val Val Pro Arg Cys Pro Arg Cys Pro Ala Asp Glu Pro Leu
     95                 100                 105 gct atc atg aaa cca gag att gtg ttt ttt ggt gaa aat tta cca gaa    807
Ala Ile Met Lys Pro Glu Ile Val Phe Phe Gly Glu Asn Leu Pro Glu
110                 115                 120                 125 cag ttt cat aga gcc atg aag tat gac aaa gat gaa gtt gac ctc ctc    855
Gln Phe His Arg Ala Met Lys Tyr Asp Lys Asp Glu Val Asp Leu Leu
                130                 135                 140 att gtt att ggg tct tcc ctc aaa gta aga cca gta gca cta att cca    903
Ile Val Ile Gly Ser Ser Leu Lys Val Arg Pro Val Ala Leu Ile Pro
            145                 150                 155 agt tcc ata ccc cat gaa gtg cct cag ata tta att aat aga gaa cct    951
Ser Ser Ile Pro His Glu Val Pro Gln Ile Leu Ile Asn Arg Glu Pro
        160                 165                 170 ttg cct cat ctg cat ttt gat gta gag ctt ctt gga gac tgt gat gtc    999
Leu Pro His Leu His Phe Asp Val Glu Leu Leu Gly Asp Cys Asp Val
    175                 180                 185 ata att aat gaa ttg tgt cat agg tta ggt ggt gaa tat gcc aaa ctt   1047
Ile Ile Asn Glu Leu Cys His Arg Leu Gly Gly Glu Tyr Ala Lys Leu
190                 195                 200                 205 tgc tgt aac cct gta aag ctt tca gaa att act gaa aaa cct cca cga   1095
Cys Cys Asn Pro Val Lys Leu Ser Glu Ile Thr Glu Lys Pro Pro Arg
                210                 215                 220 aca caa aaa gaa ttg gct tat ttg tca gag ttg cca ccc aca cct ctt   1143
Thr Gln Lys Glu Leu Ala Tyr Leu Ser Glu Leu Pro Pro Thr Pro Leu
            225                 230                 235 cat gtt tca gaa gac tca agt tca cca gaa aga act tca cca cca gat   1191
His Val Ser Glu Asp Ser Ser Ser Pro Glu Arg Thr Ser Pro Pro Asp
        240                 245                 250
```

```
tct tca gtg att gtc aca ctt tta gac caa gca gct aag agt aat gat     1239
Ser Ser Val Ile Val Thr Leu Leu Asp Gln Ala Ala Lys Ser Asn Asp
    255                 260                 265 gat tta gat gtg tct gaa tca aaa ggt tgt atg gaa gaa aaa cca cag     1287
Asp Leu Asp Val Ser Glu Ser Lys Gly Cys Met Glu Glu Lys Pro Gln
270                 275                 280                 285 gaa gta caa act tct agg aat gtt gaa agt att gct gaa cag atg gaa     1335
Glu Val Gln Thr Ser Arg Asn Val Glu Ser Ile Ala Glu Gln Met Glu
                290                 295                 300 aat ccg gat ttg aag aat gtt ggt tct agt act ggg gag aaa aat gaa     1383
Asn Pro Asp Leu Lys Asn Val Gly Ser Ser Thr Gly Glu Lys Asn Glu
            305                 310                 315 aga act tca gtg gct gga aca gtg aga aaa tgc tgg cct aat aga gtg     1431
Arg Thr Ser Val Ala Gly Thr Val Arg Lys Cys Trp Pro Asn Arg Val
        320                 325                 330 gca aag gag cag att agt agg cgg ctt gat ggt aat cag tat ctg ttt     1479
Ala Lys Glu Gln Ile Ser Arg Arg Leu Asp Gly Asn Gln Tyr Leu Phe
    335                 340                 345 ttg cca cca aat cgt tac att ttc cat ggc gct gag gta tat tca gac     1527
Leu Pro Pro Asn Arg Tyr Ile Phe His Gly Ala Glu Val Tyr Ser Asp
350                 355                 360                 365 tct gaa gat gac gtc tta tcc tct agt tct tgt ggc agt aac agt gat     1575
Ser Glu Asp Asp Val Leu Ser Ser Ser Ser Cys Gly Ser Asn Ser Asp
                370                 375                 380 agt ggg aca tgc cag agt cca agt tta gaa gaa ccc atg gag gat gaa     1623
Ser Gly Thr Cys Gln Ser Pro Ser Leu Glu Glu Pro Met Glu Asp Glu
            385                 390                 395 agt gaa att gaa gaa ttc tac aat ggc tta gaa gat gag cct gat gtt     1671
Ser Glu Ile Glu Glu Phe Tyr Asn Gly Leu Glu Asp Glu Pro Asp Val
        400                 405                 410 cca gag aga gct gga gga gct gga ttt ggg act gat gga gat gat caa     1719
Pro Glu Arg Ala Gly Gly Ala Gly Phe Gly Thr Asp Gly Asp Asp Gln
    415                 420                 425 gag gca att aat gaa gct ata tct gtg aaa cag gaa gta aca gac atg     1767
Glu Ala Ile Asn Glu Ala Ile Ser Val Lys Gln Glu Val Thr Asp Met
430                 435                 440                 445 aac tat cca tca aac aaa tca tag tgtaataatt gtgcaggtac aggaattgtt   1821
Asn Tyr Pro Ser Asn Lys Ser
                450 ccaccagcat taggaacttt agcatgtcaa atgaatgtt tacttgtgaa ctcgatagag    1881 caaggaaacc agaaaggtgt aatatttata ggttggtaaa atagattgtt tttcatggat    1941 aatttttaac ttcattattt ctgtacttgt acaaactcaa cactaacttt ttttttttta    2001 aaaaaaaaaa ggtactaagt atcttcaatc agctgttggt caagactaac tttctttttaa    2061 aggttcattt gtatgataaa ttcatatgtg tatatataat ttttttttgtt ttgtctagtg    2121 agtttcaaca tttttaaagt tttcaaaaag ccatcggaat gttaaattaa tgtaaaggga    2181 acagctaatc tagaccaaag aatggtattt tcactttttct ttgtaacatt gaatggtttg    2241 aagtactcaa aatctgttac gctaaactt tgattcttta acacaattat ttttaaacac    2301 tggcattttc caaaactgtg gcagctaact tttaaaatc tcaaatgaca tgcagtgtga    2361 gtagaaggaa gtcaacaata tgtggggaga gcactcggtt gtctttactt ttaaaagtaa    2421 tacttggtgc taagaatttc aggattattg tatttacgtt caaatgaaga tggcttttgt    2481 acttcctgtg gacatgtagt aatgtctata ttggctcata aaactaacct gaaaacaaa    2541 taaatgcttt ggaaatgttt cagttgcttt agaaacatta gtgcctgcct ggatccccctt    2601
```

```
agttttgaaa tatttgccat tgttgtttaa atacctatca ctgtggtaga gcttgcattg    2661
atctttccca caagtattaa actgccaaaa tgtgaatatg caaagccttt ctgaatctat    2721
aataatggta cttctactgg ggagagtgta atattttgga ctgctgtttt ccattaatga    2781
ggagagcaac aggcccctga ttatacagtt ccaaagtaat aagatgttaa ttgtaattca    2841
gccagaaagt acatgtctcc cattgggagg atttggtgtt aaataccaaa ctgctagccc    2901
tagtattatg gagatgaaca tgatgatgta acttgtaata gcagaatagt taatgaatga    2961
aactagttct tataatttat ctttatttaa aagcttagcc tgccttaaaa ctagagatca    3021
actttctcag ctgcaaaagc ttctagtctt tcaagaagtt catactttat gaaattgcac    3081
agtaagcatt tattttcag accattttg aacatcactc ctaaattaat aaagtattcc    3141
tctgttgctt tagtatttat tacaataaaa agggtttgaa atatagctgt tctttatgca    3201
taaaacaccc agctaggacc attactgcca gagaaaaaaa tcgtattgaa tggccatttc    3261
cctacttata agatgtctca atctgaattt atttggctac actaaagaat gcagtatatt    3321 tagtttttcca tttgcatgat gtttgtgtgc tatagatgat attttaaatt gaaaagtttg    3381
ttttaaatta ttttacagt gaagactgtt ttcagctctt tttatattgt acatagtctt    3441
ttatgtaatt tactggcata tgttttgtag actgtttaat gactggatat cttccttcaa    3501
cttttgaaat acaaaaccag tgttttttac ttgtacactg ttttaaagtc tattaaaatt    3561
gtcatttgac ttttttctgt taacttaaaa aaaaaaaaaa aaa                      3604
```

<210> SEQ ID NO 4
<211> LENGTH: 452
<212> TYPE: PRT
<213> ORGANISM: Homo sapiens

<400> SEQUENCE: 4

```
Met Phe Asp Ile Glu Tyr Phe Arg Lys Asp Pro Arg Pro Phe Phe Lys
1               5                   10                  15

Phe Ala Lys Glu Ile Tyr Pro Gly Gln Phe Gln Pro Ser Leu Cys His
            20                  25                  30

Lys Phe Ile Ala Leu Ser Asp Lys Glu Gly Lys Leu Leu Arg Asn Tyr
        35                  40                  45

Thr Gln Asn Ile Asp Thr Leu Glu Gln Val Ala Gly Ile Gln Arg Ile
    50                  55                  60

Ile Gln Cys His Gly Ser Phe Ala Thr Ala Ser Cys Leu Ile Cys Lys
65                  70                  75                  80

Tyr Lys Val Asp Cys Glu Ala Val Arg Gly Asp Ile Phe Asn Gln Val
                85                  90                  95

Val Pro Arg Cys Pro Arg Cys Pro Ala Asp Glu Pro Leu Ala Ile Met
            100                 105                 110

Lys Pro Glu Ile Val Phe Phe Gly Glu Asn Leu Pro Glu Gln Phe His
        115                 120                 125

Arg Ala Met Lys Tyr Asp Lys Asp Glu Val Asp Leu Leu Ile Val Ile
    130                 135                 140

Gly Ser Ser Leu Lys Val Arg Pro Val Ala Leu Ile Pro Ser Ser Ile
145                 150                 155                 160

Pro His Glu Val Pro Gln Ile Leu Ile Asn Arg Glu Pro Leu Pro His
                165                 170                 175

Leu His Phe Asp Val Glu Leu Leu Gly Asp Cys Asp Val Ile Ile Asn
            180                 185                 190

Glu Leu Cys His Arg Leu Gly Gly Glu Tyr Ala Lys Leu Cys Cys Asn
```

```
            195                 200                 205
Pro Val Lys Leu Ser Glu Ile Thr Glu Lys Pro Pro Arg Thr Gln Lys
    210                 215                 220

Glu Leu Ala Tyr Leu Ser Glu Leu Pro Pro Thr Pro Leu His Val Ser
225                 230                 235                 240

Glu Asp Ser Ser Pro Glu Arg Thr Ser Pro Pro Asp Ser Ser Val
                245                 250                 255

Ile Val Thr Leu Leu Asp Gln Ala Ala Lys Ser Asn Asp Asp Leu Asp
                260                 265                 270

Val Ser Glu Ser Lys Gly Cys Met Glu Glu Lys Pro Gln Glu Val Gln
            275                 280                 285

Thr Ser Arg Asn Val Glu Ser Ile Ala Glu Gln Met Glu Asn Pro Asp
290                 295                 300

Leu Lys Asn Val Gly Ser Ser Thr Gly Leu Lys Asn Glu Arg Thr Ser
305                 310                 315                 320

Val Ala Gly Thr Val Arg Lys Cys Trp Pro Asn Arg Val Ala Lys Glu
                325                 330                 335

Gln Ile Ser Arg Arg Leu Asp Gly Asn Gln Tyr Leu Phe Leu Pro Pro
                340                 345                 350

Asn Arg Tyr Ile Phe His Gly Ala Glu Val Tyr Ser Asp Ser Glu Asp
                355                 360                 365

Asp Val Leu Ser Ser Ser Cys Gly Ser Asn Ser Asp Ser Gly Thr
370                 375                 380

Cys Gln Ser Pro Ser Leu Glu Glu Pro Met Glu Asp Glu Ser Glu Ile
385                 390                 395                 400

Glu Glu Phe Tyr Asn Gly Leu Glu Asp Glu Pro Asp Val Pro Glu Arg
                405                 410                 415

Ala Gly Gly Ala Gly Phe Gly Thr Asp Gly Asp Asp Gln Glu Ala Ile
                420                 425                 430

Asn Glu Ala Ile Ser Val Lys Gln Glu Val Thr Asp Met Asn Tyr Pro
                435                 440                 445

Ser Asn Lys Ser
    450

<210> SEQ ID NO 5
<211> LENGTH: 3393
<212> TYPE: DNA
<213> ORGANISM: Homo sapiens
<220> FEATURE:
<221> NAME/KEY: CDS
<222> LOCATION: (246)..(1580)

<400> SEQUENCE: 5
gtgtctgttt catgtggaat acctgacttc aggtcaaggg atggtattta tgctcgcctt      60
gctgtagact tcccagatct tccagatcct caagcgatgt tgatattga atatttcaga     120 aaagatccaa gaccattctt caagtttgca aagaagaaac agcattgaag cattatttgg     180
ggggaaaaac acacacacaa atccagcaa ctcagcattc atgagcaact ctatactata     240 ccagt atg tgc ctg tgc agt gga agg aaa aca att ttg gaa ata tat cct     290
      Met Cys Leu Cys Ser Gly Arg Lys Thr Ile Leu Glu Ile Tyr Pro
        1               5                  10                  15 gga caa ttc cag cca tct ctc tgt cac aaa ttc ata gcc ttg tca gat      338
Gly Gln Phe Gln Pro Ser Leu Cys His Lys Phe Ile Ala Leu Ser Asp
                20                  25                  30 aag gaa gga aaa cta ctt cgc aac tat acc cag aac ata gac acg ctg      386
Lys Glu Gly Lys Leu Leu Arg Asn Tyr Thr Gln Asn Ile Asp Thr Leu
```

```
                    35                  40                  45
gaa cag gtt gcg gga atc caa agg ata att cag tgt cat ggt tcc ttt        434
Glu Gln Val Ala Gly Ile Gln Arg Ile Ile Gln Cys His Gly Ser Phe
            50                  55                  60 gca aca gca tct tgc ctg att tgt aaa tac aaa gtt gac tgt gaa gct        482
Ala Thr Ala Ser Cys Leu Ile Cys Lys Tyr Lys Val Asp Cys Glu Ala
65                  70                  75 gta cga gga gat att ttt aat cag gta gtt cct cga tgt cct agg tgc        530
Val Arg Gly Asp Ile Phe Asn Gln Val Val Pro Arg Cys Pro Arg Cys
80                  85                  90                  95 cca gct gat gaa ccg ctt gct atc atg aaa cca gag att gtg ttt ttt        578
Pro Ala Asp Glu Pro Leu Ala Ile Met Lys Pro Glu Ile Val Phe Phe
                100                 105                 110 ggt gaa aat tta cca gaa cag ttt cat aga gcc atg aag tat gac aaa        626
Gly Glu Asn Leu Pro Glu Gln Phe His Arg Ala Met Lys Tyr Asp Lys
            115                 120                 125 gat gaa gtt gac ctc ctc att gtt att ggg tct tcc ctc aaa gta aga        674
Asp Glu Val Asp Leu Leu Ile Val Ile Gly Ser Ser Leu Lys Val Arg
        130                 135                 140 cca gta gca cta att cca agt tcc ata ccc cat gaa gtg cct cag ata        722
Pro Val Ala Leu Ile Pro Ser Ser Ile Pro His Glu Val Pro Gln Ile
145                 150                 155 tta att aat aga gaa cct ttg cct cat ctg cat ttt gat gta gag ctt        770
Leu Ile Asn Arg Glu Pro Leu Pro His Leu His Phe Asp Val Glu Leu
160                 165                 170                 175 ctt gga gac tgt gat gtc ata att aat gaa ttg tgt cat agg tta ggt        818
Leu Gly Asp Cys Asp Val Ile Ile Asn Glu Leu Cys His Arg Leu Gly
                180                 185                 190 ggt gaa tat gcc aaa ctt tgc tgt aac cct gta aag ctt tca gaa att        866
Gly Glu Tyr Ala Lys Leu Cys Cys Asn Pro Val Lys Leu Ser Glu Ile
            195                 200                 205 act gaa aaa cct cca cga aca caa aaa gaa ttg gct tat ttg tca gag        914
Thr Glu Lys Pro Pro Arg Thr Gln Lys Glu Leu Ala Tyr Leu Ser Glu
        210                 215                 220 ttg cca ccc aca cct ctt cat gtt tca gaa gac tca agt tca cca gaa        962
Leu Pro Pro Thr Pro Leu His Val Ser Glu Asp Ser Ser Ser Pro Glu
225                 230                 235 aga act tca cca cca gat tct tca gtg att gtc aca ctt tta gac caa       1010
Arg Thr Ser Pro Pro Asp Ser Ser Val Ile Val Thr Leu Leu Asp Gln
240                 245                 250                 255 gca gct aag agt aat gat gat tta gat gtg tct gaa tca aaa ggt tgt       1058
Ala Ala Lys Ser Asn Asp Asp Leu Asp Val Ser Glu Ser Lys Gly Cys
                260                 265                 270 atg gaa gaa aaa cca cag gaa gta caa act tct agg aat gtt gaa agt       1106
Met Glu Glu Lys Pro Gln Glu Val Gln Thr Ser Arg Asn Val Glu Ser
            275                 280                 285 att gct gaa cag atg gaa aat ccg gat ttg aag aat gtt ggt tct agt       1154
Ile Ala Glu Gln Met Glu Asn Pro Asp Leu Lys Asn Val Gly Ser Ser
        290                 295                 300 act ggg gag aaa aat gaa aga act tca gtg gct gga aca gtg aga aaa       1202
Thr Gly Glu Lys Asn Glu Arg Thr Ser Val Ala Gly Thr Val Arg Lys
305                 310                 315 tgc tgg cct aat aga gtg gca aag gag cag att agt agg cgg ctt gat       1250
Cys Trp Pro Asn Arg Val Ala Lys Glu Gln Ile Ser Arg Arg Leu Asp
320                 325                 330                 335 ggt aat cag tat ctg ttt ttg cca cca aat cgt tac att ttc cat ggc       1298
Gly Asn Gln Tyr Leu Phe Leu Pro Pro Asn Arg Tyr Ile Phe His Gly
                340                 345                 350 gct gag gta tat tca gac tct gaa gat gac gtc tta tcc tct agt tct       1346
Ala Glu Val Tyr Ser Asp Ser Glu Asp Asp Val Leu Ser Ser Ser Ser
```

| | |
|---|---|
| Ala Glu Val Tyr Ser Asp Ser Glu Asp Asp Val Leu Ser Ser Ser Ser<br>           355                    360                    365 | |
| tgt ggc agt aac agt gat agt ggg aca tgc cag agt cca agt tta gaa<br>Cys Gly Ser Asn Ser Asp Ser Gly Thr Cys Gln Ser Pro Ser Leu Glu<br>           370                    375                    380 | 1394 |
| gaa ccc atg gag gat gaa agt gaa att gaa gaa ttc tac aat ggc tta<br>Glu Pro Met Glu Asp Glu Ser Glu Ile Glu Glu Phe Tyr Asn Gly Leu<br>    385                    390                    395 | 1442 |
| gaa gat gag cct gat gtt cca gag aga gct gga gga gct gga ttt ggg<br>Glu Asp Glu Pro Asp Val Pro Glu Arg Ala Gly Gly Ala Gly Phe Gly<br>400                    405                    410                    415 | 1490 |
| act gat gga gat gat caa gag gca att aat gaa gct ata tct gtg aaa<br>Thr Asp Gly Asp Asp Gln Glu Ala Ile Asn Glu Ala Ile Ser Val Lys<br>                  420                    425                    430 | 1538 |
| cag gaa gta aca gac atg aac tat cca tca aac aaa tca tag<br>Gln Glu Val Thr Asp Met Asn Tyr Pro Ser Asn Lys Ser<br>                  435                      440 | 1580 |
| tgtaataatt gtgcaggtac aggaattgtt ccaccagcat taggaacttt agcatgtcaa | 1640 |
| aatgaatgtt tacttgtgaa ctcgatagag caaggaaacc agaaggtgt aatatttata | 1700 |
| ggttggtaaa atagattgtt tttcatggat aatttttaac ttcattattt ctgtacttgt | 1760 |
| acaaactcaa cactaacttt tttttttta aaaaaaaaa ggtactaagt atcttcaatc | 1820 |
| agctgttggt caagactaac tttcttttaa aggttcattt gtatgataaa ttcatatgtg | 1880 |
| tatatataat tttttttgtt ttgtctagtg agtttcaaca tttttaaagt tttcaaaaag | 1940 |
| ccatcggaat gttaaattaa tgtaaaggga acagctaatc tagaccaaag aatggtattt | 2000 |
| tcacttttct ttgtaacatt gaatggtttg aagtactcaa aatctgttac gctaaacttt | 2060 |
| tgattcttta acacaattat ttttaaacac tggcattttc caaaactgtg gcagctaact | 2120 |
| ttttaaaatc tcaaatgaca tgcagtgtga gtagaaggaa gtcaacaata tgtggggaga | 2180 |
| gcactcggtt gtcttttactt taaaagtaa tacttggtgc taagaatttc aggattattg | 2240 |
| tatttacgtt caaatgaaga tggcttttgt acttcctgtg acatgtagt aatgtctata | 2300 |
| ttggctcata aaactaacct gaaaaacaaa taaatgcttt ggaaatgttt cagttgcttt | 2360 |
| agaaacatta gtgcctgcct ggatccccctt agttttgaaa tatttgccat tgttgtttaa | 2420 |
| atacctatca ctgtggtaga gcttgcattg atcttttcca caagtattaa actgccaaaa | 2480 |
| tgtgaatatg caaagccttt ctgaatctat aataatggta cttctactgg ggagagtgta | 2540 |
| atattttgga ctgctgtttt ccattaatga ggagagcaac aggcccctga ttatacagtt | 2600 |
| ccaaagtaat aagatgttaa ttgtaattca gccagaaagt acatgtctcc cattgggagg | 2660 |
| atttggtgtt aaataccaaa ctgctagccc tagtattatg gagatgaaca tgatgatgta | 2720 |
| acttgtaata gcagaatagt taatgaatga aactagttct tataatttat ctttatttaa | 2780 |
| aagcttagcc tgccttaaaa ctagagatca actttctcag ctgcaaaagc ttctagtctt | 2840 |
| tcaagaagtt catactttat gaaattgcac agtaagcatt tattttttcag accattttttg | 2900 |
| aacatcactc ctaaattaat aaagtattcc tctgttgctt tagtatttat tacaataaaa | 2960 |
| agggtttgaa atatagctgt tctttatgca taaaacaccc agctaggacc attactgcca | 3020 |
| gagaaaaaaa tcgtattgaa tggccatttc cctacttata agatgtctca atctgaattt | 3080 |
| atttggctac actaaagaat gcagtatatt tagttttcca tttgcatgat gtttgtgtgc | 3140 |
| tatagatgat atttttaaatt gaaagttttg tttaaaatta tttttacagt gaagactgtt | 3200 |
| ttcagctctt tttatattgt acatagtctt ttatgtaatt tactggcata tgttttgtag | 3260 |

```
actgtttaat gactggatat cttccttcaa cttttgaaat acaaaaccag tgttttttac    3320
ttgtacactg ttttaaagtc tattaaaatt gtcatttgac ttttttctgt taacttaaaa    3380
aaaaaaaaaa aaa                                                        3393
```

<210> SEQ ID NO 6
<211> LENGTH: 444
<212> TYPE: PRT
<213> ORGANISM: Homo sapiens

<400> SEQUENCE: 6

```
Met Cys Leu Cys Ser Gly Arg Lys Thr Ile Leu Glu Ile Tyr Pro Gly
1               5                   10                  15

Gln Phe Gln Pro Ser Leu Cys His Lys Phe Ile Ala Leu Ser Asp Lys
            20                  25                  30

Glu Gly Lys Leu Leu Arg Asn Tyr Thr Gln Asn Ile Asp Thr Leu Glu
        35                  40                  45

Gln Val Ala Gly Ile Gln Arg Ile Ile Gln Cys His Gly Ser Phe Ala
    50                  55                  60

Thr Ala Ser Cys Leu Ile Cys Lys Tyr Lys Val Asp Cys Glu Ala Val
65                  70                  75                  80

Arg Gly Asp Ile Phe Asn Gln Val Val Pro Arg Cys Pro Arg Cys Pro
                85                  90                  95

Ala Asp Glu Pro Leu Ala Ile Met Lys Pro Glu Ile Val Phe Phe Gly
            100                 105                 110

Glu Asn Leu Pro Glu Gln Phe His Arg Ala Met Lys Tyr Asp Lys Asp
        115                 120                 125

Glu Val Asp Leu Leu Ile Val Ile Gly Ser Ser Leu Lys Val Arg Pro
    130                 135                 140

Val Ala Leu Ile Pro Ser Ser Ile Pro His Glu Val Pro Gln Ile Leu
145                 150                 155                 160

Ile Asn Arg Glu Pro Leu Pro His Leu His Phe Asp Val Glu Leu Leu
                165                 170                 175

Gly Asp Cys Asp Val Ile Ile Asn Glu Leu Cys His Arg Leu Gly Gly
            180                 185                 190

Glu Tyr Ala Lys Leu Cys Cys Asn Pro Val Lys Leu Ser Glu Ile Thr
        195                 200                 205

Glu Lys Pro Pro Arg Thr Gln Lys Glu Leu Ala Tyr Leu Ser Glu Leu
    210                 215                 220

Pro Pro Thr Pro Leu His Val Ser Glu Asp Ser Ser Ser Pro Glu Arg
225                 230                 235                 240

Thr Ser Pro Pro Asp Ser Ser Val Ile Val Thr Leu Leu Asp Gln Ala
                245                 250                 255

Ala Lys Ser Asn Asp Asp Leu Asp Val Ser Glu Ser Lys Gly Cys Met
            260                 265                 270

Glu Glu Lys Pro Gln Glu Val Gln Thr Ser Arg Asn Val Glu Ser Ile
        275                 280                 285

Ala Glu Gln Met Glu Asn Pro Asp Leu Lys Asn Val Gly Ser Ser Thr
    290                 295                 300

Gly Glu Lys Asn Glu Arg Thr Ser Val Ala Gly Thr Val Arg Lys Cys
305                 310                 315                 320

Trp Pro Asn Arg Val Ala Lys Glu Gln Ile Ser Arg Arg Leu Asp Gly
                325                 330                 335

Asn Gln Tyr Leu Phe Leu Pro Pro Asn Arg Tyr Ile Phe His Gly Ala
            340                 345                 350
```

Glu Val Tyr Ser Asp Ser Glu Asp Val Leu Ser Ser Ser Cys
            355                 360                 365

Gly Ser Asn Ser Asp Ser Gly Thr Cys Gln Ser Pro Ser Leu Glu Glu
        370                 375                 380

Pro Met Glu Asp Glu Ser Glu Ile Glu Glu Phe Tyr Asn Gly Leu Glu
385                 390                 395                 400

Asp Glu Pro Asp Val Pro Glu Arg Ala Gly Gly Ala Gly Phe Gly Thr
                405                 410                 415

Asp Gly Asp Asp Gln Glu Ala Ile Asn Glu Ala Ile Ser Val Lys Gln
            420                 425                 430

Glu Val Thr Asp Met Asn Tyr Pro Ser Asn Lys Ser
            435                 440

<210> SEQ ID NO 7
<211> LENGTH: 110
<212> TYPE: DNA
<213> ORGANISM: Homo sapiens

<400> SEQUENCE: 7
ggccagctgt gagtgtttct ttggcagtgt cttagctggt tgttgtgagc aatagtaagg    60
aagcaatcag caagtatact gccctagaag tgctgcacgt tgtggggccc              110

<210> SEQ ID NO 8
<211> LENGTH: 102
<212> TYPE: DNA
<213> ORGANISM: Mus musculus

<400> SEQUENCE: 8
ccagctgtga gtaattcttt ggcagtgtct tagctggttg ttgtgagtat tagctaagga    60
agcaatcagc aagtatactg ccctagaagt gctgcacatt gt                      102

<210> SEQ ID NO 9
<211> LENGTH: 102
<212> TYPE: DNA
<213> ORGANISM: Rattus norvegicus

<400> SEQUENCE: 9
ccggctgtga gtaattcttt ggcagtgtct tagctggttg ttgtgagtat tagctaagga    60
agcaatcagc aagtatactg ccctagaagt gctgcacgtt gt                      102

<210> SEQ ID NO 10
<211> LENGTH: 66
<212> TYPE: DNA
<213> ORGANISM: Canis familiaris

<400> SEQUENCE: 10
tggcagtgtc ttagctggtt gttgtgagta atagtgaagg aagcaatcag caagtatact    60
gcccta                                                               66

<210> SEQ ID NO 11
<211> LENGTH: 91
<212> TYPE: DNA
<213> ORGANISM: Homo sapiens

<400> SEQUENCE: 11
ctgtgtgtga tgagctggca gtgtattgtt agctggttga atatgtgaat ggcatcggct    60
aacatgcaac tgctgtctta ttgcatatac a                                   91

```
<210> SEQ ID NO 12
<211> LENGTH: 91
<212> TYPE: DNA
<213> ORGANISM: Mus musculus

<400> SEQUENCE: 12
ctgtgtgtga tggcttggca gtgtattgtt agctggttga gtatgtgagc ggcaccagct    60
aacatgcgac tgctctccta ttgcacacac a                                   91

<210> SEQ ID NO 13
<211> LENGTH: 91
<212> TYPE: DNA
<213> ORGANISM: Rattus norvegicus

<400> SEQUENCE: 13
ctgtgtgcga tgggttggca gtgtattgtt agctggttga gtatgtaaaa ggcaccagct    60
aacatgcaac tgctctccta ttgcacatac a                                   91

<210> SEQ ID NO 14
<211> LENGTH: 91
<212> TYPE: DNA
<213> ORGANISM: Canis familiaris

<400> SEQUENCE: 14
ccgtgtgtga tgggttggca gtgtattgtt agctggttga atatatgaat ggcatcagct    60
aacatgcaac tgctatctta ttgcatatac a                                   91

<210> SEQ ID NO 15
<211> LENGTH: 97
<212> TYPE: DNA
<213> ORGANISM: Homo sapiens

<400> SEQUENCE: 15
tgacctgaat caggtaggca gtgtattgtt agctggctgc ttgggtcaag tcagcagcca    60
caactaccct gccacttgct tctggataaa ttcttct                             97

<210> SEQ ID NO 16
<211> LENGTH: 80
<212> TYPE: DNA
<213> ORGANISM: Mus musculus

<400> SEQUENCE: 16
agactcgggt aggcagtgtt gttagctggc tgcgttgggt caggccagca gccacagcta    60
ccctgccact tccttctggc                                                80

<210> SEQ ID NO 17
<211> LENGTH: 129
<212> TYPE: DNA
<213> ORGANISM: Canis familiaris

<400> SEQUENCE: 17
gccatgaaac gtagccgtga cctgagtcag gtaggcagtg tattgttagc tggctgcttt    60
gggtcaatct ggcagccacc actaccctgc cacttgcttc tggacaaatt cttctcatta   120
acaggctgc                                                           129

<210> SEQ ID NO 18
<211> LENGTH: 92
<212> TYPE: DNA
<213> ORGANISM: Homo sapiens
```

```
<400> SEQUENCE: 18
gctgggatgt gtcaggtagg cagtgtattg ctagcggctg ttaatgattt taacagttgc    60
tagttgcact cctctctgtt gcattcagaa gc                                  92

<210> SEQ ID NO 19
<211> LENGTH: 109
<212> TYPE: DNA
<213> ORGANISM: Mus musculus

<400> SEQUENCE: 19
aggatgaagt gtgggtgtgt caggcaggca gtgcattgct agctggctgt tagaaccttta   60 tcccaacagt tgctagctgc actaccctct gctgcactca gaagcatgc               109

<210> SEQ ID NO 20
<211> LENGTH: 90
<212> TYPE: DNA
<213> ORGANISM: Homo sapiens

<400> SEQUENCE: 20
ccgggcccct gtgagcatct taccggacag tgctggattt cccagcttga ctctaacact    60
gtctggtaac gatgttcaaa ggtgacccgc                                     90

<210> SEQ ID NO 21
<211> LENGTH: 90
<212> TYPE: DNA
<213> ORGANISM: Mus musculus

<400> SEQUENCE: 21
ctgggcctct gtgggcatct taccggacag tgctggattt cttggcttga ctctaacact    60
gtctggtaac gatgttcaaa ggtgacccac                                     90

<210> SEQ ID NO 22
<211> LENGTH: 89
<212> TYPE: DNA
<213> ORGANISM: Rattus norvegicus

<400> SEQUENCE: 22
ctgggcctct gtgggcatct taccggacag tgctggattt cttggcttga ctctaacact    60
gtctggtaac gatgttcaaa ggtgaccca                                      89

<210> SEQ ID NO 23
<211> LENGTH: 95
<212> TYPE: DNA
<213> ORGANISM: Homo sapiens

<400> SEQUENCE: 23
ccagctcggg cagccgtggc catcttactg ggcagcattg gatggagtca ggtctctaat    60
actgcctggt aatgatgacg gcggagccct gcacg                               95

<210> SEQ ID NO 24
<211> LENGTH: 70
<212> TYPE: DNA
<213> ORGANISM: Mus musculus

<400> SEQUENCE: 24
gccgtggcca tcttactggg cagcattgga tagtgtctga tctctaatac tgcctggtaa    60
tgatgacggc                                                           70
```

```
<210> SEQ ID NO 25
<211> LENGTH: 95
<212> TYPE: DNA
<213> ORGANISM: Rattus norvegicus

<400> SEQUENCE: 25
ccaacttggg cagccgtggc catcttactg ggcagcattg gatagtgtct gatctctaat      60
actgcctggt aatgatgacg gcggagccct gcacg                                 95

<210> SEQ ID NO 26
<211> LENGTH: 68
<212> TYPE: DNA
<213> ORGANISM: Homo sapiens

<400> SEQUENCE: 26
ccctcgtctt acccagcagt gtttgggtgc ggttgggagt ctctaatact gccgggtaat      60
gatggagg                                                               68

<210> SEQ ID NO 27
<211> LENGTH: 69
<212> TYPE: DNA
<213> ORGANISM: Mus musculus

<400> SEQUENCE: 27
ccctcgtctt acccagcagt gtttgggtgc tggttgggag tctctaatac tgccgggtaa      60
tgatggagg                                                              69

<210> SEQ ID NO 28
<211> LENGTH: 69
<212> TYPE: DNA
<213> ORGANISM: Rattus norvegicus

<400> SEQUENCE: 28
ccctcgtctt acccagcagt gtttgggtgc tggttgggag tctctaatac tgccgggtaa      60
tgatggagg                                                              69
```